US011235030B2

(12) United States Patent
Kestler et al.

(10) Patent No.: US 11,235,030 B2
(45) Date of Patent: *Feb. 1, 2022

(54) PLATELET-DERIVED GROWTH FACTOR COMPOSITIONS AND METHODS FOR THE TREATMENT OF TENDINOPATHIES

(71) Applicant: BioMimetic Therapeutics, LLC, Franklin, TN (US)

(72) Inventors: Hans K. Kestler, Brentwood, TN (US); Vivek Shah, Franklin, TN (US); Dean James Rager-Aguiar, Spring Hill, TN (US)

(73) Assignee: BioMimetic Therapeutics, LLC, Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/653,733

(22) Filed: Oct. 15, 2019

(65) Prior Publication Data

US 2020/0222504 A1 Jul. 16, 2020

Related U.S. Application Data

(63) Continuation of application No. 15/476,330, filed on Mar. 31, 2017, now Pat. No. 10,493,130, which is a continuation of application No. 13/923,967, filed on Jun. 21, 2013, now Pat. No. 9,642,892, which is a continuation of application No. 13/032,489, filed on Feb. 22, 2011, now Pat. No. 8,492,335.

(60) Provisional application No. 61/429,428, filed on Jan. 3, 2011, provisional application No. 61/428,809, filed on Dec. 30, 2010, provisional application No. 61/311,284, filed on Mar. 5, 2010, provisional application No. 61/306,938, filed on Feb. 22, 2010.

(51) Int. Cl.
*A61K 38/18* (2006.01)

(52) U.S. Cl.
CPC ............... *A61K 38/1858* (2013.01)

(58) Field of Classification Search
None
See application file for complete search history.

(56) References Cited

U.S. PATENT DOCUMENTS

| | | | |
|---|---|---|---|
| 3,943,072 A | 3/1976 | Thomson et al. |
| 4,845,075 A | 7/1989 | Murray et al. |
| 4,861,757 A | 8/1989 | Antoniades et al. |
| 4,874,746 A | 10/1989 | Antoniades et al. |
| RE33,161 E | 2/1990 | Brown et al. |
| 4,904,259 A | 2/1990 | Itay |
| 4,963,145 A | 10/1990 | Takagi et al. |
| 4,975,526 A | 12/1990 | Kuberasampath et al. |
| 5,011,910 A | 4/1991 | Marshall et al. |
| 5,013,649 A | 5/1991 | Wang et al. |
| 5,019,559 A | 5/1991 | Antoniades et al. |
| 5,034,375 A | 7/1991 | Antoniades et al. |
| 5,035,887 A | 7/1991 | Antoniades et al. |
| 5,045,633 A | 9/1991 | Murray et al. |
| 5,053,212 A | 10/1991 | Constantz et al. |
| 5,106,748 A | 4/1992 | Wozney et al. |
| 5,108,922 A | 4/1992 | Wang et al. |
| 5,112,354 A | 5/1992 | Sires |
| 5,116,738 A | 5/1992 | Wang et al. |
| 5,124,316 A | 6/1992 | Antoniades et al. |
| 5,128,321 A | 7/1992 | Murray et al. |
| 5,129,905 A | 7/1992 | Constantz |
| 5,141,905 A | 8/1992 | Rosen et al. |
| 5,149,691 A | 9/1992 | Rutherford |
| 5,165,938 A | 11/1992 | Knighton |
| 5,187,076 A | 2/1993 | Wozney et al. |
| 5,187,263 A | 2/1993 | Murray et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |
| 5,376,636 A | 12/1994 | Rutherford et al. |
| 5,457,093 A | 10/1995 | Cini et al. |
| 5,460,962 A | 10/1995 | Kemp |
| 5,516,896 A | 5/1996 | Murray et al. |
| 5,518,680 A | 5/1996 | Cima et al. |
| 5,531,794 A | 7/1996 | Takagi et al. |
| 5,533,836 A | 7/1996 | Moore |
| 5,549,123 A | 8/1996 | Okuyama et al. |

(Continued)

FOREIGN PATENT DOCUMENTS

| | | |
|---|---|---|
| EP | 0289584 A1 | 11/1988 |
| EP | 0479799 A1 | 4/1992 |

(Continued)

OTHER PUBLICATIONS

Chan et al., Clinical Orthopeadics and Related Research, 448:240-247, 2006.*
Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2F%2Fwww%2E7-ware%...>, lastvisited on Feb. 24, 2010, 2 pages.
Adalberto et al. "Periodontal Regeneration," J. Periodontal, 2005, 76(9):1601-1622.
Adornato, M.C. et al. (Jul. 2007). "The Treatment of Bisphosphonate-Associated Osteonecrosis of the Jaws with Bone Resection and Autologous Platelet-Derived Growth Factors," Journal of the American Dental Association 138(7):971-977.

(Continued)

*Primary Examiner* — Marianne P Allen
(74) *Attorney, Agent, or Firm* — Foley Hoag LLP; Hilary Dorr Lang

(57) ABSTRACT

Provided herein are compositions and methods for the treatment of tendinopathies, such as tenosynovitis, tendinosis or tendinitis, including Achilles tendinopathy, patellar tendinopathy, lateral epicondylitis or "tennis elbow," medial epicondylitis or "golfer's elbow," plantar fasciitis, and rotator cuff tendinopathy, and in particular to methods for the treatment of tendinopathies by administering compositions comprising platelet-derived growth factor (PDGF).

24 Claims, 12 Drawing Sheets

(56) References Cited

U.S. PATENT DOCUMENTS

| | | | |
|---|---|---|---|
| 5,599,558 A | 2/1997 | Gordinier et al. | |
| 5,629,191 A | 5/1997 | Cahn | |
| 5,635,372 A | 6/1997 | Celeste et al. | |
| 5,650,176 A | 7/1997 | Lee et al. | |
| 5,747,273 A | 5/1998 | Khosravi et al. | |
| 5,759,815 A | 6/1998 | Charette et al. | |
| 5,783,217 A | 7/1998 | Lee et al. | |
| 5,804,176 A | 9/1998 | Grotendorst | |
| 5,837,258 A | 11/1998 | Grotendorst | |
| 5,853,746 A | 12/1998 | Hunziker | |
| 5,866,165 A | 2/1999 | Liu et al. | |
| 5,962,028 A | 10/1999 | Constantz | |
| 5,965,403 A | 10/1999 | Celeste et al. | |
| 5,972,385 A | 10/1999 | Liu et al. | |
| 6,018,095 A | 1/2000 | Lerch et al. | |
| 6,027,742 A | 2/2000 | Lee et al. | |
| 6,077,989 A | 6/2000 | Kandel et al. | |
| 6,083,910 A | 7/2000 | Kunitani et al. | |
| 6,136,029 A | 10/2000 | Johnson et al. | |
| 6,180,606 B1 | 1/2001 | Chen et al. | |
| 6,214,368 B1 | 4/2001 | Lee et al. | |
| 6,221,625 B1 | 4/2001 | Ashihara et al. | |
| 6,224,635 B1 | 5/2001 | Ricci et al. | |
| 6,280,191 B1 | 8/2001 | Gordon | |
| 6,280,478 B1 | 8/2001 | Richter et al. | |
| 6,281,195 B1 | 8/2001 | Rueger et al. | |
| 6,287,341 B1 | 9/2001 | Lee et al. | |
| 6,313,189 B1 | 11/2001 | Wenz et al. | |
| 6,316,091 B1 | 11/2001 | Richart et al. | |
| 6,331,312 B1 | 12/2001 | Lee et al. | |
| 6,346,123 B1 | 2/2002 | McKay | |
| 6,398,972 B1 | 6/2002 | Blasetti et al. | |
| 6,440,444 B2 | 8/2002 | Boyce et al. | |
| 6,451,059 B1 | 9/2002 | Janas et al. | |
| 6,465,205 B2 | 10/2002 | Hicks, Jr. | |
| 6,468,543 B1 | 10/2002 | Gilbertson et al. | |
| 6,541,022 B1 | 4/2003 | Murphy et al. | |
| 6,541,037 B1 | 4/2003 | Lee et al. | |
| 6,558,307 B2 | 5/2003 | Headley | |
| 6,576,015 B2 | 6/2003 | Geistlich et al. | |
| 6,586,388 B2 | 7/2003 | Oppermann et al. | |
| 6,592,507 B2 | 7/2003 | Jorgensen et al. | |
| 6,599,558 B1 | 7/2003 | Al-Lamee et al. | |
| 6,613,566 B2 | 9/2003 | Kandler et al. | |
| 6,641,552 B1 | 11/2003 | Kingsley et al. | |
| 6,649,072 B2 | 11/2003 | Brandt et al. | |
| 6,652,473 B2 | 11/2003 | Kaufman et al. | |
| 6,663,870 B2 | 12/2003 | Hart et al. | |
| 6,710,025 B1 | 3/2004 | Spector | |
| 6,739,112 B1 | 5/2004 | Marino | |
| 6,743,232 B2 | 6/2004 | Overaker et al. | |
| 6,866,991 B2 | 3/2005 | Gilbertson et al. | |
| 6,884,428 B2 | 4/2005 | Binette et al. | |
| 6,903,078 B1 | 6/2005 | Williams | |
| 6,949,251 B2 | 9/2005 | Dalal et al. | |
| 6,972,130 B1 | 12/2005 | Lee et al. | |
| 6,974,862 B2 | 12/2005 | Ringeisen et al. | |
| 7,005,135 B2 | 2/2006 | Janas et al. | |
| 7,012,034 B2 | 3/2006 | Heide et al. | |
| 7,022,506 B2 | 4/2006 | Brighton et al. | |
| 7,041,641 B2 | 5/2006 | Rueger et al. | |
| 7,052,518 B2 | 5/2006 | Irie et al. | |
| 7,087,540 B2 | 8/2006 | Heide et al. | |
| 7,148,209 B2 | 12/2006 | Hoemann et al. | |
| 7,192,592 B2 | 3/2007 | Gilbertson et al. | |
| 7,192,604 B2 | 3/2007 | Brown et al. | |
| 7,250,550 B2 | 7/2007 | Overby et al. | |
| 7,357,941 B2 | 4/2008 | Dalal et al. | |
| 7,390,498 B2 | 6/2008 | Dalal et al. | |
| 7,473,678 B2 | 1/2009 | Lynch | |
| 7,491,384 B2 | 2/2009 | Hart et al. | |
| 7,597,883 B2 | 10/2009 | Hart et al. | |
| 7,799,754 B2 | 9/2010 | Hart et al. | |
| 7,866,485 B2 | 1/2011 | Dorian et al. | |
| 8,492,335 B2 * | 7/2013 | Kestler | A61P 29/00 514/8.2 |
| 9,642,892 B2 * | 5/2017 | Kestler | A61P 19/00 |
| 10,493,130 B2 * | 12/2019 | Kestler | A61P 21/00 |
| 2001/0014662 A1 | 8/2001 | Rueger et al. | |
| 2001/0016646 A1 | 8/2001 | Rueger et al. | |
| 2001/0016703 A1 | 8/2001 | Wironen et al. | |
| 2001/0020188 A1 | 9/2001 | Sander | |
| 2001/0038848 A1 | 11/2001 | Donda et al. | |
| 2002/0004225 A1 | 1/2002 | Hart et al. | |
| 2002/0006437 A1 | 1/2002 | Grooms et al. | |
| 2002/0018796 A1 | 2/2002 | Wironen | |
| 2002/0022885 A1 | 2/2002 | Ochi | |
| 2002/0037799 A1 | 3/2002 | Li et al. | |
| 2002/0082220 A1 | 6/2002 | Hoemann et al. | |
| 2002/0082694 A1 | 6/2002 | McKay | |
| 2002/0098222 A1 | 7/2002 | Wironen et al. | |
| 2002/0115647 A1 | 8/2002 | Halvorsen et al. | |
| 2002/0120281 A1 | 8/2002 | Overaker | |
| 2002/0127265 A1 | 9/2002 | Bowman et al. | |
| 2002/0131989 A1 | 9/2002 | Brown et al. | |
| 2002/0193883 A1 | 12/2002 | Wironen | |
| 2003/0006025 A1 | 1/2003 | Manini et al. | |
| 2003/0049328 A1 | 3/2003 | Dalal et al. | |
| 2003/0055511 A1 | 3/2003 | Schryver et al. | |
| 2003/0105015 A1 | 6/2003 | Gilbertson et al. | |
| 2003/0109000 A1 | 6/2003 | Moore et al. | |
| 2003/0109537 A1 | 6/2003 | Turner et al. | |
| 2003/0114936 A1 | 6/2003 | Sherwood et al. | |
| 2003/0125252 A1 | 7/2003 | Underhill et al. | |
| 2003/0152606 A1 | 8/2003 | Gerber | |
| 2003/0180376 A1 | 9/2003 | Dalal et al. | |
| 2003/0193106 A1 | 10/2003 | Yu et al. | |
| 2003/0199615 A1 | 10/2003 | Chaput et al. | |
| 2003/0203002 A1 | 10/2003 | Murphy et al. | |
| 2003/0224488 A1 | 12/2003 | Fox et al. | |
| 2003/0228364 A1 | 12/2003 | Nathan | |
| 2003/0232071 A1 | 12/2003 | Gower et al. | |
| 2003/0235622 A1 | 12/2003 | Tas | |
| 2004/0002770 A1 | 1/2004 | King et al. | |
| 2004/0014727 A1 | 1/2004 | Garrett | |
| 2004/0022825 A1 | 2/2004 | Lagow | |
| 2004/0033949 A1 | 2/2004 | Bunting et al. | |
| 2004/0043031 A1 | 3/2004 | Hart et al. | |
| 2004/0064194 A1 | 4/2004 | Irie et al. | |
| 2004/0076685 A1 | 4/2004 | Tas | |
| 2004/0078077 A1 | 4/2004 | Binette et al. | |
| 2004/0078090 A1 | 4/2004 | Binette et al. | |
| 2004/0197311 A1 | 10/2004 | Brekke et al. | |
| 2004/0224027 A1 | 11/2004 | Spiro et al. | |
| 2004/0228870 A9 | 11/2004 | Hart et al. | |
| 2004/0230303 A1 | 11/2004 | Gomes et al. | |
| 2004/0243133 A1 | 12/2004 | Materna | |
| 2004/0265350 A1 | 12/2004 | Sambrook et al. | |
| 2005/0027367 A1 | 2/2005 | Heide et al. | |
| 2005/0031694 A1 | 2/2005 | Gilbertson et al. | |
| 2005/0074481 A1 | 4/2005 | Brekke et al. | |
| 2005/0098915 A1 | 5/2005 | Long et al. | |
| 2005/0107162 A1 | 5/2005 | Kilby et al. | |
| 2005/0107887 A1 | 5/2005 | Knothe Tate et al. | |
| 2005/0119754 A1 | 6/2005 | Trieu et al. | |
| 2005/0169893 A1 | 8/2005 | Koblish et al. | |
| 2005/0170012 A1 | 8/2005 | Dalal et al. | |
| 2005/0177203 A1 | 8/2005 | Brighton et al. | |
| 2005/0187162 A1 | 8/2005 | Dhanaraj et al. | |
| 2006/0029578 A1 | 2/2006 | Hoemann et al. | |
| 2006/0149392 A1 | 7/2006 | Hsieh et al. | |
| 2006/0153817 A1 | 7/2006 | Kihm et al. | |
| 2006/0153818 A1 | 7/2006 | Dhanaraj et al. | |
| 2006/0154367 A1 | 7/2006 | Kihm et al. | |
| 2006/0177475 A1 | 8/2006 | Rueger et al. | |
| 2006/0190043 A1 | 8/2006 | Brighton et al. | |
| 2006/0198939 A1 | 9/2006 | Smith et al. | |
| 2006/0205652 A1 | 9/2006 | Zamora et al. | |
| 2006/0233853 A1 | 10/2006 | Remington et al. | |
| 2006/0247156 A1 | 11/2006 | Vanderby et al. | |
| 2006/0292198 A1 | 12/2006 | Dalal et al. | |
| 2007/0003752 A1 | 1/2007 | Bruce et al. | |
| 2007/0026044 A1 | 2/2007 | Bunting et al. | |

(56) References Cited

U.S. PATENT DOCUMENTS

| | | | |
|---|---|---|---|
| 2007/0048381 A1 | 3/2007 | Hart et al. | |
| 2007/0053951 A1 | 3/2007 | Gonzalez Santos et al. | |
| 2007/0160681 A1 | 7/2007 | Park et al. | |
| 2007/0190101 A1 | 8/2007 | Yang et al. | |
| 2007/0191851 A1 | 8/2007 | Ashammakhi | |
| 2007/0218098 A1 | 9/2007 | Reif et al. | |
| 2007/0244484 A1 | 10/2007 | Luginbuehl | |
| 2007/0259018 A1 | 11/2007 | McKay | |
| 2007/0259814 A1 | 11/2007 | Lynch | |
| 2007/0260326 A1 | 11/2007 | Williams et al. | |
| 2007/0282455 A1 | 12/2007 | Luginbuehl et al. | |
| 2008/0027470 A1* | 1/2008 | Hart | A61L 27/12 606/151 |
| 2008/0193424 A1 | 8/2008 | McKale et al. | |
| 2008/0200372 A1 | 8/2008 | Ghosh | |
| 2009/0054339 A1 | 2/2009 | Marshall et al. | |
| 2009/0092674 A1 | 4/2009 | Ingram et al. | |
| 2009/0130173 A1 | 5/2009 | Behnam et al. | |
| 2009/0181093 A1 | 7/2009 | Thorne et al. | |

FOREIGN PATENT DOCUMENTS

| | | |
|---|---|---|
| EP | 0530804 A1 | 3/1993 |
| EP | 0741785 A1 | 11/1996 |
| EP | 0896825 A1 | 2/1999 |
| EP | 0994694 A1 | 4/2000 |
| EP | 1025871 A1 | 8/2000 |
| EP | 1146897 A1 | 10/2001 |
| EP | 1234552 A1 | 8/2002 |
| EP | 1242129 A2 | 9/2002 |
| EP | 1100488 B1 | 4/2003 |
| EP | 1374857 A1 | 1/2004 |
| EP | 1410811 A1 | 4/2004 |
| EP | 1464307 A1 | 10/2004 |
| EP | 1561481 A2 | 8/2005 |
| EP | 1563846 A1 | 8/2005 |
| EP | 1681087 A2 | 7/2006 |
| EP | 1712244 A1 | 10/2006 |
| EP | 1719531 A2 | 11/2006 |
| EP | 1719532 A2 | 11/2006 |
| GB | 02367497 A | 4/2002 |
| JP | 7250688 A | 10/1995 |
| JP | 2003265592 A | 9/2003 |
| WO | WO-88/03409 A1 | 5/1988 |
| WO | WO-91/15231 A1 | 10/1991 |
| WO | WO-91/18098 A1 | 11/1991 |
| WO | WO-92/09301 A1 | 6/1992 |
| WO | WO-92/16181 A2 | 10/1992 |
| WO | WO-93/00432 A1 | 1/1993 |
| WO | WO-93/05808 A1 | 4/1993 |
| WO | WO-93/08825 A1 | 5/1993 |
| WO | WO-93/09229 A1 | 5/1993 |
| WO | WO-93/16099 A2 | 8/1993 |
| WO | WO-93/20859 A1 | 10/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO-94/21681 A1 | 9/1994 |
| WO | WO-94/22463 A1 | 10/1994 |
| WO | WO-94/26892 A1 | 11/1994 |
| WO | WO-94/26893 A1 | 11/1994 |
| WO | WO-94/28889 A1 | 12/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/18856 A1 | 7/1995 |
| WO | WO-95/20967 A1 | 8/1995 |
| WO | WO-95/28124 A2 | 10/1995 |
| WO | WO-95/28950 A1 | 11/1995 |
| WO | WO-96/01845 A1 | 1/1996 |
| WO | WO-96/02559 A1 | 2/1996 |
| WO | WO-96/13226 A1 | 5/1996 |
| WO | WO-96/16668 A1 | 6/1996 |
| WO | WO-96/17924 A2 | 6/1996 |
| WO | WO-97/13857 A1 | 4/1997 |
| WO | WO-98/00183 A2 | 1/1998 |
| WO | WO-98/40113 A1 | 9/1998 |
| WO | WO-98/41246 A2 | 9/1998 |
| WO | WO-98/51354 A2 | 11/1998 |
| WO | WO-99/30726 A1 | 6/1999 |
| WO | WO-99/38543 A2 | 8/1999 |
| WO | WO-99/67289 A1 | 12/1999 |
| WO | WO-00/04940 A1 | 2/2000 |
| WO | WO-01/32197 A2 | 5/2001 |
| WO | WO-01/35932 A2 | 5/2001 |
| WO | WO-01/41822 A1 | 6/2001 |
| WO | WO-01/57083 A1 | 8/2001 |
| WO | WO-01/60424 A2 | 8/2001 |
| WO | WO-01/66044 A2 | 9/2001 |
| WO | WO-01/66130 A1 | 9/2001 |
| WO | WO-01/68135 A2 | 9/2001 |
| WO | WO-02/00244 A2 | 1/2002 |
| WO | WO-02/00272 A2 | 1/2002 |
| WO | WO-02/36147 A1 | 5/2002 |
| WO | WO-02/062405 A2 | 8/2002 |
| WO | WO-02/067978 A1 | 9/2002 |
| WO | WO-02/070029 A2 | 9/2002 |
| WO | WO-02/102783 A1 | 12/2002 |
| WO | WO-03/006025 A1 | 1/2003 |
| WO | WO-03/043576 A2 | 5/2003 |
| WO | WO-03/065996 A2 | 8/2003 |
| WO | WO-03/070186 A2 | 8/2003 |
| WO | WO-03/071997 A1 | 9/2003 |
| WO | WO-2004/002539 A2 | 1/2004 |
| WO | WO-2004/010907 A1 | 2/2004 |
| WO | WO-2004/071543 A1 | 8/2004 |
| WO | WO-2004/073563 A2 | 9/2004 |
| WO | WO-2004/110308 A2 | 12/2004 |
| WO | WO-2005/009496 A1 | 2/2005 |
| WO | WO-2005/032461 A2 | 4/2005 |
| WO | WO-2005/042048 A2 | 5/2005 |
| WO | WO-2005/046746 A2 | 5/2005 |
| WO | WO-2005/054279 A1 | 6/2005 |
| WO | WO-2005/072656 A1 | 8/2005 |
| WO | WO-2006/031388 A2 | 3/2006 |
| WO | WO-2006/034365 A2 | 3/2006 |
| WO | WO-2006/050493 A2 | 5/2006 |
| WO | WO-2006/093808 A1 | 9/2006 |
| WO | WO-2006/133403 A2 | 12/2006 |
| WO | WO-2007/087436 A2 | 8/2007 |
| WO | WO-2007/089997 A2 | 8/2007 |
| WO | WO-2007/090102 A2 | 8/2007 |

OTHER PUBLICATIONS

Aghaloo, T.L. DDS MD et al. "Evaluation of Platelet-Rich Plasma in Combination with Anorganic Bovine Bone in the Rabbit Cranium: A Pilot Study," The International Journal of Oral and Maxillofacial Implants; 2004, 19:59-65.

Ahn, S-H. et al. (Jun. 2003). "Effect of Recombinant Human Bone Morphogenetic Protein-4 with Carriers in Rat Calvarial Defects," Journal of Periodontology 74(6):787-797.

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," Tissue Eng. 10(5/6):789-795.

Almojaly, S. (2008). "The Effect of Bisphosphonate, Alendronate, on Primary Human Alveolar Bone Cells," Masters Abstracts International 46(6):61.

Anitua et al. (2005). "Autologous Preparations Rich in Growth Factors Promote Proliferation and Induce VEGF and HGF Production by Human Tendon Cells in Culture," Journal of Orthopaedic Research 23:281-286.

Anitua, E. et al., "Autologous platelets as a source of proteins for healing and tissue regeneration," Thromb Haemost, 2004, 91:4-15.

Anonymous (2003). "The European Market for Dental Bone Graft Substitutes," Implant Dentistry 12(1):3-5.

(56) References Cited

OTHER PUBLICATIONS

Antoniades, H.N. et al. (1985). "Platelet-Derived Growth Factor: A Link to Malignant Transformation," in Cancer Cells 3: Growth Factors and Transformations, Fermasico, J. et al. eds., Cold Spring Harbor Laboratory: Cold Spring Harbor, NY, 3:145-151.

Antoniades, H.N. et al. (1991). "Molecular Mechanism of Tissue Repair: Injury Induces Expression of PDGF-B and its Receptor," Abstract No. 2156, J. Dental Res. 70:536.

Antoniades, H.N. et al. (May 27, 1983). "Human Platelet-Derived Growth Factor (PDGF): Amino-Terminal Amino Acid Sequence," Science 220:963-965.

Anusaksathien et al. "Effect of Sustained Gene Delivery of Platelet-Derived Growth Factor or Its Antagonist (PDGF-1308) on Tissue-Engineered Cementum," J. Periodontal, Mar. 2004, 75(3):429-440.

Anusaksathien et al., "Growth Factor Delivery to Re-Engineer Periodontal Tissues," Current Pharmaceutical Biotechnology, 2002, vol. 3(2): 129-139.

Anusaksathien et al., "Platelet-Derived Growth Factor Gene Delivery Stimulates ex Vivo Gingival Repair," Tissue Engineering, 2003, 9(4): 745-756.

Arm, D.M. et al. "Effect of Controlled Release of Platelet-derived Growth Factor from a Porous Hydroxyapatite Implant on Bone Ingrowth," Biomaterials, 1996, 17(7):703-709.

Assael, L.A. (2006). "A Time for Perspective on Bisphosphonates," J. Oral Maxillofac. Surg. 64:877-879.

Babbush, C.A. DDS MSCD et al. "An In Vitro and In Vivo Evaluation of Autologous Platelet Concentrate in Oral Reconstruction," Implant Dent., 2003, 12(1):24-34.

Barker, K. et al. (Jun. 2006). "Bisphosphonate-Associated Osteonecrosis of the Jaws: A Guide for the General Dental Practitioner," Dental Update pp. 270-275.

Basa, S. et al. (2004). "Alternative Bone Expansion Technique for Immediate Placement of Implants in the Edentulous Posterior Mandibular Ridge: A Clinical Report," International Journal of Oral & Maxofacial Implants 19(4):554-558.

Bateman, J. et al. "Platelet-Derived Growth Factor Enhancement of Two Alloplastic Bone Matrices," J. Periodontol. (Nov. 2005) 76(11):1833-1841.

Becker. W. et al. (Nov. 1992). "A Comparison of ePTFE Membranes Alone or in Combination with Platelet-Derived Growth Factor and Insulin-Like Growth Factor-I, or Demineralized Freeze Dried Bone in Promoting Bone Formation Around Immediate ExtractionSocket Implants: A Study in Dogs," J. Periodtonol. 63(11):929-940.

Berlemann, U. et al. (2002). "Adjacent Vertebral Failure After Vertebroplasty," J. Bone Joint Surg. BR 84(B):748-752.

Betsholtz, C. et al. (Apr. 24, 1986). "cDNA Sequence and Chromosomal Localization of Human Platelet-Derived Growth Factor A-Chain and its Expression in Tumour Cell Lines," Nature 320:695-699.

Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressrel- easedtl.htm&StoryID=185&>, last visited on May 18, 2010, 8 pages.

Biomimetic Therapeutics (Aug. 11, 2008). "BioMimetic Therapeutics Reports 2008 Second Quarter Results; Positive Results Achieved with Augment. TM. Injectable Bone Graft to Enhance Healing in Foot and Ankle Fusions," located at<http://biomimetics.com/cgi-bin/aw/acuweb.cgi?s=biomimetics&t=pressrel- easedtl.htm&StoryID=151&>, last visited on May 18, 2010, 8 pages.

Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics&t=pressrel- easedtl.htm&StoryID=125&>, last visited on May 18, 2010,7 pages.

Biomimetic Therapeutics (Aug. 21, 2002). "Orthovita and BioMimetic Enter into a Supply Agreement," located at <http://biomimetics.com/cgi-bin/aw/acuweb.cgi?s=biomimetics&t=pressrel- easedtl.htm&StoryID=82&>, last visited on May 18, 2010, 6pages.

Biomimetic Therapeutics (Dec. 11, 2008). "BioMimetic Therapeutics, Inc. Achieves Patient Enrollment Target (396) in North American Pivotal Study for Augment.TM. Bone Graft," located at<http://biomimetics.com/cgi-bin/aw/acuweb.cgi?s=biomimetics&t=pressrel-easedtl.htm&StoryID=169&>, last visited on May 18, 2010, 5 pages.

Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressrel-easedtl.htm&StoryID=104&>, last visited on May 18, 2010, 7 pages.

Biomimetic Therapeutics (Dec. 13, 2007). "BioMimetic Therapeutics reports Positive Clinical Results for GEM OS.RTM. 1 in Canadian Foot and Ankle Fusion Study; Clinical Success Rate of 90% Achieved in High Risk Patient Population," located at<http://biomimetics.com/cgi-bin/aw/acuweb.cgi?s=biomimetics&t=pressrel- easedtl.htm&StoryID=131&>, last visited on May 18, 2010, 6 pages.

Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at<http://biomimetics.com/cgi-bin/aw/acuweb.cgi?s=biomimetics&t=pressrel- easedtl.htm&StoryID=149&>, last visited on May 18, 2010, 7 pages.

Biomimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressrel- easedtl.htm&StoryID=199&>, last visited on May 18, 2010, 5 pages.

Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressrel- easedtl.htm&StoryID=83&>, last visited onMay 18, 2010, 6 pages.

Biomimetic Therapeutics (Feb. 19, 2009). "BioMimetic Therapeutics, Inc. to Highlight Pre-Clinical and Clinical Activities at ORS and AAOS Meetings; Company to Host an Analyst and Investor Meeting Feb. 26," located at<http://biomimetics.com/cgi-bin/aw/acuweb.cgi?s=biomimetics&t=pressrel- easedtl.htm&StoryID=154&>, last visited on May 18, 2010, 6 pages.

BioMimetic Therapeutics (Feb. 21, 2007). "BioMimetic Therapeutics Receives Orphan Drug Designation for rhPDGF-BB Treatment of Osteonecrosis of the Jaw," located at < http://biomimetics.com/cgi-bin/aw/acuweb.cgi?s=biomimetics&t=pressrelease-dtl.htm&StoryID=112&>, last visited on Apr. 5, 2010, 6 pages.

Biomimetic Therapeutics (Feb. 29, 2008). "BioMimetic Therapeutics, Inc. to Highlight Clinical and Preclinical Activities at ORS and AAOS Meetings," located at http://biomimetics.com/cgi-bin/aw/acuweb.cgi?s=biomimetics&t=pressrelease-dtl.htm&StoryID=136&>, last visited on May 18, 2010, 6 pages.

Biomimetic Therapeutics (Jan. 25, 2007). "BioMimetic Therapeutics Reports Positive Clinical Results Using GEM OS.RTM. 1 to Treat Distal Radius Fractures," located at <http://biomimetics.com/cgi-bin/aw/acuweb.cgi?s=biomimetics&t=pressrel-easedtl.htm&StoryID=105&>, last visited on May 18, 2010, 6 pages.

Biomimetic Therapeutics (Jan. 7, 2009). "BioMimetic Therapeutics, Inc. Closes Enrollment with 436 Patients in North American Pivotal Study for Augment.TM. Bone Graft; Company Will File Modular PMA with the FDA Beginning This Spring," located at<http://biomimetics.com/cgi-bin/aw/acuweb.cgi?s=biomimetics&t=pressrel- easedtl.htm&StoryID=168&>, last visited on May 18, 2010, 5 pages.

Biomimetic Therapeutics (Jul. 11, 2006). "BioMimetic Therapeutics Successfully Completes Enrollment in Three Orthopedic Pilot Clinical Trials for GEM OS1.TM. Bone Graft; Canadian Study Expanded to 60 Patients," located at<http://biomimetics.com/cgi-bin/aw/acuweb.cgi?s-biomimetics&t-pressrel- easedtl.htm&StoryID-93&>, last visited on May 18, 2010, 6 pages.

Biomimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressrel- easedtl.htm&StoryID=81&>, last visited on May 20, 2010, 6 pages.

(56) References Cited

OTHER PUBLICATIONS

Biomimetic Therapeutics (Jul. 13, 2007). "BioMimetic Therapeutics' Clinical Investigator Presents Positive Interim Data on U.S. and Canadian Foot and Ankle Clinical Trials," located at<http://biomimetics.com/cgi-bin/aw/acuweb.cgi?s=biomimetics&t=pressrel-easedtl.htm&StoryID=123&>, last visited on May 18, 2010, 8 pages.

Biomimetic Therapeutics (Jul. 15, 2004). "BioMimetic Pharmaceuticals' Receives Approvable Recommendation from FDA Advisory Panel for GEM 21S.RTM.," located at <http://biomimetics.com/cgi-bin/aw/acuweb.cgi?s=biomimetics&t=pressrel-easedtl.htm&StoryID=78&>, last visited on May 18, 2010, 6 pages.

Biomimetic Therapeutics (Jun. 7, 2006). "BioMimetic Therapeutics Receives Approval to Market GEM 21S.RTM. Growth-Factor Enhanced Matrix in Canada," located at <http://www. biomimetics.com/cgi-bin/acuweb/acuweb.cgi?s=biom&t=NewsDet-ail.htm&StoryID=166&>, 5 pages.

Biomimetic Therapeutics (Jun. 7, 2007). "BioMimetic Therapeutics Initiates Enrollment in E.U. Registration Trial for GEM OS.RTM. 1 Bone Graft; U.S. GEM OS1 Pivotal Study Protocol Amended to Allow Shorter Follow-Up Time and More Patients," located at<http://biomimetics.com/cgi-bin/aw/acuweb.cgi?s=biomimetics&t=pressrel-easedtl.htm&StoryID=119&>, last visited on May 18, 2010, 6 pages.

Biomimetic Therapeutics (Mar. 11, 2010). "BioMimetic Therapeutics Reports 2009 Fourth Quarter and Year End Earnings Results; Company Releases Additional Pivotal Data on Augment," located at<http://biomimetics.com/cgi-bin/aw/acuweb.cgi?s=biomimetics&t=pressrel-easedtl.htm&StoryID=203&>, last visited on May 18, 2010, 11 pages.

Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at<http://biomimetics.com/cgi-bin/aw/acuweb.cgi?s-biomimetics&t-pressrel- easedtl.htm&StoryID-137&>, last visited on May 18, 2010, 8 pages.

Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressrel- easedtl.htm&StoryID=160&>, last visited onMay 18, 2010, 11 pages.

BioMimetic Therapeutics (Mar. 12, 2010). "Morningstar.RTM. Document ResearchSM Form 10-K," United States Securities and Exchange Commission Annual Report, located at <http://investor.biomimetics.com/phoenix.zhtml?c=196896&p=irol-sec>-, lastvisited on May 19, 2010, 247 pages.

Biomimetic Therapeutics (Mar. 20, 2006). "BioMimetic Therapeutics Initiates Trials with Novel Bio-Active Drug-Device Combination Bone Graft in Two Orthopedic Indications," located at<http://biomimetics.com/cgi-bin/aw/acuweb.cgi?s=biomimetics&t=pressrel-easedtl.htm&StoryID=118&>, last visited on May 18, 2010, 6 pages.

Biomimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at<http://biomimetics.com/cgi-bin/aw/acuweb.cgi?s-biomimetics&t-pressrel- easedtl.htm&StoryID-113&>, last visited on May 18, 2010, 8 pages.

Biomimetic Therapeutics (Mar. 4, 2010). "BioMimetic Therapeutics, Inc. to Highlight Pre-Clinical and Clinical Activities at ORS and AAOS Meetings; Company to Host Analyst and Investor Meeting on Mar. 11," located at<http://biomimetics.com/cgi-bin/aw/acuweb.cgi?s=biomimetics&t=pressrel- easedtl.htm&StoryID=201&>, last visited on May 18, 2010, 6 pages.

Biomimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at<http://biomimetics.com/cgi-bin/aw/acuweb.cgi?s=biomimetics&t=pressrel- easedtl.htm&StoryID=138&>, last visited on May 18, 2010, 6 pages.

Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s-biomimetics&t-pressrel-easedtl.htm&StoryID=202&>, last visited on May 18, 2010, 6 pages.

Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressrel- easedtl.htm&StoryID=111&>, lastvisited on May 18, 2010, 4 pages.

Biomimetic Therapeutics (May 14, 2007). "BioMimetic Therapeutics Reports 2007 First Quarter Results; Company Added to NAS-DAQ Biotechnology Index," located at <http://biomimetics.com/cgi-bin/aw/acuweb.cgi?s=biomimetics&t=pressrel-easedtl.htm&StoryID=116&>, last visited on May 18, 2010, 7 pages.

Biomimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics&t=pressrel- easedtl.htm&StoryID=80&>, last visitedon May 18, 2010, 6 pages.

Biomimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressrel- easedtl.htm&StoryID=76&>, last visited on May 18, 2010, 5 pages.

Biomimetic Therapeutics (May 7, 2009). "BioMimetic Therapeutics Releases 2009 First Quarter Financial Results," located at <http://biomimetics.com/cgi-bin/aw/acuweb.cgi?s-biomimetics&t-pressrel- easedtl.htm&StoryID-167&>, last visited on May 18, 2010, 8 pages.

Biomimetic Therapeutics (Nov. 10, 2008). "BioMimetic Therapeutics Reports 2008 Third Quarter Results," located at <http://biomimetics.com/cgi-bin/aw/acuweb.cgi?s=biomimetics&t=pressrel- easedtl.htm&StoryID=157&>, last visited on May 18, 2010,8 pages.

Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics&t=pressrel- easedtl.htm&StoryID=127&>, last visited on May 18, 2010,7 pages.

Biomimetic Therapeutics (Nov. 21, 2005). "BioMimetic Therapeutics Announces FDA Approval of GEM 21S.RTM. Growth-Factor Enhanced Matrix for the Treatment of Periodontally-Related Bone Defects," located at<http://biomimetics.com/cgi-bin/aw/acuweb.cgi?s=biomimetics&t=pressrel- easedtl.htm&StoryID=87&>, last visited on May 18, 2010, 6 pages.

Biomimetic Therapeutics (Nov. 21, 2008). "BioMimetic Therapeutics, Inc. Announces Patent Allowance from the United States Patent and Trademark Office for PDGF Compositions Patent; Expanded Protection for Augment.TM., Augment.TM. Injectable and GEM21S.RTM. Until 2024," located at <http://biomimetics.com/cgi-bin/aw/acuweb.cgi?s-biomimetics&t-pressrel- easedtl.htm&StoryID-163&>, last visited on May 18, 2010, 5 pages.

Biomimetic Therapeutics (Nov. 3, 2009). "BioMimetic Therapeutics Receives First Orthopedic Marketing Approval for Augment Bone Graft," located at <http://biomimetics.com/cgi-bin/aw/acuweb.cgi?s=biomimetics&t=pressrel-easedtl.htm&StoryID=190&>, last visited on May 18, 2010, 6 pages.

Biomimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics&t=pressrel- easedtl.htm&StoryID=79&>, last visited on May 20, 2010, 5 pages.

Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at<http://biomimetics.com/cgi-bin/aw/acuweb.cgi?s=biomimetics&t=pressrel- easedtl.htm&StoryID=191&>, last visited on May 18, 2010, 8 pages.

Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.

(56) References Cited

OTHER PUBLICATIONS cgi?s=biomimetics&t=pressrel-easedtl.htm&StoryID=101 &>, last visited on May 18, 2010, 7 pages.
BioMimetic Therapeutics (Oct. 13, 2009). "BioMimetic Announces Positive Top-Line Data from its Augment Bone Graft North American Pivotal Trial; Augment Demonstrates Non-Inferiority to Autograft," located at <http://biomimetics.com/cgi-bin/aw/acuweb.cgi?s=biomimetics&t=pressrelease- dtl.htm&StoryID=188&>, last visited on May 18, 2010, 8 pages.
Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396Patients Enrolled," located at <http://biomimetics.com/cgi-bin/aw/acuweb.cgi?s=biomimetics&t=pressrel-easedtl.htm&StoryID-159&>, last visited on May 18, 2010, 6 pages.
Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at<http://biomimetics.com/cgi-bin/aw/acuweb.cgi?s=biomimetics&t=pressrel- easedtl.htm&StoryID=94&>, last visited on May 18, 2010, 6 pages.
Biomimetic Therapeutics (Sep. 23, 2008). "BioMimetic Therapeutics Announces No Changes Requested by Independent Data Monitoring Committee to Pivotal Trial Design for Augment.TM. Bone Graft; 268 of 396 Patients Enrolled to Date in U.S. PivotalTrial," located at <http://biomimetics.com/cgi-bin/aw/acuweb.cgi?s=biomimetics&t=pressrel-easedtl.htm&StoryID=153&>, last visited on May 18, 2010, 7 pages.
Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics&t=pressrel- easedtl.htm&StoryID=97&>, last visited on May 20, 2010, 6 pages.
Bjorkenheim, J.M. (1989). "Structure and Function of the Rabbit's Supraspinatus Muscle After Resection of its Tendon," Acta Orthop. Scand. 60(4):461-463.
Boileau, P. et al. (Jun. 2005). "Arthroscopic Repair of Full-Thickness Tears of the Supraspinatus: Does the Tendon Really Heal?" J. Bone Joint Surg. Am. 87-A(6):1229-1240.
Bolander, "Regulation of Fracture Repair by Growth Factors," P.S.E.B.M., 1992, 200: 165-170.
Bonfini, T. et al. (Jan. 1, 2006). "Autologous Marrow and Platel Gel in Bone Tissue Regeneration," Cytotherapy 8(1), Abstract No. 239, 2 pages.
Bora, F.W. Jr. et al. (Aug. 1987). "Joint Physiology, Cartilage Metabolism, and the Etiology of Osteoarthritis," Hand Clin. 3(3):325-336.
Boyden, E.M. et al. (Aug. 1995). "Late Versus Early Repair of Achilles Tendon Rupture: Clinical and Biomechanical Evaluation," Clin. Orthop. Relat. Res. 317:150-158.
Braddock, M. et al. (Oct. 2001). "Born Again Bone: Tissue Engineering for Bone Repair," News Physiool. Sci. 16:208-213.
Buser, D. et al. (1991). "Effects of Growth Factors on Bone Regeneration Around Titanium Implants," Abstract No. 282, J. Dental Res. 70:301.
Business Wire (May 29, 2002). "Orthovita Issued Patent for Biomaterials Platform Designed to Facilitate Natural Mechanism of Action in Bone Healing," located at <http://www.highbeam.com/doc/1G1-86413645.html>, last visited on Jun. 17, 2010, 3pages.
Business Wire. (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at<http://www.highbeam.com/doc/1G1-68027113.html>, last visited on Apr. 26, 2010, 3 pages.
Camargo, et al, "Platelet-rich plasma and bovine porous bone mineral combined with guided tissue regeneration in the treatment of intrabony defects in humans," J Periodont Res 2002, 37: 300-306.

Camargo, L.V. PM et al., "Effectiveness of a combination of platelet-rich plasma, bovine porous bone mineral and guided tissue regeneration in the treatment of mandibular grade II molar furcations in humans," J. Clin. Periodontol, 2003, 30:746-751.
Camelo et al. "Periodontal regeneration with an autogenous bone-bio-oss composite graft and a bio-guide membrane," International Journal of Periodontics and Restorative Dentistry. 2001, 21(2):109-120.
Camelo et al., "Clinical, radiographic, and histologic evaluation of human periodontal defects treated with bio-oss and bio-guide," International Journal of Periodontics and Restorative Dentistry, 1998, 18(4): 321-332.
Camelo, M. et al. (Nov. 3, 2003). "Periodontal Regeneration in Human Class II Furcations Using Purified Recombinant Human Platelet-Derived Growth Factor-BB (rhPDGF-BB) with Bone Allograft," International Journal of Periodontics & RestorativeDentistry 23(3):213-225.
Canalis, "Effect of Growth Factors on Bone Cell Replication and Differentiation," Clinical Orthopedics and Related Research, Mar. 1985, 193:246-263.
Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," J. Periodontol. 71(1):1743-1749.
Catalano, L. et al. (2006). "Bisphoshonates and Risk of Osteonecorisis of the Jaws," Haema 9(3):410-414.
Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," Acta Orthop. Scand. 74(5):559-564.
Cenni, E. et al. (2005, e-pub. Feb. 1, 2005). "Plasma Levels of Platelet-Derived Growth Factor BB and Transforming Growth Factor in Patients with Failed Hip Protheses," Acta Orthopaedica 76(1):64-66.
Chalmers, J. (Jun. 2000). "Review Article: Treatment of Achilles Tendon Ruptures," J. Orthop. Surg. 8(1):97-99.
Chen et al. "Adenoviral Gene Transfer of PDGF Downregulates Gas Gene Product PDGFR and Prolongs ERK and AktIPKB Activation," Am J Physiol Cell Physiol., Mar. 2002, 282:C538-C544.
Chiandussi, S. et al. (2006). "Clinical and Diagnostic Imaging of Bisphosphonate-Associated Osteonecrosis of the Jaws," Dentomaxillofacial Radiology 35:236-243.
Chin, M. (1995). "Distraction Osteogenesis in Maxillofacial Surgery," Chapter 9 in Tissue Engineering: Applications in Maxillofacial Surgery and Periodontics, Lynch, S.E. et al. eds., Quintessence Publishing, pp. 147-159.
Cho et al. (Jun. 1995). "Platelet Derived Growth Factor— Modulated Guided Tissue Regenerative Therapy," J. Peridontol. 66(6):522-530.
Clain, M.R. et al. (Oct. 1992). "Achilles Tendinitis," Foot Ankle Int. 13(8):482-487.
Clergeau, L.P. et al. (Feb. 1996). "Healing Response to Anorganic Bone Implantation in Periodontal Intrabony Defects in Dogs Part 1. Bone Regeneration. A Microradiographic Study," J. Periodontool. 67(2):140-149.
Cochran, et al. "Effects of Platelet-Derived Growth Factor Isoforms on Calcium Release From Neonatal Mouse Calvariae," Bone, 1993, 14: 53-58.
Coleman, S.H. et al. (Dec. 2003). "Chronic Rotator Cuff Injury and Repair Model in Sheep," The Journal of Bone and Joint Surgery 85-A(12):2391-2402.
Collins, T. et al. (Aug. 22, 1985). "Cultured Human Endothelial Cells Express Platelet-Derived Growth Factor B Chain: cDNA Cloning and Structural Analysis," Nature 316:748-750.
Convery, F.R. et al. (Jan.-Feb. 1972). "The Repair of Large Osteochondral Defects. An Experimental Study in Horses," Clin. Orthop. Relat. Res. 82:253-262.
Cooke et al., "Effect of rhPDGR-BB Delivery on Mediators of Periodontal Wound Repair," Tissue Engineering, 2006, 12(6): 1441-1450.
Costa, M.A. et al. (Jul. 2006). "Tissue Engineering of Flexor Tendons: Optimization of Tenocyte Proliferation Using Growth Factor Supplementation," Tissue Eng. 12(7):1937-1943.

(56) References Cited

OTHER PUBLICATIONS

Courneya, J-P. et al. (2010). "Normal and Diseased Primary Human Tenocytes in Response to rhPDGF-BB," Poster No. 1118, 56.sup.th Annual Meeting of the Orhopaedic Research Society, located at <http://www.ors.org/web/Transactions/56/1118.pdf>,last visited on Feb. 23, 2010, 1 page.

Creaney, L. et al. (May 2008, e-pub. Nov. 5, 2007). "Growth Factor Delivery Methods in the Management of Sports Injuries: The State of Play," Br. J. Sports Med. 42(5):314-320, Abstract Only.

Curi et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," Journal of Oral andMaxillofacial Surgery 65(2):349-355.

Dalla-Favera, R. et al. (Nov. 12, 1982). "Chromosomal Localization of the Human Homolog (c-sis) of the Simian Sarcoma Virus one Gene," Science 218:686-688.

Daniels, T.R. et al. (2008). "Application of rhPDGF-BB in Foot and Ankle Fusion Procedures," Chapter 19 in Tissue Engineering: Applications in Maxillofacial Surgery and Periodontics, Second Edition, Lynch. S.E. et al. eds., Quintessence PublishingCo.: Hanover Park, IL, pp. 267-275.

Dines J.S. et al. (Sep./Oct. 2007). "Tissue Engineering and Rotator Cuff Tendon Healing," J. Shoulder Elbow Surg. 16(5S):204S-207S.

Dines, J.S. et al. (Sep./Oct. 2007). "The Effect of Growth on Differentiation Factor-5-Coated Sutures on Tendon Repair in a Rat Model," J. Shoulder Elbow Surg. 16(5S):215S-221S.

Donnelly, B.P. et al. (Jul. 2006). "Nucleotide Structure of Equine Platelet-Derived Growth Factor-A and -B and Expression in Horses with Induced Acute Tendinitis," Am. J. Vet. Res. 67(7):1218-1225, Abstract Only.

Doolittle et al. (Jul. 15, 1983). "Simian Sarcoma Virus one Gene v-sis, Is Derived from the Gene (or Genes) Encoding a Platelet-Derived Growth Factor," Science 221:275-277.

Duffy, F.J. et al. (Jul. 1995). "Growth Factors and Canine Flexor Tendon Healing: Initial Studies in Uninjured and Repair Models," The Journal of Hand Surgery 20A(4):645-649.

Dunn, C.A. et al. (Feb. 2005, e-pub. Nov. 6, 2004). "BMP Gene Delivery for Alveolar Bone Engineering at Dental Implant Defects," Molecular Therapy 11(2):294-299.

Easley, M.E. et al. (May 2000). "Isolated Subtalar Arthodesis," JBJS 82-A(5):613-624.

Eastell, R. et al. (Mar. 1991). "Classification of Vertebral Fractures," J. Bone Miner. Res. 6(3):207-215.

Erikson, A. et al. (Nov. 5, 1991). "Induction of Platelet-Derived Growth Factor .alpha.- and .beta.-Receptor mRNA and Protein by Platelet Derived Growth Factor BB," J. Biol. Chem. 266(31):21138-21144.

Fagan, M.C. et al. (2008). "Simultaneous Augmentation of Hard and Soft Tissues for Implant Site Preparation Using Recombinant Human Platelet-Derived Growth Factor: A Human Case Report," Int. J. Periodontics Restorative Dent. 28(1):37-43.

Farrugia, M.C. et al. (Jan. 2006). "Osteonecrosis of the Mandible or Maxilla Associated with the Use of New Generation Bisphosphonates," The Laryngoscope 116:115-120.

Feldman, D. et al. (Sep. 1998). "In a Time of Change, Orthopedics Sector is Marked by New Modalities," The BBI Newsletter, located at <http://findarticles.eom/p/articles/mi.sub.--m3570/is.sub.--n9.sub.--v-21/ai.sub.--n27541529>, last visitedon Mar. 12, 2009, 2 pages.

Fennis et al. "Mandibular reconstruction: A clinical and radiographic animal study on the use of autogenous scaffolds and platelet-rich plasma," Int. J. Oral Maxillofac. Surg., 2002, 31:281-286.

Fennis, et al., "Mandibular reconstruction: a histological and histomorphometric study on the use of autogeus scaffolds, particulate cortico-cancellous bone grafts and platelet rich plasma in goats," Int. J. Oral Maxillofac. Surg., 2004, 33: 48-55.

Ficarra, G. et al. (2005). "Osteonecrosis of the Jaws in Periodontal Patients with a History of Bisphophonates Treatment," J. Clin. Periodontol. 32:1123-1128.

Finkelman, R.D. et al. (1995). "Systematic PDGF .+-. Alendronate Increases Bone Density in OVX Rats," Abstract No. 1281, J. Dental Res. 74:172.

Fontana et al. "Effect of Platelet-Rich Plasma on the Pert-implant Bone Response: An Experimental Study," Implant Dentistry, 2004, 13:73-78.

Franco, B. et al. (Jan.-Jun. 2008). "Tissue Engineering Approaches for the Construction of a Completely Autologous Tendon Substitute," Indian J. Plast. Surg. 41(1):38-46, 13 pages.

Freedonia (Sep. 2006). "Biocompatible Materials. US Industry Study with Forecasts to 2010 & 2015," Study #2111, located at <http://www.freedoniagroup.com/pdf/2111smwe.pdf>, last visited on Jun. 17, 2010, 8 pages (Table of Contents Only.).

Fribourg, D. et al. (Oct. 15, 2004). "Incidence of Subsequent Vertebral Fracture After Kyphoplasty," Spine 29(20):2270-2276.

Fukui, A. et al. (Sep. 1993). "Isolation and Characterization of Xenopus activin and Follistatin," Devel. Biol. 159(1):131-139.

Galatz, L.M. et al. (Feb. 2004). "The Outcome and Repair Integrity of Completely Arthoscopically Repaired Large and Massive Rotator Cuff Tears," J. Bone Joint Surg. Am. 86-A(2):219-244.

Gamradt, S.C. et al. (Mar. 2007). "Platelet Rich Plasma in Rotator Cuff Repair," Tech, in Orthop. 22(1):26-33.

Garg, "The Use of Platelet-Rich Plasma to Enhance the Success of Bone Grafts Around Dental Implants," Dental Implantology Update, Mar. 2000, 11(3):17-21.

Garg, A.K. (1995). "Grafting Materials in Repair and Restoration," Chapter 5 in Tissue Engineering: Applications in Maxillofacial Surgery and Periodontics, Lynch, S.E. et al. eds., Quintessence Publishing, pp. 83-101.

Gazielly, D.F. et al. (Jul. 1994). "Functional and Anatomical Results After Rotator Cuff Repair," Clin. Orthop. Relat. Res. 304:43-53.

Gelberman, R.H. et al. (Mar. 2007). "The Early Effects of Sustained Platelet-Derived Growth Factor Administration on the Functional and Structural Properties of Repaired Intrasynovial Flexor Tendons: An In Vivo Biomechanic Study at 3 Weeks inCanines," J. Hand Surg. Am. 32A(3):373-379.

Gerber, C. et al. (Apr. 2000). "The Results of Repair of Massive Tears of the Rotator Cuff," J. Bone Joint Surg. Am. 82-A(4):505-515.

Gerber, C. et al. (May 1994). "Mechanical Strength of Repairs of the Rotator Cuff," J. Bone Joint Surg. Br. 76-B(3):371-380.

Giannobile et al. "Comparison of Canine and Non-Human Primate Animal Models for Periodontal Regenerative Therapy: Results Following a Single Administration of PDGF/IGF-I," J. Periodontol., Dec. 1994, 65(12):1158-1168.

Giannobile et al. "Non-Coordinate Control of Bone Formation Displayed by Growth Factor Combinations with IGF-I," J Dent Res, Sep. 1997, 76(9):1569-1578.

Giannobile et al. "Periodontal Tissue Engineering by Growth Factors," Bone, Jul. 1996, 19(1), Supplement: 23S-37S.

Giannobile et al. "Recombinant Human Osteogenic Protein-1 (OP-1) Stimulates Periodontal Wound Healing in Class III Furcation Defects," J Periodontol, Feb. 1998, 69(2):129-137.

Giannobile, "Platelet-Derived Growth Factor (PDGF) Gene Delivery for Application in Periodontal Tissue Engineering," J Periodontol, Jun. 2001, 72(6):815-823.

Giannobile, W.V. (2008). "Advances in Gene Therapy for Periodontal Bioengineering," Chapter 3 in Tissue Engineering: Applications in Maxillofacial Surgery and Periodontics, Second Edition, Lynch. S.E. et al. eds., Quintessence Publishing Co.:Hanover Park, IL, pp. 37-46.

Giannobile, W.V. et al. (1994). "Synergistic Effects of Insulin-Like Growth Factors-I (IGF-I) with Other Growth Factors on Bone Formation in vitro," Abstract No. 831, J. Dental Res. 73:205.

Giannobile, W.V. et al. (Jul. 1996). "Comparative Effects of Platelet-Derived Growth Factor and Insulin-Like Growth Factor-I, Individually and in Combination, on Periodontal Regeneration in Macaca fascicularis," J. Periodontal Res. 31(5):301-312.

Giannobile, W.V. et al. (Nov. 1995). "Platelet Derived Growth Factor (PDGF) and Insulin-Like Growth Factor (IGF-I) Enhances

(56) References Cited

OTHER PUBLICATIONS

Periodontal Regeneration in Macaca fascicularis," Abstract No. 28, Advanced Dental Research 9(3 Suppl.):29.
Giddings, V.L. et al. (2000). "Calcaneal Loading During Walking and Running," Med. Sci. Sports Exerc. 32(3):627-634.
Gilbertson et al. "Platelet-derived Growth Factor C (PDGF-C), a Novel Growth Factor That Binds to PDGF .alpha, and .beta. Receptor," The Journal of Biological Chemistry, Jul. 20, 2001, 276(29):27406-27414.
Goutallier, D. et al. (Jul. 1994). "Fatty Muscle Degeneration in Cuff Ruptures: Pre- and Postoperative Evaluation by CT Scan," Clin. Orthop. 304:78-83.
Grageda, "Platelet-Rich Plasma and Bone Graft Materials: A Review and a Standardized Research Protocol," Implant Dentistry, 2004, 13(4): 301-309.
Green et al. "Immunolocalization of platelet-derived growth factor A and B chains and PDGF-.alpha, and .beta.-receptors in human gingival wounds," Journal of Periodontal Research. 1997, 32(2):209-214.
Gronwald et al. "Cloning and expression of a cDNA coding for the human platelet-derived growth factor receptor: Evidence for more than one receptor class," Proc. Natl. Acad. Sci. USA, May 1988, 85:3435-3439.
Hanel, D.P. et al. (Jan. 2002). "Wrist Fractures," Orthop. Clin. North Am. 33(1):35-57.
Harryman, D.T. et al. (Aug. 1991). "Repairs of the Rotator Cuff," J. Bone Joint Surg. Am. 73-A(7):982-989.
Hart et al. "Synthesis, Phosphorylation, and Degredation of Multiple Forms of the Platelet-derived Growth Factor Receptor Studied Using a Monoclonal Antibody," The Journal of Biological Chemistry, Aug. 5, 1987, 262(22):10780-10785.
Hart et al. "Two Classes of PDGF Receptor Recognize Different Isoforms of PDGF," Science, Jun. 1988, 240:1529-1531.
Hart, C.E. et al. "Purification of PDGF-AB and PDGF-BB from Human Platelet Extracts and Identification of All Three PDGF Dimers in Human Platelets," Biochemistry, Jan. 9, 1990, 29(1):166-172.
Hattrup, S.J. et al. (1985). "A Review of Ruptures of the Achilles Tendon," Foot & Ankle 6(1):34-38.
Hee et al. (2003). "Do Autologous Growth Factors Enhance Transformational Lumbar Interbody Fusion?" Eur. Spine. J. 12(4):400-407.
Heini, P.F. et al. (2001, e-pub. Jun. 14, 2001). "Bone Substitutes in Vertebroplasty," Eur. Spine J. 10:S205-S213.
Helm et al. (Apr. 2001). "Bone Graft Substitutes for the Promotion of Spinal Arthrodesis," Neurosur. Foc. 10(4):1-5.
Hess, G.W. (Feb. 2010). "Achilles Tendon Rupture: A Review of the Etiology, Population, Anatomy, Risk Factors, and Injury Prevention," Foot Ankle Spec. 3(1):29-32.
Higashi, T. et al. (Jun. 1996). "Influence of Particle Size of Calcium Phosphate Ceramics as a Capping Agent on the Formation of a Hard Tissue Barrier in Amputated Dental Pulp," Journal of Endodontics 22(6):281-283.
Hildebrand, K.A. et al. (1998). "The Effects of Platelet-Derived Growth Factor-BB on Healing of the Rabbit Medial Collateral Ligament. An In Vivo Study," American Journal of Sports Medicine 26(4):549-554.
Hoffmann,A et al. (Dec. 2007, e-pub. Jul. 19, 2007). "Tendon and Ligament Engineering in the Adult Organism: Mesenchymal Stem Cells and Gene-Therapeutic Approaches," Int. Orthop. 31(6):791-797.
Hollinger, J.O. et al. (2008). "Protein Therapeutics and Bone Healing," Chapter 1 in Tissue Engineering: Applications in Maxillofacial Surgery and Periodontics, Second Edition, Lynch, S.E. et al. eds., Quintessence Publishing Co.: Hanover Park, IL,pp. 3-25.
Hollinger, J.O. et al. (2008). "Therapeutic Opportunities for Bone Grafting," Chapter 68 in Principles of Regenerative Medicine, Atala, A. et al. eds., Academic Press: Burlington, MA, pp. 1164-1175.

Hollinger, J.O. et al. (Feb. 2008). "Recombinant Human Platelet Derived Growth Factor: Biology and Clinical Applications," J. Bone & Joint Surgery 90-A(Suppl. 1):48-54.
Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," J.Orthopedic Res. 26:83-90.
Hossain, M.Z. et al. (Jul. 1996). "Biological Responses of Autogenous Bone and Beta-Tricalcium Phosphate Ceramics Transplanted into Bone Defects to Orthodontic Forces," Cleft Palate-Craniofacial Journal 33(4):277-283.
Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," J. Periodontol., Dec. 1997,68(12):1186-1193.
Howell, T.H. et al. (1996). "Polypeptide Growth Factors for Periodontal Regeneration," Current Opinion in Periodontology 3:149-156.
Howes et al., "Platelet-Derived Growth Factor Enhances Demineralized Bone Matrix-Induced Cartilage and Bone Formation," Calcif Tissue Int., 1988, 42: 34-38.
Hsu et al. (Jul. 2004). "Clinical Implications of Growth Factors in Flexor Tendon Wound Healing," The Journal of Hand Surgery 29A(4):551-563.
Huang, L-H. et al. "The Effect of Platelet-Rich Plasma on the Coronally Advanced Flap Root Coverage Procedure: A Pilot Human Trial," J. Periodontal, Oct. 2005, 76(10):1768-1777.
Ignotz, R.A. et al. (Mar. 25, 1986). "Transforming Growth Factor-.beta. Simulates the Expression of Fibronectin and Collagen and Their Incorporation in the Extracellular Matrix," J. Biol.Chem. 261(9):4337-4345.
Ikezawa et al., "Characterization of Cementum Derived Growth Factor as an Insulin-Like Growth Factor-I Like Molecule," Connective Tissue Research, 1997, 36(4): 309-319.
Inglis, AE. et al. (Oct. 1976). "Ruptures of the Tendo Achilles: An Objective Assessment of Surgical and Non-Surgical Treatment," J. Bone Joint Surg. 58A(7):990-993.
Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," J. Biomed. Mater. Res. 69A:454-461.
Jensen et al., "Platelet rich plasma and fresh frozen bone allograft as enhancement of implant fixation—An experimental study in dogs," Journal of Orthopaedic Research, 2004, 22: 653-658.
Jensen, O.T. (2008). "Dentoalveolar Modification with an Osteoperiosteal Flap and rhPDGF-BB," Chapter 15 in Tissue Engineering: Applications in Maxillofacial Surgery and Periodontics, Second Edition, Lynch. S.E. et al. eds., Quintessence PublishingCo.: Hanover Park, IL, pp. 220-225.
Jensen, O.T. et al. (2008). "Alveolar Distraction Osteogenesis and Tissue Engineering," Chapter 14 in Tissue Engineering: Applications in Maxillofacial Surgery and Periodontics, Second Edition, Lynch. S.E. et al. eds., Quintessence Publishing Co.:Hanover Park, IL, pp. 203-219.
Jiang, D. et al. "Modification of an Osteoconductive Anorganic Bovine Bone Miami Matrix with Growth Factors," J. Periodonlol., Aug. 1999, 70(8):834-839.
Jin et al. "Engineering of Tooth-Supporting Structures by Delivery of PDGF Gene Therapy Vectors," Molecular Therapy, Apr. 2004, 9(4):519-526.
Jin, Q. et al. (Mar. 5, 2008). "Nanofibrous Scaffolds Incorporating PDGF-BB Microspheres Induce Chemokine Expression and Tissue Neogenesis In Vivo," PLoS ONE 3(3):e1729, pp. 1-9.
Jones et al. (1992). "Isolation of VGR-2, a Novel Member of the Transforming Growth Factor-Beta-related Gene Family," Mol Endocnnol. 6(11):1961-1968.
Jozsa, L. et al. (Aug. 1989). "Fibronectin and Laminin in Achilles Tendon," Acta Orthop Sacninavica 60(4):469-471.
Kademani, D. et al. (Aug. 2006). "Primary Surgical Therapy for Osteonecrosis of the Jaw Secondary to Bisphosphonate Therapy," Mayo Clin. Proc. 81(8):1100-1103.

(56) References Cited

OTHER PUBLICATIONS

Kaigler, "Growth factor delivery for oral and periodontal tissue engineering," Expert Opin Drug Deliv., 2006, 3(5):647-662.
Kapu ci ski, P. et al. (Jul.-Sep. 1996). "An Analgesic Effect of Synthetic Human Calcitonin in Patients with Primary Osteoporosis," The Polish Journal of Medicine and Pharmacy 28(98):83-86.
Kassolis et al. "Alveolar Ridge and Sinus Augmentation Utilizing Platelet-Rich Plasma in Combination with Freeze-Dried Bone Allograft: Case Series," Journal of Periodontology, Oct. 2000, 71(10):1654-1661.
Kazlauskas, et al. Different effects of homo- and heterodimers of platelet-derived growth factor A and B chains on human and mouse fibroblasts, The EMBO Journal (1988) 7 (12): 3727-3735.
Kim et al, "A Comparative Study of Osseointegration of Avana Implants in a Demineralized Freeze-Dried Bone Alone or With Platelet-Rich Plasma," J Oral Maxillofac Surg, 2002, 60:1018-1025.
Kim et al, "Use of Particulate Dentin-Plaster of Paris Combination with/without Platelet-Rich Plasma in the Treatment of Bone Defects Around Implants," The International Journal of Oral & Maxillofacial Implants, 2002; 17:86-94.
Klotzbuecher, C.M. et al. (Apr. 2000). "Patients with Prior Fractures Have an Increased Risk of Future Fractures: A Summary of the Literature and Statistical Synthesis," J. Bone Miner. Res. 15(4):721-739.
Kobayashi, M. et al. (May/Jun. 2006). "Expression of Growth Factors in Early Phase of Supraspinatus Tendon Healing in Rabbits," J. Shoulder Elbow Surg. 15(3):371-377.
Kovacevic, D. et al. (Mar. 2008). "Biological Augmentation of Rotator Cuff Tendon Repair," Clin. Orthop. Relat. Res. 466(3):622-633.
Kovacs et al. "Comparative Study of .beta.-Tricalclum Phosphate Mixed with Platelet-Rich Plasma versus .beta.-Tricalcium Phosphate, A Bone Substitute Material in Dentistry," Acts Veterinaria Hungarica, 2003, 51(4):475-484.
Landesberg et al. "Quantification of Growth Factor Levels Using a Simplified Method of Platelet-Rich Plasma Gel Preparation," J. Oral Maxillofac. Surg., 2000, 58:297-301.
Lasa et al. "Delivery of Demineralized Bone Powder by Fibrin Sealant," Plast. Reconstr. Surg., 1995, 96(6):1409-1417.
Lasa Jr., C. et al. (1996). "Bone Induction by Demineralized Bone Powder and Partially Purified Osteogenin Using a Fibrin-Sealant Carrier," Chapter 14 in Surgical Adhesives and Sealants: Current Technology and Applications, Sierra, D. et al. eds.,Technomic Publishing Company, Inc.: Lancaster, PA, pp. 135-144.
Lee et al., "Enhanced bone formation by controlled growth factor delivery from chitosan-based biomaterials," Journal of Controlled Release, 2002, 78: 187-197.
Lee, S.J. et al. (2001, e-pub. Feb. 13, 2001). "Molded Porous Poly (.sub.L-Lactide) Membranes for Guided Bone Regeneration with Enhanced Effects by Controlled Growth Factor Release," Journal of Biomedical Materials Research 55:295-303.
Lee, Y-M. et al. (Mar. 2000). "The Bone Regenerative Effect of Platelet-Derived Growth Factor-BB Delivered With a Chitosan/ Tricalcium Phosphate Sponge Carrier," J. Periodontal. 71(3):418-424.
Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," J.Periodontol. 73(2):198-205.
Letson, A.K. et al. (1994). "The Effect of Combinations of Growth Factors on Ligament Healing," Clinical Orhopaedics and Related Research 308:207-212.
Li, J. et al. (1994). "Systematic Administration of PDGF With or Without Alendronate Increases Spine and Whole Body Bone Mineral Density in OVX Rats," Abstract No. 59, Sixteenth Annual Meeting of the American Society for Bone and Mineral Research,Kansas City, MO., Sep. 9-13, 1994, p. S135.
Liang et al. (Sep. 2000). "Effect of Cytokines on Repair of Tendon Injury," Pub Med 14(5):283-285, Abstract Only.
Liang, H.W. et al. (Aug. 2009). "Effect of Platelet-Derived Growth Factor-BB on Proliferation of Tendon Cells Cultured in vitro," Zhonghua Shao Shang Za Zhi 25(4):298-300, Abstract Only.
Lind et al. (1998). "Growth Factor Stimulation of Bone Healing," Acta Orthopaedica Scandinavica Supplementum Suppl. 283:2-37.
Lioubavina-Hack et al. "Effect of Bio-Oss.RTM. with or without platelet-derived growth factor on bone formation by 'guided tissue regeneration': a pilot study in rats," J Clin. Periodontol, 2005, 32(12):1254-1260.
Lioubavina-Hack et al., "Methyl cellulose gel obstructed bone formation by GBR: an experimental study in rats," J. Clin. Periodontol., 2005, 32:1247-1253.
Lipshitz, H. et al. (Jun. 1975). "In Vitro Wear of Cartilage," J. Bone Joint Surg. Am. 57A(4):527-534.
Lynch, S.E. (1990). "A Possible Role for Polypeptide Growth and Differentiation Factors in Periodontal Regeneration," Executive Committee on Chemotherpeutics; Amer. Acad Peridontal—Position Paper pp. 1-4.
Lynch, S.E. (1991). "Platelet-Derived Growth Factor and Insulin-Like Growth Factor. I: Mediators of Healing Soft Tissue and Bone Wounds," Periodontol Case Reports NE Soc. Periodontists Bull. 13(2):13-20.
Lynch, S.E. (1993). "Comparison of Results in the Canine and Primate Models Using a Single Regenerative Therapy," Abstract No. 37, J. Dental Res. 72:108.
Lynch, S.E. (1994). "The Role of Growth Factors in Periodontal Repair and Regeneration," Chapter 11 in Periodontal Regeneration: Current Status and Directions, Poison, A. ed. Quintessence Publishing Co, Inc: Chicago, IL, 11:179-197.
Lynch, S.E. (1995). "Introduction," in Tissue Engineering: Applications in Maxillofacial Surgery and Preiodontics, Lynch, S.E. et al. eds., Quintessence Publishing, pp. xi-xvi.
Lynch, S.E. (2005). "Bone Regeneration Techniques in the Orofacial Region," Chapter 18 in Bone Regeneration and Repair: Biology and Clinical Applications, Lieberman, J.R. et al. eds., Humana Press Inc.: Totowa, NJ, pp. 359-390.
Lynch, S.E. et al. (1988). "Potential Role of Platelet-Derived and Insulin-Like Growth Factors in Periodontal Regeneration," Abstract No. 586, J. Dental Res. 67:186.
Lynch, S.E. et al. (1988). "Synergistic Effects of Recombinant Platelet-Derived Growth Factor Two and Insulin-Like Growth Factor-I in Wound Healing," Abstract No. 585, J. Dental Res. 67:186.
Lynch, S.E. et al. (1989). "A Combination of Platelet-Derived and Insulin-Like Growth Factors Enhances Periodontal Regeneration," J. Clin. Periodontol. 16:545-548.
Lynch, S.E. et al. (1989). "Comparative Effects of Growth Factors on Soft Tissue Repair," Abstract No. 1153, J. Dental Res. 68:326.
Lynch, S.E. et al. (1992). "Effect of PDGF-B and IGF-I on Bone Regeneration," Abstract No. 82, J. Dental Res. 71:116.
Lynch, S.E. et al. (1994). "Polypeptide Growth Factors: Molecular Mediators of Tissue Repair," Chapter 33 in Molecular Pathogenesis of Periodontal Disease, Genco, R. et al. eds., A.S.M. Press: Washington DC, pp. 415-425.
Lynch, S.E. et al. (2008). "Use of rhPDGF to Improve Bone and Periodontal Regeneration," Chapter 6 in Tissue Engineering: Applications in Maxillofacial Surgery and Periodontics, Second Edition, Lynch. S.E. et al. eds., Quintessence Publishing Co.:Hanover Park, IL, pp. 87-102.
Lynch, S.E. et al. (Dec. 1988). "Growth Factors in Wound Healing: Single and Synergistic Effects," Abstract No. 238, J. Cell Biol. 107(6 Part 3):46a.
Lynch, S.E. et al. (Dec. 2006). "A New Era in Periodontal and Periimplant Regeneration: Use of Growth-Factor Enhanced Matrices Incorporating rhPDGF," Compendium of Continuing Education in Dentistry 27(12):672-679.
Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," Wound Repair and Regeneration Abstract, 2(1):84.
Lynch, S.E. et al. (Jul. 1991). "The Effects of Short Term Application of a Combination of Platelet-Derived and Insulin-Like Growth Factors on Periodontal Wound Healing," J. Periodontol. 62(7):458-467.

(56) References Cited

OTHER PUBLICATIONS

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," Wound Rep. Reg. 2(3):182-190.
Lynch, S.E. et al. (Nov. 1987). "Role of Platelet-Derived Growth Factor in Wound Healing: Synergistic Effects with Other Growth Factors," Proc. Natl. Acad. Sci. USA 84:7696-7700.
Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," J. Periodontol. 62(11):710-717.
Maffulli, N. et al. (2002). "Tendon Healing: Can It Be Optimized?" British Journal of Sports Medicine 36:315-316.
Maffulli, N. et al. (2003). "Types and Epidemiology of Tendinopathy," Clinics in Sports Medicine 22:675-692.
Maiorana et al. "Maxillary Sinus Augmentation with Anorganic Bovine Bone (Bio-Oss) and Autologous Platelet-Rich Plasma: Preliminary Clinical and Histologic Evaluations," Int J Periodontics Restorative Den, 2003, 23(3):227-235.
Manske et al. (Feb. 1985). "Flexor Tendon Healing," Symposium on Flexor Tendon Surgery, Hand Clinics 1(1):25-34.
Marcopoulou et al. (2003). "Proliferative Effect of Growth Factors TGF-.beta.1, PDGF-BB, and rhBMP-2 on Human Gingival Fibroblasts and Periodontal Ligament Cells," Journal of International Academy of Periodontology 5(3):63-70.
Marx, R.E. (2008). "Application of Tissue Engineering Principles to Clinical Practice," Chapter 4 in Tissue Engineering: Applications in Maxillofacial Surgery and Periodontics, Second Edition, Lynch, S.E. et al. eds., Quintessence Publishing Co.:Hanover Park, IL, pp. 47-63.
Marx, R.E. (2008). "Use of PRP in Oral and Maxillofacial Surgery and Periodontology," Chapter 9 in Tissue Engineering: Applications in Maxillofacial Surgery and Periodontics, Second Edition, Lynch. S.E. et al. eds., Quintessence Publishing Co.:Hanover Park, IL, pp. 132-144.
Marx, R.E. et al. (2005). "Bisphosphonate-Induced Exposed Bone (Osteonecrosis/Osteoperosis) of the Jaws: Risk Factors, Recognition, Prevention, and Treatment," J. Oral Maxillofac. Surg. 63:1567-1575.
Mayfield, L. et al. (Oct. 1998). "Clinical and Radiographic Evaluation, Following Delivery of Fixed Reconstructions, at GBR Treated Titanium Fixtures," Clin. Oral Implants Res. 9:292-302.
McAllister et al. "Eighteen-month Radiographic and Histologic Evaluation of Sinus Grafting with Anorganic Bovine Bone in the Chimpanzee," The International Journal of Oral & Maxillofacial Implants, 1999, 14(3):361-368.
McAllister, B. et al. (1998). "Long-term Evaluation of Sinus Grafting with Bio-Oss.RTM. in the Chimpanzee," Abstract No. 1097, J. Dental Res. 77:769.
McCarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," J. Orthop. Res.27(8):1033-1042, Abstract Only.
McGuire, M.K. (2008). "Soft Tissue Engineering Applications in Dentistry," Chapter 7 in Tissue Engineering: Applications in Maxillofacial Surgery and Periodontics, Second Edition, Lynch, S.E. et al. eds., Quintessence Publishing Co.: Hanover Park,IL, pp. 103-118.
McGuire, M.K. et al. (2006). "rhPDGF-BB Promotes Healing of Periodontal Defects: 24-Month Clinical and Radiographic Observations," Int. J. Periodontics Restorative Dent. 26(3):223-231.
McMurty, R.Y. et al. (1992). "Fractures of the Distal Radius," Chapter 35 in Skeletal Trauma, Browner B.D. et al. eds., W.B. Saunders Company: Philadelphia, PA, 2:1063-1094.
Mehta, V. et al. (Apr.-Jun. 2005). "The Use of Growth Factors on Tendon Injuries," Journal of Hand Therapy 18:87-92.
Melo, M.D. et al. (Dec. 2005). "Osteonecrosis of the Jaws in Patients with a History of Receiving Bisphosphonate Therapy. Strategies for Prevention and Early Recognition," J. American Dental Association 136:16751681.
Migliorati, C.A. et al. (Jun. 2006). "Bisphosphate-Associated Osteonecrosis: A Long Term Complication of Bisphophonate Treatment," Lancet Oncol. 7:508-514.
Millette, E. et al. (2006). "Platelet-Derived Growth Factor-BB Transactivates the Fibroblast Growth Factor Receptor to Induce Proliferation in Human Smooth Muscle Cells," Trends Cardiov. Med. 16(1):25-28.
Mitlak et al., "The Effect of Systemically Administered PDGF-BB on the Rodent Skeleton," Journal of Bone and Mineral Research, 1996, 11(2): 238-247.
Molloy, T. et al. (2003). "The Roles of Growth Factors in Tendon and Ligament Healing," Sports Med. 33(5):381-394.
Mont, M.A. et al. (Oct. 1998). "Osteonecrosis of the Femoral Head. Potential Treatment with Growth and Differentiation Factors," Clin. Orthop. Relat. Res. 355(Suppl.):S314-S335, Abstract Only, 2 pages.
Morris, G.J. et al. (Jan. 2007). "Bisphosphonate Therapy for Women with Breast Cancer and at High Risk for Osteoporosis," Journal of the National Medical Association 99(1):35-45.
Mott, D.A. et al. (2002). "Enhancement of Osteoblast Proliferation in vitro by Selective Enrichment of Demineralized Freeze-Dried Bone Allograft with Specific Growth Factors," J. Oral Implantol. 28(2):57-66.
Mumford, J.H. et al. (Mar. 2001). "The Effects of Platelet Derived Growth Factor-BB on Periodontal Cells in In Vitro Wound Model," J. Periodontal. 72(3):331-340.
Nakamura, N. et al. (1998). "Early Biological Effect of In Vivo Gene Transfer of Platelet-derived Grown Factor (PDGF)-B into Healing Patellar Ligament," Gene Therapy 5:1165-1170.
Nancollas, G.H. et al. (2006, e-pub. Jul. 20, 2005). "Novel Insights into Actions of Bisphosphonates on Bone: Differences in Interactions with Hydrozyapatite," Bone 38:617-627.
Nase, J.B. et al. (Aug. 2006). "Osteonecrosis of the Jaw and Oral Bisphosphonate Treatment," J. American Dental Association 137:1115-1119.
Nash, T.J. et al. (Mar. 1994). "Effect of Platelet-Derived Growth Factor on Tibial Osteotomies in Rabbits," Bone 15(2):203-208.
Nevins et al. "Periodontal Regeneration in Humans Using Recombinant Human Platelet-derived Growth Factor-BB (rhPDGF-BB) and Allogenic Bone," J. Periodontal, Sep. 2003, 74(9):1282-1292.
Nevins et al. "Platelet-Derived Growth Factor Stimulates Bone Fill and Rate of Attachment Level Gain: Results of a Large Multicenter Randomized Controlled Trial," J. Periodontal, Dec. 2005, 76(12):2205-2215.
Nevins, M. et al. (2008). "Treatment of Advanced Periodontal Defects Using Bioactive Therapies," Chapter 5 in Tissue Engineering: Applications in Maxillofacial Surgery and Periodontics, Second Edition, Lynch, S.E. et al. eds., QuintessencePublishing Co.: Hanover Park, IL, pp. 67-86.
Nevins, M. et al. (Oct. 2007). "Clinical Results Using Recombinant Human Platelet-Derived Growth Factor and Mineralized Freeze-Dried Bone Allograft in Periodontal Defects," Int. J. Periodontics Restorative Dent. 27(5):421-427.
Nevins, M.L. et al. (2003). "Evaluation of Periodontal Regeneration Following Grafting Intrabony Defects with Bio-Oss.RTM. Collagen: A Human Histologic Report," Int. J. Periodont. Rest. Dent. 23(1):9-17.
Nevins, M.L. et al. (2005). "Three-Dimensional Micro-Computed Tomographic Evaluation of Periodontal Regeneration: A Human Report of Intrabony Defects Treated with Bio-Oss Collagen," Int. J. Periodontics Restorative Dent. 25(4):365-373.
Nevins, M.L. et al. (2008). "Site Development for Implant Placement: Regenerative and Esthetic Techniques in Oral Plastic Surgery," Chapter 8 in Tissue Engineering: Applications in Maxillofacial Surgery and Periodontics, Second Edition, Lynch, S.E.et al. eds., Quintessence Publishing Co.: Hanover Park, IL, pp. 119-131.
Nickols, J.C. et al. (2008). "The Role of Growth Factors in Tendon Healing," Chapter 20 in Tissue Engineering: Applications in Maxillofacial Surgery and Periodontics, Second Edition, Lynch, S.E. et al. eds., Quintessence Publishing Co.: HanoverPark, IL, pp. 276-289.

(56) References Cited

OTHER PUBLICATIONS

Nistor, L. (Mar. 1981). "Surgical and Non-Surgical Treatment of Achilles Tendon Rupture: A Prospective Randomized Study," J. Bone Joint Surg Am. 63A(3):394-399.
Nociti, F.H. Jr. et al. (2000). "Histometric Evaluation of Bone Regeneration Around Immediate Implants Partially in Contact with Bone: A Pilot Study in Dogs," Implant Dentistry 9(4):321-328.
Oberg, S. et al. (Apr. 1994). "Bone Healing After Implantation of Hydroxyapatite Granules and Blocks (Interpore 200) Combined with Autolyzed Antigen-Extracted Allogeneic Bone and Fibrin Glue. Experimental Studies on Adult Rabbits," InternationalJournal of Oral and Maxillofacial Surgery 23(2):110-114, abstract only.
Orbay, J.L. et al. (Jan. 2004). "Volar Fixed-Angle Plate Fixation for Unstable Distal Radius Fractures in the Elderly Patient," J. Hand Surg. 29A(1):96-102.
Orthovita, Inc. (2009). "Architects of the New Biomaterials Age, 2008 Annual Report," located at <http://orthovita.com/investors/annual-reports/previousreports.aspx>-;, last visited on Jun. 17, 2010, 93 pages.
Orthovita, Inc. (Dec. 14, 2000). "510(k) Summary. Vitoss.TM. Scaffold Syntehtic Cancellous Bone Void Filler," located at <http://www.accessdata.fda.gov/cdrh.sub.--docs/pdf/k994337.pdf>, last visited on Mar. 30, 2010, 6 pages.
Orthovita, Inc. (Nov. 19, 2002). "Morningstar.RTM. Document Research.TM.. Form 10-Q, Quarterly Repot Which Provides a Continuing View of a Company's Financial Position," located at <http://orthovita.com/investors/secfilings.aspx>, last visitedon Jun. 17, 2010, 48 pages.
Owen et al. (1984). "Simian Sarcoma Virus-Transformed Cells Secrete a Mitogen Identical to Platelet-Derived Growth factor," Science 25:54-56.
Palti, A. et al. (2002). "A Concept for the Treatment of Various Dental Bone Defects," Implant Dentistry 11(1):73-78.
Parashis, A. et al. (Jul. 1998). "Comparison of 2 Regenerative Procedures-Guided Tissue Regeneration and Demineralized Freeze-Dried Bone Allograft—in the Treatment of Intrabony Defects: A Clinical and Radiographic Study," J. Periodontol.69(7):751-758.
Park et al. (Jun. 1995). "Periodontal Regeneration in Class III Furcation Defects of Beagle Dogs Using Guided Tissue Regenerative Therapy with Platelet-Derived Growth Factor," J. Periodontol. 66:462-477.
Paul, W. et al. (1999). "Development of Porous Spherical Hydroxyapatite Granules: Application Towards Protein Delivery," J. Mater. Sci. Mater. Med. 10:383-388.
Persson, G.R. et al. (2000). "A Retrospective Radiographic Outcome Assessment Study of Intra-Bony Defects Treated by Osseous Surgery or by Bone Graft Procedures," J. Clin. Periodontol. 27:104-108.
Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts," Arch. Orthop. TraumaSurg. 123(9):485-488.
Pfeilschifter, J. et al. (Jul.-Dec. 1990). "Stimulation of Bone Matrix Apposition in Vitro by Local Growth Factors: A Comparison Between Insulin-Like Growth Factor I, Platelet Derived Growth Factor, and Transforming Growth Factor .beta.," Endocrinology 127(1):69-75.
Philippart et al. "Human Recombinant Tissue Factor, Platelet-rich Plasma, and Tetracycline Induce a High-Quality Human Bone Graft a 5-year Survey," The International Journal of Oral and Maxillofacial Implants, 2003, 18(3):411-416.
Phillips, S. et al. (1988). "The Direct Medical Costs of Osteoporosis for American Woman Aged 45 and Older, 1986," Bone 9(4):271-279.
Pickett, F.A. (Jul. 2006). "Bisphosphonate-Associated Osteonecrosis of the Jaw: A Literature Review and Clinical Practice Guidelines," Journal of Dental Hygiene 80(3):1-12.

Pietrzak, W.S. et al. (Jul. 2000). "Calcium Sulfate Bone Void Filler: A Review and a Look Ahead," J. Craniofac. Surg. 11 (4):327-333; discussion p. 334.
Polverini, P.J. (Aug. 2002). "Angiogenesis in Health and Disease: Insights into Basic Mechanisms and Therapeutic Opportunities," Journal of Dental Education 66(8):962-975.
Premdas, J. et al. (2001). "The Presence of Smooth Muscle Action in Fibroblasts in the Torn Human Rotator Cuff," Journal of Orthopaedic Research 19:221-228.
Qiu, Y. et al. (2009). "Combination of PDGF-BB and bFGF Reduces Differentiation but Maintains Proliferation of Human Tenocytes in Low Bovine Serum Culture in vitro," European Cells and Materials 18(Suppl. 2):86.
Qu, Z. et al. (Nov. 1994). "Immunolocalization of Basic Fibroblast Growth Factor and Platelet-Derived Growth Factor-A During Adjuvant Arthritis in the Lewis Rat," Am. J. Pathol. 145(5):1127-1139.
Rao, C.D. et al. (Apr. 1986). "Structure and Sequence of the Human c-sis/Platelet-Derived Growth Factor 2 (SIS/PDGF2) Transcriptional Unit," Proc. Natl. Acad. Sci. USA 83:2392-2396.
Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," Int. J. Mol. Med. 23(3):407-413, Abstract Only, 2 pages.
Rasubala, L. et al. "Platelet-derived Growth Factor and Bone Morphogenetic Protein in the Healing of Mandibular Fractures in Rats," British Journal of Oral and Maxillofacial Surgery, 2003, 41:173-178.
Rettig, A.C. et al. (2005). "Potential Risk of Rerupture in Primary Achilles Tendon Repair in Athletes Younger Than 30 Years of Age," Am. J. Sports Med. 33(1):119-123.
Rickert, M. et al. (2001). "A Growth and Differentiation Factor-5 (GDF-5)-Coated Suture Stimulates Tendon Healing in an Achilles Tendon Model in Rats," Growth Factors 19:115-126.
Riley, G. (2004, e-pub. Jul. 16, 2003). "The Pathogenesis of Tendinopathy. A Molecular Perspective," Rheumatology 43(2):131-142.
Robbins, K.C. et al. (Oct. 13, 1983). "Structural and Immunological Similarities Between Simian Sarcoma Virus Gene Product(s) and Human Platelet-Derived Growth Factor," Nature 305:605-608.
Rodeo, S.A. et al. (1999). "Use of Recombinant Human Bone Morphogenic Protein-2 to Enhance Tendon Healing in a Bone Tunnel," Am. J. Sports Med. 27(4):476-488.
Rodeo, S.A. et al. (Dec. 1993). "Tendon Healing in a Bone Tunnel," J. Bone Joint Surg. Am. 75-A(12):1795-1803.
Rodriguez et al. "Maxillary Sinus Augmentation with Deproteinated Bovine Bone and Platelet Rich Plasma with Simultaneous Insertion of Endosseous Implants," J. Oral Maxiilofac. Surg., 2003, 61:157-163.
Rohrich et al. (Nov. 1999). "Mersilene Suture as a Vehicle for Delivery of Growth Factors in Tendon Repair," Journal of the American Society of Plastic Surgeons 104(6):1713-1717.
Rolf, C.G. et al. (2001). "Increased Cell Proliferation and Associated Expression of PDGFR.beta. Causing Hypercellularity in Patellar Tendinosis," Rheumatology 40:256-261.
Ruggiero, S.L. et al. (2006, e-pub. Jul. 31, 2006). "Bisphosphonate-Related Osteoncerosis of the Jaw: Background and Guidelines for Diagnosis, Staging and Management," Oral Surgery, Oral Medicine, Oral Pathology, Oral Radiology, and Endodontology<http://www.sciencedirect.com/science/journal/10792104>, 8 pages.
Ruiz, G. et al. (1991). "Short Term Administration of Growth Factors Enhances Periodontal Regeneration," Abstract No. 1615, J. Dental Res. 70:468.
Rutherford et al. (1992). "Platelet-Derived and Insulin-Like Growth Factors Stimulate Regeneration of Periodontal Attachment in Monkeys," Journal of Periodontal Research 27(4-Part 1):285-290.
Sakiyama-Elbert, S.E. et al. (Nov. 2008). "Controlled-Release Kinetics and Biologic Activity of Platelet-Derived Growth Factor-BB for Use in Flexor Tendon Repair," J. Hand Surg. Am. 33(9):1548-1557, Abstract Only.
Sandberg, "Matrix in Cartilage and Bone Development Current Views on the Function and Regulation of Major Organic Components," Annals of Medicine, 1991, 23: 207-217.

(56) References Cited

OTHER PUBLICATIONS

Sarment, D.P. et al. (Feb. 1, 2006). "Effect of rhPDGF-BB on Bone Turnover During Periodontal Repair," Journal of Clinical Periodontolgy 33(2):135-140.
Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," Clin. Oral Implants Res. 14(3):369-372.
Sasai, Y. et al. (Dec. 2, 1994). "Xenopus chordin: A Novel Dorsalizing Factor Activated by Organizer-Specific Homeobox Genes," Cell 79:779-790.
Saygin et al., "Molecular and Cell Biology of Cementum," Periodontology, 2000, 24: 73-98.
Schenk, R.K. et al. (Jan./Feb. 1994). "Healing Pattern of Bone Regeneration in Membrane-Protected Defects: A Histologic Study in the Canine Mandible," Int. J. Oral Maxillofac. Implants 9(1):13-29.
Schmidt et al. "A review of the effects of insulin-like growth factor and platelet derived growth factor on in vivo cartilage healing and repair," Osteoarthritis and Cartilage, 2006, 14(5):403-412.
Schmidt, C.C. et al. (Mar. 1995). "Effect of Growth Factors on the Proliferation of Fibroblasts from the Medial Collateral and Anterior Cruciate Ligaments," J. Orthop. Res. 13(2):184-190, Abstract Only.
Schmidt, M.B. et al. (2008). "Tissue Engineering Strategies in the Treatment of TMDs," Chapter 18 in Tissue Engineering: Applications in Maxillofacial Surgery and Periodontics, Second Edition, Lynch, S.E. et al. eds., Quintessence Publishing Co.:Hanover Park, IL, pp. 252-264.
Schmitt, J.M. et al. (Nov. 1997). "Comparison of Porous Bone Mineral and Biologically Active Glass in Critical-Sized Defects," J. Periodontol. 68(11):1043-1053.
Schnabel, L.V. et al. (Feb. 2007). "Platelet Rich Plasma (PRP) Enhances Anabolic Gene Expression Patterns in Flexor Digitorum Superficialis Tendons," J. Orthop. Res. 25(2):230-240, Abstract Only.
secinfo.com (Mar. 31, 2003). "Interpore International Inc/DE 10-K for Dec. 31, 2002," located at <http://www.secinfo.com/dV179.2kp.htm, last visited on May 20, 2010, 57 pages.
Seeherman, H.J. et al. (Oct. 2008). "rhBMP-12 Accelerates Healing of Rotator Cuff Repairs in Sheep Model," J. Bone Joint Surg. Am. 90A(10):2206-2219.
Shahgaldi, B.F. et al. (Jan. 1991). "Repair of Cartilage Lesions Using Biological Implants. A Comparative Histological and Biomechanical Study in Goats," J. Bone Joint Surg. Br. 73-B(1):57-64.
Sharma, P. et al. (2008). "Tendinopathy and Tendon Injury: The Future," Disability and Rehabilitation 30(20-22):1733-1745.
Simion, M. et al. (1994). "Vertical Ridge Augmentation Using a Membrane Technique Associated with Osseointegrated Implants," Int. J. Periodontics Restorative Dent. 14(6):497-511.
Simion, M. et al. (1995). "Bacterial Penetration in vitro Through GTAM Membrane With and Without Topical Chlorhexidine Application: A Light and Scanning Electron Microscopic Study," J. Clin. Periodontol. 22:321-331.
Simion, M. et al. (1999). "Effect of Different Microstructures of e-PTFE Membranes on Bone Regeneration and Soft Tissue Response: A Histologic Study in Canine Mandible," Clin. Oral Implants Res. 10:73-84.
Simion, M. et al. (2008). "Minimally Invasive Strategies for Vertical Ridge Augmentation," Chapter 10 in Tissue Engineering: Applications in Maxillofacial Surgery and Periodontics, Second Edition, Lynch. S.E. et al. eds., Quintessence PublishingCo.: Hanover Park, IL, pp. 145-158.
Simion, M. et al. (Apr. 1994). "A Comparative Study of the Effectiveness of e-PTFE Membranes With and Without Early Exposure During the Healing Period," Int. J. Periodontics Restorative Dent. 14(2):166-180.
Simion, M. et al. (Feb. 1998). "Vertical Ridge Augmentation Around Dental Implants Using a Membrane Technique and Autogenous Bone or Allografts in Humans," Int. J. Periodontics Restorative Dent. 18(1):9-23.
Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," The International Journal of Periodontics &Restorative Dentistry 26(5):415-423.
Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," Mayo Clin. Proc. 81(8):1013-1022.
Sode, J. et al. (May 2007, e-pub. Mar. 3, 2007). "Use of Fluroquinolone and Risk of Achilles Tendon Rupture: A Population-based Cohort Study," Eur. J. Clin. Pharmacol. 63(5):499-503.
Solheim, E. "Growth Factors in Bone," International Orthopedics (SICOT), 1998, 22:410-416.
Spector, M. (2008). "Basic Principles of Scaffolds in Tissue Engineering," Chapter 2 in Tissue Engineering: Applications in Maxillofacial Surgery and Periodontics, Second Edition, Lynch, S.E. et al. eds., Quintessence Publishing Co.: Hanover Park,IL, pp. 26-36.
Spindler, K.P. et al. (1995). "Proliferative Response to Platelet-Derived Growth Factor in Young and Old Rat Patellar Tendon," Connective Tissue Research 31(2):171-177.
Spindler, K.P. et al. (Jul. 1996). "Patellar Tendon and Anterior Cruciate Ligament Have Different Mitogenic Responses to Platelet-Derived Growth Factor and Transforming Growth Factor .beta.," Journal of Orthopaedic Research 14(4):542-546.
Stephan et al. "Platelet-Derived Growth Factor Enhancement of a Mineral-Collagen Bone Substitute," J. Periodontal, Dec. 2000, 71:1887-1892.
Stephan, E.B. et al. (Apr. 1999). "Anogranic Bovine Bone Supports Osteoblastic Cell Attachment and Proliferation," J. Periodontol. 70(4):364-369.
Strom, T.B. (Sep. 6, 2005). "Saving Islets from Allograft Rejection," PNAS USA 102(36):12651-12652.
Suba et al. "Facilitation of .beta.-Tricalcium Phosphate-Induced Alveolar Bone Regeneration by Platelet-Rich Plasma in Beage Dogs: A Histologic and Histomorphometric Study," The International J. of Oral and Maxillofacial Implants, 2004,19(6):832-838.
Tadic, D. et al. (2004). "A Novel Method to Produce Hydroxyapatite Objects with Interconnecting Porosity that Avoids Sintering," Biomaterials 25(16):3335-3340.
Tamai, N. et al. (2002). "Novel Hydroxyapatite Ceramics with an Interconnective Porous Structure Exhibit Superior Osteoconduction in vivo," J. Biomed. Mater. Res. 59:110-117.
Teraoka, K. et al. (2004). "Construction of an Interconnected Pore Network Using Hydroxyapatite Beads," Key. Eng. Mater. 254-256:257-259.
Teraoka, K. et al. (Sep. 2004). "Construction of Interconnected Pore Network Using Hydroxyapatite Small Components," Trans. Mater. Res. Soc. Jpn. 29(6):2919-2921.
Thomopoulos, S. et al. (Feb. 2010, e-pub. Nov. 24, 2009). "bFGF and PDGF-BB for Tendon Repair: Controlled Release and Biologic Activity by Tendon Fibroblasts In Vitro," Ann. Biomed. Eng. 38(2):225-234.
Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," J. Orthop. Res. 25(17):1358-1368.
Thomopoulos, S. et al. (Sep. 2009, e-pub. Mar. 25, 2009). "Enhanced Flexor Tendon Healing through Controlled Delivery of PDGF-BB," J. Orthop. Res. 27(9):1209-1215.
Thompoulos, S. et al. (May 2005). "Effect of Several Growth Factors on Canine Flexor Tendon Fibroblast Proliferation and Collagen Synthesis in vitro," J. Hand Surg. Am. 30(3):441-447, Abstract Only.
Tinti, C. et al. (1996). "Vertical Ridge Augmentation: What is the Limit?" Int. J. Periodontics Restorative Dent. 16(3):221-229.
Uggen, C. et al. (2010). "The Effect of Recombinant Human Platelet Derived Growth Factor BB-Coated Sutures on Rotator Cuff Healing in a Sheep Model," Arthroscopy 26(11):1456-1462.
Uggen, J.C. et al. (Jan. 2005). "Tendon Gene Therapy Modulates the Local Repair Enviornment in the Shoulder," J. Am. Osteopath. Assoc. 105(1):20-21.

(56) References Cited

OTHER PUBLICATIONS

Van Den Wyngaert, T. et al. (Aug. 2006). "Bisphosphonates and Osteonecrosis of the Jaw: Cause and Effect or a post hoc Fallacy?" Annals of Oncology 17(8):1197-1204.

Venkatasatya, M. et al. (2008). The Effect of PDGF, Vitamin D and PTH on Osteoblasts Derived From Patients on Chronic Bisphosphonate Therapy, Dissertation for The State University of New York at Buffalo, located at<http://gradworks.umi.com/14/531/1453440.html>, last visited on Mar. 31, 2010, 2 pages, Abstract Only.

Virchenko, O. et al. (2008, e-pub. Jul. 4, 2008). "Early Achilles Tendon Healing in Sheep," Arch. Orthop. Trauma Surg. 128:1001-1006.

Visnapuu et al. "Distribution of fibroblast growth factors (FGFR-1 and -3) and platelet-derived growth factor receptors (PDGFR) in the rat mandibular condyle during growth," Orthod. Craniofadal. 2002, 5:147-153.

Walter, C. et al. (2006, e-pub. Aug. 29, 2006). "Prevalence of Bisphophonate Associated Osteonecrosis of the Jaw within the Filed of Osteonecrosis," Support Care Center 6 pages.

Wang, L. et al. (2004). "Three-Dimensional Porous Network Structure Developed in Hydroxyapatite-Based Nanocomposites Containing Enzyme Pretreated Silk Fibronin," J. Nanopart. 6(1):91-98.

Wang, X.T. et al. (Sep. 2004). "Tendon Healing In Vitro: Genetic Modification of Tenocytes With Exogenous PDGF Gene and Promotion of Collagen Gene Expression," The Journal of Hand Surgery 29A(5):884-890.

Wang, Y. et al. (Feb. 23, 1996). "A Large Family of Putative Transmembrane Receptors Homologous to the Product of the *Drosophila* Tissue Polarity Gene Frizzled," J. Biol. Chem. 271(8):4468-4476.

Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," J. Bone Joint Surg. Am.74-A(1):36-45.

Wei et al. "Nano-Fibrous Scaffold for Controlled Delivery of Recombinant Human PDGF-BB," Journal of Controlled Release, 2006, e-pub. Mar. 3, 2006, 112:103-110.

Weiler, A. et al. (2004). "The Influence of Locally Applied Platelet-Derived Growth Factor-BB on Free Tendon Graft Remodeling After Anterior Cruciate Ligament Reconstruction," Am. J. Sports Med. 32(4):881-891.

White, E. et al. (1986). "Biomaterial Aspects of lnterpore-200 Porous Hydroxyapatite," Dent. Clin. North Am. 30(1):49-67, Abstract only.

Wiesen, R.J. et al. (1998). "Efficacy of Bovine Bone Mineral in Vertical Osseous Defects," Abstract No. 1165, J. Dental Res. 77:777.

Wikesjo et al. (1988). "Repair of Periodontal Furcation Defects in Beagle Dogs Following Reconstructive Surgery Including Root Surface Demineralization with Tetracycline Hydrochloride and Topical Fibronectin Application," J. Clin. Periodontol15:73-79.

Wikesjo et al. (1989). "Effects of Subgingival Irrigation on A. actinomycetemcomitans," J. Clin. Perrodont. 16:116-119.

Williams et al. "Tissue Engineering: What Does It Mean? Why Is It Important?" Compendium, Jan. 2005, 26(1):54-60.

Wisner-Lynch, L.A. (Oct. 2006). "From Passive to Active: Will Recombinant Growth Factor Therapeutics Revolutionize Regeneration?" Int. J. Periodont. and Rest. Dent. 26(5):409-411.

Wong, M.W. et al. (Oct. 2003). "Effect of Dexamethasone on Cultured Human Tenocytes and its Reversibility by Platelet-Derived Growth Factor," Journal of Bone and Joint Surgery American 85-A(10)1914-1920, Abstract Only.

Woo, S-B. et al. (May 16, 2006). "Systematic Review: Bisphosphonates and Osteonecrosis of the Jaws," Annals of Internal Medicine 144(10):753-761.

Woo, S.L-Y. et al. (1998). "Engineering the Healing of the Rabbit Medical Collateral Ligament," Medical and Biological Engineering and Computing 36:359-364.

Yang, C. et al. (2003). "Vascular Endothelial Growth Factor Gene Transfection to Enhance the Repair of Avascular Necrosis of the Femoral Head of Rabbit," Chinese Medical Journal 116(10):1544-1548.

Yazawa et al, "Basic Studies on the Clinical Applications of Platelet-Rich Plasma," Cell Transplantation, 2003, 12: 509-518.

Yazawa, M. et al. (May 2004). "Basic Studies on the Bone Formation Ability by Platelet Rich Plasma in Rabbits," Journal of Craniofacial Surgery 15(3):439-446.

Yokota, K. et al. (2008, e-pub. Feb. 1, 2008). "Platelet-Rich Plasma Accelerated Surgical Angio-Genesis in Vascular Necrotic Bone. An Experimental Study in Rabbits," Acta Orhopaedica 79(1):106-110.

Younger, E.M. et al. (1989). "Morbidity at Bone Graft Donor Sites," J. Orthop. Trauma 3(3):192-195.

Zavras, A.I. et al. (2006). "Bisphosphonates Are Associated With Increased Risk for Jaw Surgery in Medical Claims Data: Is it Osteonecrosis?" J. Oral Maxillofac. Surg. 64:917-923.

Zhu et al., "Gene Transfer and Expression of Platelet-Derived Growth Factors Modulate Periodontal Cellular Activity," J. Dent Res, 2001, 80(3):892-897.

\* cited by examiner

PLATELET-DERIVED GROWTH FACTOR COMPOSITIONS AND METHODS FOR THE TREATMENT OF TENDINOPATHIES

CROSS REFERENCE TO RELATED APPLICATIONS

This application is a continuation of U.S. application Ser. No. 15/476,330, filed on Mar. 31, 2017, and issued as U.S. Pat. No. 10,493,130 on Dec. 3, 2019, which is a continuation of U.S. application Ser. No. 13/923,967, filed on Jun. 21, 2013, and issued as U.S. Pat. No. 9,642,892 on May 9, 2017, which is a continuation of U.S. application Ser. No. 13/032,489, filed on Feb. 22, 2011, and issued as U.S. Pat. No. 8,492,335 on Jul. 23, 2013, which claims the benefit of U.S. Provisional Patent Application No. 61/306,938, filed on Feb. 22, 2010, U.S. Provisional Patent Application Ser. No. 61/311,284, filed on Mar. 5, 2010, U.S. Provisional Patent Application Ser. No. 61/428,809, filed on Dec. 30, 2010, and U.S. Provisional Patent Application No. 61/429,428, filed on Jan. 3, 2011, all of which are incorporated by reference herein in their entireties.

TECHNICAL FIELD

This invention relates to compositions and methods for the treatment of tendinopathies, such as tenosynovitis, tendinosis or tendinitis, including Achilles tendinopathy, patellar tendinopathy, lateral epicondylitis or "tennis elbow," medial epicondylitis or "golfer's elbow," plantar fasciitis, and rotator cuff tendinopathy, and in particular to methods for the treatment of tendinopathies by administering compositions comprising platelet-derived growth factor (PDGF).

BACKGROUND OF THE INVENTION

A tendon is a tough band of fibrous connective tissue that usually connects muscle to bone. The elastic properties of tendons modulate forces during locomotion, providing additional stability with no active work. They also store and recover energy at high efficiency. Normal healthy tendons are composed primarily of parallel arrays of type I collagen fibers closely packed together, but also include a small amount of elastin and of proteoglycans. Due to their highly specialized ultrastructure, low level of vascularization and slow collagen turnover, tendons are very slow to heal if injured, and rarely regain their original strength. Partial tears heal by the rapid production of disorganized type-III collagen, which is weaker than normal tendon. Recurrence of injury in the damaged region of tendon is common.

Tendinopathies are chronic disorders or injuries of the tendons, that appear to result from an imbalance between catabolic and anabolic responses that result from gradual wear and tear to the tendon from overuse or aging. The result of this imbalance is tendon degeneration, weakness, tearing, and pain. In contrast, acute tendon injuries such as, for example, tendon rupture or detachment from the bone are quite sudden and usually require surgery to repair the rupture or reattach the tendon to bone. Anyone can develop a tendinopathy, but people who tend to make the same motions over and over again in their jobs, sports, or regular daily activities are more likely to develop them. Tendinopathy usually causes pain, stiffness, and loss of strength in the affected area.

The term tendinopathy refers to two types of tendon injury: tendinosis and tendinitis. The term also encompasses tenosynovitis, a tendinopathy of the outer lining of the tendon which occurs in certain tendons such as flexor tendons and the Achilles tendon.

Tendinosis is a non-inflammatory injury to the tendon characterized by intratendinous degeneration of the tendon usually in the form of microtears in the tissue in and around the tendon caused by overuse, leading to an increase in the number of tendon repair cells around the area of damage. Degeneration of the tendon is caused by damage to or disorganization of the collagen fibers, cells, and vascular components of the tendon, which can reduce the tendon's tensile strength and can lead to tendon rupture if not treated. The changes in collagen organization are characterized by separation/loosening/crimping of fibers, loss of parallel orientation, decrease in fiber diameter and decrease in overall density of collagen. In addition, collagen microtears can also occur that are surrounded by erythrocytes, fibrin, and fibronectin deposits. On the other hand, there is an increase in type III (reparative) collagen. These matrix organization changes can lead to decreased birefringence under polarized light microscopy. In addition to collagen content and organization, tendinosis is also characterized by an increase in mucoid ground substance (proteoglycans) and variation in cellular density in affected areas. Some areas contain abnormally plentiful tenocytes, with rounded nuclei and ultrastructural evidence of increased production of proteoglycan and protein. In contrast, other areas of the affected tendon may contain fewer tenocytes than normal, with small, pyknotic nuclei. Another characteristic feature of tendinosis is proliferation of capillaries and arterioles. Several subcategories of tendon degeneration in tendinosis have been identified by electron microscopy: (1) hypoxic degeneration, (2) hyaline degeneration, (3) mucoid or myxoid degeneration, (4) fibrinoid degeneration, (5) lipoid degeneration, (6) calcification, and (7) fibrocartilaginous and bony metaplasia. These pathologies can coexist with varying prevalence, depending on the anatomical site and the nature of the insult that caused them (eg, hypoxia versus mechanical loading; acute versus chronic injury). For example, mucoid degeneration area is characterized by light microscopy, large mucoid patches and vacuoles between fibers. However, lipoid degeneration is characterized by abnormal intratendinous accumulation of lipid that results in disruption of collagen fiber structure. In some cases, tendinosis is accompanied by focal necrosis or calcification of the tendon. It is a very common reason for chronic pain surrounding a joint. Tendinosis is also characterized by an absence of the initial inflammatory response. Inflammatory cells are thought to be early stage mediators of the repair process, without which tendinosis can become a chronic condition.

Characteristic increases in water content and disorganization of the collagen matrix associated with tendinosis can be diagnosed by ultrasonography or magnetic resonance imaging. Symptoms can vary from simple aching and stiffness in the local area of the tendon to a burning sensation surrounding the entire joint around the injured tendon. For many patients, the pain is frequently worse during and after activity, and the tendon and joint area can become stiffer the following day as swelling impinges on the movement of the tendon.

Tendinitis is an inflammatory injury to the tendon, characterized by degeneration like that observed in tendinosis, but also accompanied by inflammation of the tendon accompanied by vascular disruption and an inflammatory repair response. Tendinitis is often accompanied by fibroblastic and myofibroblastic proliferation, as well as hemorrhage and organizing granulation tissue. Generally tendinitis is referred to by the body part involved, such as Achilles tendinitis (affecting the Achilles tendon), or patellar tendinitis (also known as "jumper's knee," affecting the patellar tendon), though there are certain exceptions, such as lateral epicondylitis (also known as "tennis elbow," affecting the Extensor Carpi Radialis Brevis tendon). Symptoms can vary from aches or pains and local stiffness to a burning sensation surrounding the entire joint around the inflamed tendon. In some cases, tendonitis is characterized by swelling, sometimes accompanied by heat and redness; there may also be visible knots surrounding the joint. For many patients, the pain is usually worse during and after activity, and the tendon and joint area can become stiffer the following day as muscles tighten from the movement of the tendon.

Current treatments are primarily palliative in nature, with treatment traditionally focusing on anti-inflammatory measures, including treatment with nonsteroidal anti-inflammatory drugs (NSAIDs), steroid injections, and physical therapy, despite the fact that tendinosis tends not to be associated with an inflammatory response. More recently, shock wave therapy, low-level laser therapy, sclerotherapy, and other experimental treatments have been tested. For the most part, it appears that some treatments (e.g., NSAIDs and cortisone injections) offer short-term relief, while the longer-term benefit of current treatments remains unclear. Therefore, there is a need for improved methods of treating tendinopathies that offer longer-term benefits compared to existing treatment modalities.

PDGF is stored in the alpha-granules of platelets and is secreted during tissue repair by locally-activated cells, including macrophages, fibroblasts, and endothelial cells. PDGF-BB is one of the major products of the hemorrhage and inflammation of acute tendon injury. Platelet-derived growth factor-BB (PDGF-BB) is a wound healing protein which is known to be chemotactic (cell migration) and mitogenic (cell proliferation) for cells of mesenchymal origin, including bone (osteoblast) and tendon (tenocyte) cells. Additionally, PDGF-BB has been shown to up-regulate vascular endothelial growth factor (VEGF), leading to increased angiogenesis (revascularization), which is essential for successful regenerative processes.

The Achilles tendon is the thickest and strongest tendon in the human body, which allows it to support high loads. The mechanical loading environment in which the Achilles tendon functions makes it prone to rupture. Achilles tendon ruptures can occur as a result of a variety of factors, however rupture is often associated with degenerative changes. (Mafulli N, Wong J, Almekinders L. Types and epidemiology of tendinopathy. Clinics in Sports Medicine. 2003; 22:675-692). Following the repair process, ruptured Achilles tendons demonstrate a reduction in type I collagen and a relative increase in the amount of type III collagen. This change in composition leads to less cross-linking and reduced tensile strength. Even after healing, a ruptured Achilles tendon remains weaker due to hypercellularity, disorganization, and decreased collagen cross-linking (Maffulli N, Moller H D, Evans C H. Tendon Healing: Can it be Optimized? British Journal of Sports Medicine, 2002; 36:315-316). Controversy exists regarding the optimal treatment for Achilles tendon ruptures, with pros and cons to both conservative (non-operative) and surgical therapies. Non-operative treatment results in a higher re-rupture rate and decreased strength but avoids the costs and risks associated with surgery. (Inglis A E, Scott W N, Sculco T P, et al. Ruptures of the tendo achillis: an objective assessment of surgical and nonsurgical treatment. J Bone Joint Surg Am. 1976; 58:990-993; Nistor L. Surgical and Nonsurgical treatment of Achilles tendon rupture: a prospective randomized trial. J Bone Joint Surg Am 1981 63(3):394-9; Chalmers J. Review Article: Treatment of Achilles tendon ruptures. Journal of Orthopaedic Surgery 2008(1):97-99). Surgical repair carries with it the risks of surgery and anesthesia; however it provides increased strength, lower re-rupture rates and a earlier return to athletic activities. (Nistor L. Surgical and Nonsurgical treatment of Achilles tendon rupture: a prospective randomized trial. J Bone Joint Surg Am 1981 63(3):394-9; Rettig A, Liotta F J, Klootwyk T E, Porter D A, Mieling P. Potential Risk of Rerupture in Primary Achilles Tendon Repair in Athletes Younger than 30 years of Age. Am J of Sports Med 2005:33(1):119-123) Regardless of a clinician's preference for treatment of acute Achilles tendon ruptures, surgical repair will continue to have its place in the spectrum of treatment of these injuries in the active patient population. Augmentation of the biological repair process, thereby improving tendon healing, could potentially lead to a faster return to activity and improved clinical outcomes compared to current treatment modalities.

There have been several in vivo and in vitro studies regarding biologic augmentation of tendon healing. See e.g.: Seeherman H J, Archambault J M, Rodeo S A, et al. rhBMP-12 accelerates healing of rotator cuff repairs in a sheep model. J Bone Joint Surg Am. 2008; 90(10):2206-2219; Chan B P, Fu S C, Qin L, et al. Supplementation-time dependence of growth factors in promoting tendon healing. Clin Orthop Relat Res. 2006; 448:240-247; Uggen J C, Dines J, Uggen C W, et al. Tendon gene therapy modulates the local repair environment in the shoulder. J Am Osteopath Assoc. 2005; 105(1):20-21; Gelberman R, Thomopoulos S, Sakiyama-Elbert S, et al. The early effects of sustained platelet-derived growth factor administration on the functional and structural properties of repaired intrasynovial flexor tendons: an in vivo biomechanic study at 3 weeks in canines. J Hand Surg Am. 2007; 32(3):373-379; Thomopoulos S, Das R, Silva M J, et al. Enhanced flexor tendon healing through controlled delivery of PDGF-BB. J Orthop Res. 2009; 27(9):1209-1215; Thomopoulos S, Zaegel M, Das R, et al. PDGF-BB released in tendon repair using a novel delivery system promotes cell proliferation and collagen remodeling. *J Orthop Res.* 2007; 25(10):1358-1368; Dines J, Grande D, Dines D. Tissue Engineering and Rotator Cuff Tendon Healing. J Shoulder Elbow Surg, September/October 2007: 204S-206S.

Delivering rhPDGF-BB to the site of repair in sufficient doses and over the proper time-course is important in achieving the desired clinical effect. Several studies describe sutures coated with biologics. See e.g. Rickert M, Jung M, Adiyaman M, Richter W, Wimank H G. Growth and differentiation factor 5 coated suture stimulates tendon healing in an Achilles tendon model in rats. Growth Factors 2001; 19:115-126; Weiler A, Forster C, Hunt P, Falk R, Jung T, Unterhauser F N, Bergmann V, Schmidmaier G, Haas N P. The Influence of Locally Applied Platelet-Derived Growth Factor-BB on Free Tendon Graft Remodeling After Anterior Cruciate Ligament Reconstruction. American Journal of Sports Medicine 2004; 32(4):881-891; Dines J, Weber L, Razzano P, et al. The Effect of Growth Differentiation Factor-5-Coated Sutures on Tendon Repair in a Rat Model. J Shoulder Elbow Surg 2007; 16:215S-221S; Uggen C, Dines J, McGarry M, et al. The effect of Recombinant Human Platelet Derived growth Factor BB coated sutures on Rotator cuff Healing in a Sheep Model. Arthroscopy: 2010: 26(11): 1456-1462.

What is needed are improved sutures for delivery of PDGF to a tendon, for example, for repair of ruptured tendon such as ruptured Achilles tendons.

SUMMARY

In one aspect, provided herein is a method of treating a tendinopathy comprising administering to an affected site an effective amount of a composition comprising a PDGF and a buffer. In some embodiments, the tendinopathy is a tendinosis. In some embodiments, the tendinopathy is a tendinitis. In some embodiments, the tendinopathy is a tenosynovitis. In some embodiments, the PDGF is selected from the group consisting of PDGF-AA, PDGF-BB, PDGF-AB, PDGF-CC, and PDGF-DD. In some embodiments, the PDGF is PDGF-BB. In some embodiments, the PDGF is recombinant human (rh) PDGF-BB. In some embodiments, the effective amount of the composition comprises between about 75 μg and about 7,500 μg of PDGF-BB per dose. In some embodiments, the effective amount of the composition comprises between about 500 μg to about 1,000 μg of PDGF-BB per dose. In some embodiments, the effective amount of the composition comprises between about 5,000 μg to about 7,500 μg of PDGF-BB per dose. In some embodiments, the effective amount of the composition comprises between about 450 μg to about 3000 μg of PDGF-BB per dose. In some embodiments, the effective amount of the composition comprises between about 400 μg to about 1000 μg of PDGF-BB per dose. In some embodiments, the effective amount of the composition comprises between about 500 μg to about 900 μg of PDGF-BB per dose. In some embodiments, the effective amount of the composition comprises between about 600 μg to about 800 μg of PDGF-BB per dose. In some embodiments, the effective amount of the composition comprises between about 650 μg to about 750 μg of PDGF-BB per dose. In some embodiments, the effective amount of the composition comprises about 700 μg of PDGF-BB per dose. In some embodiments, the composition has a volume of about 1.0 to about 2.0 ml per dose. In some embodiments, the composition has a volume of about 1.5 ml per dose. In some embodiments, the buffer is selected from the group consisting of phosphate-buffered saline ("PBS"), sodium acetate, ammonium acetate, acetic acid, citric acid, sodium citrate, tris(hydroxymethyl)aminoethane ("tris"), N-2-hydroxyethylpiperazine-N'-2-ethanesulfonic acid ("HEPES"), 3-(N-morpholino) propanesulfonic acid ("MOPS"), 2-(N-morpholino)ethanesulfonic acid ("MES"), N-(2-acetamido)iminodiacetic acid ("ADA"), piperazine-N, N'-bis(2-ethanesulfonic acid) ("PIPES"), and N-(2-acetamido)-2-aminoethanesulfonic acid ("ACES"). In some embodiments, the buffer is sodium acetate. In some embodiments, the sodium acetate is at a concentration between about 10 mM and about 100 mM. In some embodiments, the sodium acetate is at a concentration of about 20 mM. In some embodiments, the composition has a pH between about 4.0 and about 7.0. In some embodiments, the composition has pH of about 6. In some embodiments, the administering is by direct injection to the affected site. In some embodiments, the affected site is an osseous-tendon junction. In some embodiments, the affected site is a tendon. In some embodiments, the tendinopathy is selected from the group consisting of Achilles tendinopathy, patellar tendinopathy, lateral epicondylitis, medial epicondylitis, plantar fasciitis, and rotator cuff tendinopathy. In some embodiments, the tendinopathy is lateral epicondylitis. In some embodiments, the composition is administered as a single dose. In some embodiments, the composition is administered by a single injection. In some embodiments, the composition is administered in more than one dose. In some embodiments, the composition is administered by a single injection once a week for four weeks. In some embodiments, the method results in an increase in tendon strength of at least about 60% within about 7 days of administration, as compared to baseline. In some embodiments, the method results in an increase in tendon strength of at least about 65% within about 7 days of administration, as compared to baseline. In some embodiments, the method results in an increase in tendon strength of at least about 70% within about 7 days of administration, as compared to baseline. In some embodiments, the method results in the tendon achieving at least about 80% of its final strength within about 7 days of administration, wherein final strength is measured at about 21 days after administration. In some embodiments, the method results in the tendon achieving at least about 85% of its final strength within about 7 days of administration, wherein final strength is measured at about 21 days after administration. In some embodiments, the method results in the tendon achieving at least about 90% of its final strength within about 7 days of administration, wherein final strength is measured at about 21 days after administration.

In another aspect, provided herein is a method of treating a tendinopathy comprising administering to an affected site an effective amount of a composition consisting of a PDGF and a buffer. In some embodiments, the tendinopathy is a tendinosis. In some embodiments, the tendinopathy is a tendinitis. In some embodiments, the tendinopathy is a tenosynovitis. In some embodiments, the PDGF is selected from the group consisting of PDGF-AA, PDGF-BB, PDGF-AB, PDGF-CC, and PDGF-DD. In some embodiments, the PDGF is PDGF-BB. In some embodiments, the PDGF is recombinant human (rh) PDGF-BB. In some embodiments, the effective amount of the composition comprises between about 75 μg and about 7,500 μg of PDGF-BB per dose. In some embodiments, the effective amount of the composition comprises between about 500 μg to about 1,000 μg of PDGF-BB per dose. In some embodiments, the effective amount of the composition comprises between about 5,000 μg to about 7,500 μg of PDGF-BB per dose. In some embodiments, the effective amount of the composition comprises between about 450 μg to about 3000 μg of PDGF-BB per dose. In some embodiments, the effective amount of the composition comprises between about 400 μg to about 1000 μg of PDGF-BB per dose. In some embodiments, the effective amount of the composition comprises between about 500 μg to about 900 μg of PDGF-BB per dose. In some embodiments, the effective amount of the composition comprises between about 600 μg to about 800 μg of PDGF-BB per dose. In some embodiments, the effective amount of the composition comprises between about 650 μg to about 750 μg of PDGF-BB per dose. In some embodiments, the effective amount of the composition comprises about 700 μg of PDGF-BB per dose. In some embodiments, the composition has a volume of about 1.0 to about 2.0 ml per dose. In some embodiments, the composition has a volume of about 1.5 ml per dose. In some embodiments, the buffer is selected from the group consisting of phosphate-buffered saline ("PBS"), sodium acetate, ammonium acetate, acetic acid, citric acid, sodium citrate, tris(hydroxymethyl)aminoethane ("tris"), N-2-hydroxyethylpiperazine-N'-2-ethanesulfonic acid ("HEPES"), 3-(N-morpholino) propanesulfonic acid ("MOPS"), 2-(N-morpholino)ethanesulfonic acid ("MES"), N-(2-acetamido)iminodiacetic acid ("ADA"), piperazine-N, N'-bis(2-ethanesulfonic acid) ("PIPES"), and N-(2-acetamido)-2-aminoethanesulfonic acid ("ACES"). In some embodiments, the buffer is sodium acetate. In some embodiments, the sodium acetate is at a concentration between about 10 mM and about 100 mM. In some embodiments, the sodium acetate is at a concentration of about 20 mM. In some embodiments, the composition has a pH between about 4.0 and about 7.0. In some embodiments, the composition has pH of about 6. In some embodiments, the administering is by direct injection to the affected site. In some embodiments, the affected site is an osseous-tendon junction. In some embodiments, the affected site is a tendon. In some embodiments, the tendinopathy is selected from the group consisting of Achilles tendinopathy, patellar tendinopathy, lateral epicondylitis, medial epicondylitis, plantar fasciitis, and rotator cuff tendinopathy. In some embodiments, the tendinopathy is lateral epicondylitis. In some embodiments, the composition is administered as a single dose. In some embodiments, the composition is administered by a single injection. In some embodiments, the composition is administered in more than one dose. In some embodiments, the composition is administered by a single injection once a week for four weeks. In some embodiments, the method results in an increase in tendon strength of at least about 60% within about 7 days of administration, as compared to baseline. In some embodiments, the method results in an increase in tendon strength of at least about 65% within about 7 days of administration, as compared to baseline. In some embodiments, the method results in an increase in tendon strength of at least about 70% within about 7 days of administration, as compared to baseline. In some embodiments, the method results in the tendon achieving at least about 80% of its final strength within about 7 days of administration, wherein final strength is measured at about 21 days after administration. In some embodiments, the method results in the tendon achieving at least about 85% of its final strength within about 7 days of administration, wherein final strength is measured at about 21 days after administration. In some embodiments, the method results in the tendon achieving at least about 90% of its final strength within about 7 days of administration, wherein final strength is measured at about 21 days after administration. In some embodiments, the method consists of administering to an affected site an effective amount of a composition consisting of a PDGF and a buffer.

In another aspect, provided herein is a composition for use in treating a tendinopathy, comprising an effective amount of a PDGF and a buffer. In some embodiments, the tendinopathy is a tendinosis. In some embodiments, the tendinopathy is a tendinitis. In some embodiments, the tendinopathy is a tenosynovitis. In some embodiments, the PDGF is selected from the group consisting of PDGF-AA, PDGF-BB, PDGF-AB, PDGF-CC, and PDGF-DD. In some embodiments, the PDGF is PDGF-BB. In some embodiments, the PDGF is recombinant human (rh) PDGF-BB. In some embodiments, the effective amount comprises between about 75 µg and about 7,500 µg of PDGF-BB per dose. In some embodiments, the effective amount comprises between about 500 µg to about 1,000 µg of PDGF-BB per dose. In some embodiments, the effective amount comprises between about 5,000 µg to about 7,500 µg of PDGF-BB per dose. In some embodiments, the effective amount comprises between about 450 µg to about 3000 µg of PDGF-BB per dose. In some embodiments, the effective amount comprises between about 400 µg to about 1000 µg of PDGF-BB per dose. In some embodiments, the effective amount comprises between about 500 µg to about 900 µg of PDGF-BB per dose. In some embodiments, the effective amount comprises between about 600 µg to about 800 µg of PDGF-BB per dose. In some embodiments, the effective amount comprises between about 650 µg to about 750 µg of PDGF-BB per dose. In some embodiments, the effective amount comprises about 700 µg of PDGF-BB per dose. In some embodiments, the composition has a volume of about 1.0 to about 2.0 ml per dose. In some embodiments, the composition has a volume of about 1.5 ml per dose. In some embodiments, the buffer is selected from the group consisting of phosphate-buffered saline ("PBS"), sodium acetate, ammonium acetate, acetic acid, citric acid, sodium citrate, tris(hydroxymethyl)aminoethane ("tris"), N-2-hydroxyethylpiperazine-N'-2-ethanesulfonic acid ("HEPES"), 3-(N-morpholino) propanesulfonic acid ("MOPS"), 2-(N-morpholino)ethanesulfonic acid ("MES"), N-(2-acetamido)iminodiacetic acid ("ADA"), piperazine-N, N'-bis(2-ethanesulfonic acid) ("PIPES"), and N-(2-acetamido)-2-aminoethanesulfonic acid ("ACES"). In some embodiments, the buffer is sodium acetate. In some embodiments, the sodium acetate is at a concentration between about 10 mM and about 100 mM. In some embodiments, the sodium acetate is at a concentration of about 20 mM. In some embodiments, the composition has a pH between about 4.0 and about 7.0. In some embodiments, the composition has pH of about 6. In some embodiments, the treating comprises administering the composition by direct injection to the affected site. In some embodiments, the affected site is an osseous-tendon junction. In some embodiments, the affected site is a tendon. In some embodiments, the tendinopathy is selected from the group consisting of Achilles tendinopathy, patellar tendinopathy, lateral epicondylitis, medial epicondylitis, plantar fasciitis, and rotator cuff tendinopathy. In some embodiments, the tendinopathy is lateral epicondylitis. In some embodiments, the composition is administered as a single dose. In some embodiments, the composition is administered by a single injection. In some embodiments, the composition is administered in more than one dose. In some embodiments, the composition is administered by a single injection once a week for four weeks. In some embodiments, the treating results in an increase in tendon strength of at least about 60% within about 7 days of administration, as compared to baseline. In some embodiments, the treating results in an increase in tendon strength of at least about 65% within about 7 days of administration, as compared to baseline. In some embodiments, the treating results in an increase in tendon strength of at least about 70% within about 7 days of administration, as compared to baseline. In some embodiments, the treating results in the tendon achieving at least about 80% of its final strength within about 7 days of administration, wherein final strength is measured at about 21 days after administration. In some embodiments, the treating results in the tendon achieving at least about 85% of its final strength within about 7 days of administration, wherein final strength is measured at about 21 days after administration. In some embodiments, the treating results in the tendon achieving at least about 90% of its final strength within about 7 days of administration, wherein final strength is measured at about 21 days after administration. In some embodiments, the composition consists of an effective amount of a PDGF and a buffer.

In another aspect, provided herein is the use of the PDGF compositions described herein in connection with the methods described herein, unless otherwise noted or as is clear from the specific context. The PDGF compositions described herein may also be used in the preparation of a medicament for use in the methods described herein.

DETAILED DESCRIPTION

Figure 1:
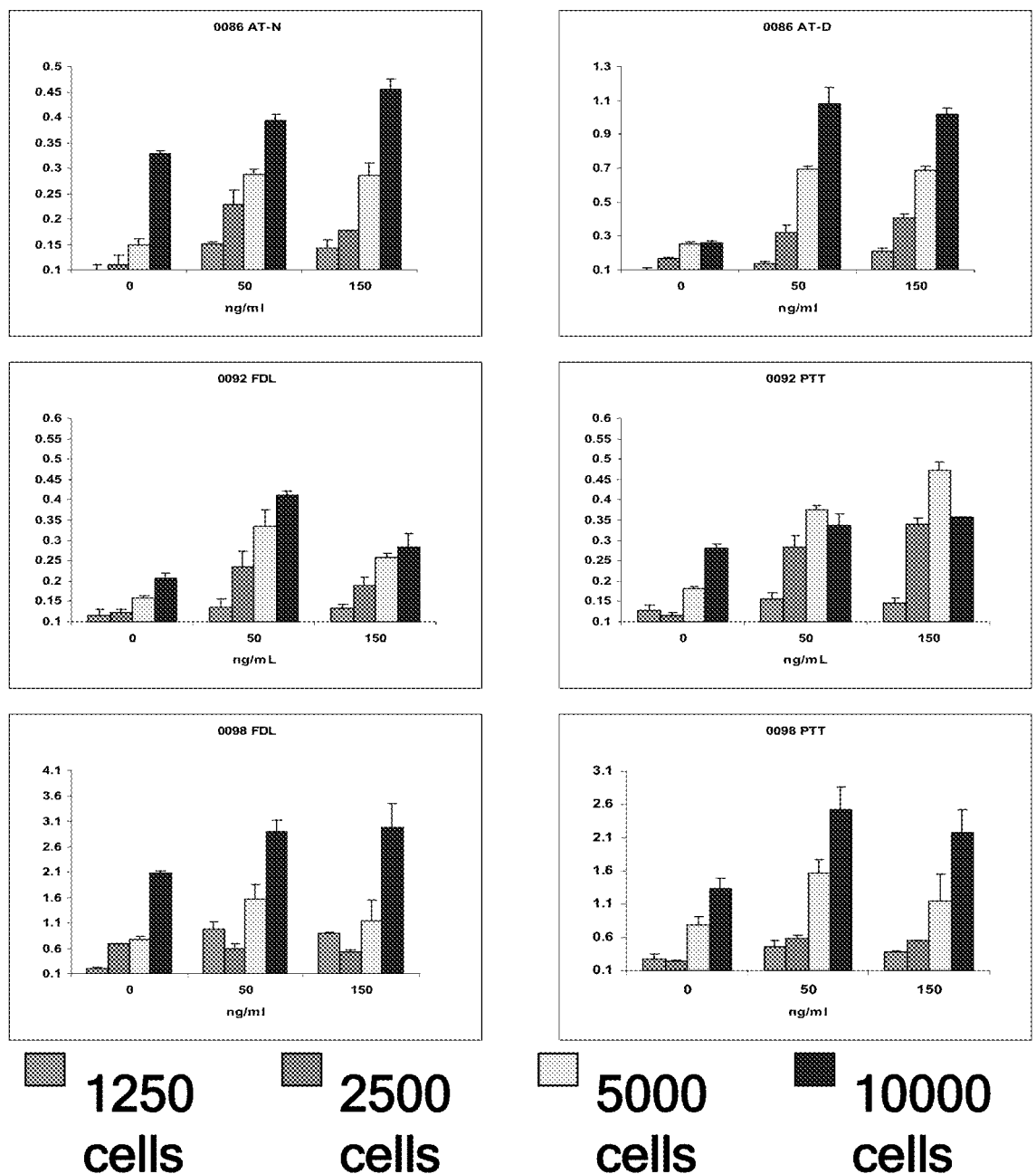
FIG. 1 shows the effect of rhPDGF-BB treatment on tenocyte cell migration.

All references cited herein, including without limitation, patents, patent applications and scientific references, are hereby incorporated herein by reference in their entirety.

The compositions and methods of the invention surprisingly result in improved treatment of tendinopathies. In some embodiments, the compositions and methods of the invention result in increased strength of the tendon and an increased rate of tendon strength recovery. In some embodiments, the compositions and methods of the invention result in increased strength of the tendon. In some embodiments, the compositions and methods of the invention result in an increased rate of tendon strength recovery. For example, as a tendon heals after an injury, the biomechanical strength of the tendon increases as a process of tendon healing. Administration of a composition of the invention may result in a more rapid increase in tendon strength. Without wishing to be bound by theory, this more rapid increase in strength may be helpful in promoting healing of the tendon; provided the load bearing does not further increase the tendon injury, load bearing on a tendon generally improves the healing response of the tendon, as it generally results in improved tissue remodeling and reorganization. A faster initial increase in tendon strength (e.g. resulting from administration of a composition of the invention) may result in an ability to begin load bearing on the tendon more rapidly, thus further improving the tendon healing response. Without wishing to be bound by theory, the improvement in strength of the tendon may be caused by an increase in cellular proliferation and/or extracellular matrix production, and/or by an improvement in organization of the tissue (for example, an improvement in organization of the extracellular matrix).

Additionally, without wishing to be bound by theory, the inventors surprisingly discovered that when the compositions of the invention are administered directly into the tendon (e.g. by injection), the PDGF remains localized at the site of administration (e.g. at the site of injection). For example, as further detailed in Example 5 below, it was unexpected that administration of a composition consisting of PDGF in a buffer would result in PDGF remaining localized at the site of injection.

Definitions

As used herein, the term "treatment" refers to clinical intervention designed to alter the natural course of clinical pathology of the disorder being treated (e.g., a tendinopathy, such as tendinosis, tendinitis, or tenosynovitis). Desirable effects of treatment include, for example, one or more of decreasing pain or stiffness of the affected joint or limb, increasing mobility and strength of the affected joint or limb, decreasing the rate of tendinopathy progression, decreasing inflammation, increasing the strength of the tendon, improving the rate of tendon strength recovery, ameliorating or palliating the disease state, and remission or improved prognosis. An individual is successfully "treated," for example, if one or more symptoms associated with a tendinopathy are mitigated or eliminated.

As used herein, the term "effective amount" refers to at least an amount effective, at dosages and for periods of time necessary, to achieve the desired therapeutic or prophylactic result. An effective amount can be provided in one or more administrations.

Reference to "about" a value or parameter herein also includes (and describes) embodiments that are directed to that value or parameter per se.

As used herein and in the appended claims, the singular forms "a," "an," and "the" include plural reference unless the context clearly indicates otherwise. For example, reference to a "PDGF homodimer" is a reference to one or multiple PDGF homodimers, and includes equivalents thereof known to those skilled in the art, and so forth.

It is understood that all aspects and embodiments of the invention described herein include "comprising," "consisting," and "consisting essentially of" aspects and embodiments. It is to be understood that methods or compositions "consisting essentially of" the recited elements include only the specified steps or materials and those that do not materially affect the basic and novel characteristics of those methods and compositions (e.g., administering to an affected site an effective amount of a composition consisting essentially of a PDGF and a buffer, or a composition consisting essentially of an effective amount of a PDGF in a buffered solution).

Platelet-Derived Growth Factor and Compositions Thereof

As used herein, the term "platelet-derived growth factor" or "PDGF" refers to any of four different isoforms of PDGF that activate cellular responses through two different receptors. Those isoforms include A (observed as a homodimer designated PDGF-AA and as part of a heterodimer with the B isoform designated PDGF-AB), B (observed as a homodomer designated PDGF-BB and as part of a heterodimer with the A isoform designated PDGF-AB), C (observed as a homodimer designated PDGF-CC) and D (observed as a homodimer designated PDGF-DD). Generally herein, the term "PDGF" refers generally to the known PDGF homo- and heterodimers (e.g., PDGF-AA, PDGF-BB, PDGF-AB, PDGF-CC, and PDGF-DD).

Provided herein are methods of treating tendinopathies in an individual and compositions for use in those methods. In general, the methods of treatment comprise administering a composition comprising PDGF to an affected site in an individual who has a tendinopathy. Specifically, the methods of treatment comprise administering a composition comprising PDGF and a buffer to the site of the tendinopathy. In some embodiments, the composition comprises a PDGF and a buffer (e.g., a buffered solution of PDGF).

In some embodiments, the compositions comprise a PDGF and a buffer. In some embodiments, the PDGF comprises a PDGF dimer selected from the group consisting of PDGF-AA, PDGF-BB, PDGF-AB, PDGF-CC, PDGF-DD, and mixtures and derivatives thereof. In some embodiments, the PDGF dimer is a homodimer. In some embodiments, the PDGF homodimer is selected from the group consisting of PDGF-AA, PDGF-BB, PDGF-CC, and PDGF-DD. In some embodiments, the PDGF homodimer is PDGF-BB. In some embodiments, the PDGF dimer is a heterodimer. In some embodiments, the PDGF heterodimer is PDGF-AB.

In some embodiments, PDGF can be obtained from natural sources. In some embodiments, PDGF can be produced by recombinant DNA techniques. In some embodiments, PDGF or fragments thereof may be produced using peptide synthesis techniques known to one of skill in the art, such as solid phase peptide synthesis.

When obtained from natural sources, PDGF can be derived from biological fluids. In some embodiments, the biological fluids can comprise any treated or untreated fluid associated with living organisms including blood. Biological fluids can also comprise blood components including platelet concentrate, apheresed platelets, platelet-rich plasma, plasma, serum, and fresh frozen plasma. Biological fluids can comprise platelets separated from plasma and resuspended in a physiological fluid or buffer.

When produced by recombinant DNA techniques, a DNA sequence encoding a single monomer (e.g., a PDGF B-chain or A-chain) can be inserted into cultured prokaryotic or eukaryotic cells for expression to subsequently produce the homodimer (e.g., PDGF-BB or PDGF-AA). In some embodiments, the PDGF comprises a PDGF homodimer (e.g., PDGF-AA, PDGF-BB, PDGF-CC, or PDGF-DD). In some embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g., PDGF-AB). In some embodiments, the PDGF comprises a PDGF heterodimer (e.g., PDGF-AB). Commercially available recombinant human PDGF-BB may be obtained commercially from a variety of sources, including, but not limited to Leinco Technologies, Inc. (St. Louis, Mo.) and R&D Systems, Inc. (Minneapolis, Minn.).

In some embodiments described herein, the PDGF comprises a recombinant human PDGF ("rhPDGF"). In some embodiments, the recombinant human PDGF ("rhPDGF") is a PDGF dimer selected from the group consisting of rhPDGF-AA, rhPDGF-BB, rhPDGF-AB, rhPDGF-CC, rhPDGF-DD, and mixtures and derivatives thereof. In some embodiments, the recombinant human PDGF is an rhPDGF homodimer. In some embodiments, the recombinant human PDGF homodimer is selected from the group consisting of rhPDGF-AA, rhPDGF-BB, rhPDGF-CC, and rhPDGF-DD. In some embodiments, the recombinant human PDGF homodimer is rhPDGF-BB. In some embodiments, the recombinant human PDGF is an rhPDGF heterodimer. In some embodiments, the recombinant human PDGF heterodimer is rhPDGF-AB.

In some embodiments, PDGF-B comprises one or more of the following fragments: amino acids 1-31, 1-32, 33-108, 33-109, and/or 1-108 of the entire human B-chain. The complete amino acid sequence (amino acids 1-109) of the B-chain of human PDGF is provided in FIG. 15 of U.S. Pat. No. 5,516,896. It is to be understood that the PDGF-BB compositions of the present invention may comprise a combination of intact human PDGF-B (amino acids 1-109) and fragments thereof. Other fragments of PDGF may be employed such as those disclosed in U.S. Pat. No. 5,516,896. In some embodiments, the PDGF-BB comprises at least 65% of full-length human PDGF-B (amino acids 1-109). In some embodiments, the PDGF-BB comprises at least 75%, 80%, 85%, 90%, 95%, or 99% of full-length human PDGF-B (amino acid 1-109).

In some embodiments, the composition comprises a PDGF dimer (e.g., an rhPDGF dimer) selected from the group consisting of PDGF-AA, PDGF-BB, PDGF-AB, PDGF-CC, and PDGF-DD, and the composition comprises a PDGF dimer at a concentration ranging from about 0.01 mg/ml to about 10.0 mg/ml, from about 0.05 mg/ml to about 5.0 mg/ml, from about 0.1 mg/ml to about 1.0 mg/ml, or from about 0.1 mg/ml to about 2.0 mg/ml, from about 0.1 mg/ml to about 3.0 mg/ml, from about 0.1 mg/ml to about 4.0 mg/ml, about 0.1 mg/ml to about 0.4 mg/ml, from about 0.1 mg/ml to about 5.0 mg/ml, about 0.9 mg/ml to about 1.5 mg/ml. In some embodiments, the composition comprises a PDGF dimer at a concentration of about 3.4 mg/ml. In some embodiments, the composition comprises a PDGF dimer at a concentration of about 1.0 mg/ml. In some embodiments, the composition comprises a PDGF dimer at a concentration of about 0.34 mg/ml. In some embodiments, the composition comprises a PDGF dimer at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; about 1.0 mg/ml; about 1.5 mg/ml; about 2.0 mg/ml; about 2.5 mg/ml; about 3.0 mg/ml; about 3.5 mg/ml; about 4.0 mg/ml; about 4.5 mg/ml; or about 5.0 mg/ml. It is to be understood that these concentrations are simply examples of particular embodiments, and that the concentration of PDGF dimer may be within any of the concentration ranges stated above.

In some embodiments, the PDGF dimer (e.g., an rhPDGF dimer) is PDGF-BB. In some embodiments, the composition comprises PDGF-BB at a concentration ranging from about 0.01 mg/ml to about 10.0 mg/ml, from about 0.05 mg/ml to about 5.0 mg/ml, from about 0.1 mg/ml to about 1.0 mg/ml, or from about 0.1 mg/ml to about 2.0 mg/ml, from about 0.1 mg/ml to about 3.0 mg/ml, from about 0.1 mg/ml to about 4.0 mg/ml, from about 0.1 mg/ml to about 5.0 mg/ml, about 0.1 mg/ml to about 0.4 mg/ml, about 0.9 mg/ml to about 1.5 mg/ml. In some embodiments, the composition comprises PDGF-BB at a concentration of about 3.4 mg/ml. In some embodiments, the composition comprises PDGF-BB at a concentration of about 1.0 mg/ml. In some embodiments, the composition comprises PDGF-BB at a concentration of about 0.34 mg/ml. In some embodiments, the composition comprises PDGF-BB at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; about 1.0 mg/ml; about 1.5 mg/ml; about 2.0 mg/ml; about 2.5 mg/ml; about 3.0 mg/ml; about 3.5 mg/ml; about 4.0 mg/ml; about 4.5 mg/ml; or about 5.0 mg/ml. It is to be understood that these concentrations are simply examples of particular embodiments, and that the concentration of rhPDGF-BB may be within any of the concentration ranges stated above.

In some embodiments, the PDGF is selected from the group consisting of PDGF-AA, PDGF-BB, PDGF-AB, PDGF-CC, and PDGF-DD. Various amounts of PDGF may be used in the compositions of the present invention. Amounts of PDGF that can be used include, but are not limited to, amounts in the following ranges: about 1 µg to about 50 mg, about 10 µg to about 25 mg, about 100 µg to about 10 mg, about 250 µg to about 5 mg, and about 450 µg to about 3 mg. In some embodiments, the PDGF is PDGF-BB. Various amounts of PDGF-BB may be used in the compositions of the present invention. Amounts of PDGF-BB that can be used include, but are not limited to, amounts in the following ranges: about 1 µg to about 50 mg, about 10 µg to about 25 mg, about 100 µg to about 10 mg, about 250 µg to about 5 mg and about 450 µg to about 3 mg.

The concentration of PDGF (e.g., rhPDGF), including PDGF-AA, PDGF-BB, PDGF-AB, PDGF-CC, and PDGF-DD, in some embodiments of the present invention can be determined, for example, by using an enzyme-linked immunoassay as described in U.S. Pat. Nos. 6,221,625; 5,747,273; and 5,290,708, or any other assay known in the art for determining PDGF concentration. When provided herein, the molar concentration of rhPDGF is determined based on the molecular weight of a PDGF homodimer (e.g., PDGF-BB, MW~25 kDa).

In some embodiments of the present invention, the PDGF (e.g., rhPDGF) can be in a highly purified form. Purified PDGF, as used herein, comprises compositions having greater than about 95% by weight PDGF prior to incorporation in solutions of the present invention. The solution may be prepared using any pharmaceutically acceptable buffer or diluent. In some embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In some embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into the compositions.

In a further embodiment, the PDGF can be partially purified. Partially purified PDGF, as used herein, comprises compositions having PDGF in the context of platelet-rich plasma, fresh frozen plasma, or any other blood product that requires collection and separation to produce PDGF. Embodiments of the present invention contemplate that any of the PDGF isoforms provided herein, including homodimers and heterodimers, can be purified or partially purified. Compositions of the present invention comprising PDGF mixtures may comprise PDGF isoforms or PDGF fragments in partially purified proportions. Partially purified and purified PDGF, In some embodiments, can be prepared as described in U.S. application Ser. No. 11/159,533 (U.S. Patent Publication No. 2006/0084602 A1).

In any of the embodiments described herein, the highly purified or partially purified PDGF is selected from the group consisting of PDGF-AA, PDGF-BB, PDGF-AB, PDGF-CC, and PDGF-DD. In any of the embodiments described herein, the highly purified or partially purified PDGF is PDGF-BB.

Buffers

In some embodiments, the compositions comprise a PDGF and a buffer, preferably a pharmaceutically acceptable buffer. Buffers suitable for use in PDGF solutions of the present invention can comprise, but are not limited to, carbonates, phosphates (e.g., phosphate-buffered saline), saline, histidine, acetates (e.g., sodium acetate or ammonium acetate), acidic buffers such as acetic acid, citric acid, sodium citrate and HCl, and organic buffers such as lysine, Tris buffers (e.g., tris(hydroxymethyl)aminoethane), N-2-hydroxyethylpiperazine-N'-2-ethanesulfonic acid (HEPES), 3-(N-morpholino) propanesulfonic acid (MOPS), 2-(N-morpholino)ethanesulfonic acid (MES), N-(2-acetamido)iminodiacetic acid ("ADA"), piperazine-N,N'-bis(2-ethanesulfonic acid) (PIPES), and N-(2-acetamido)-2-aminoethanesulfonic acid (ACES).

Buffers can be selected based on biocompatibility with PDGF and the buffer's ability to impede undesirable protein modification. Buffers can additionally be selected based on compatibility with host tissues and pharmaceutical acceptability. In some embodiments, the PDGF compositions comprise PDGF in sodium acetate buffer. In some embodiments, the PDGF in sodium acetate buffer is selected from the group consisting of PDGF-AA, PDGF-BB, PDGF-AB, PDGF-CC, and PDGF-DD. In some embodiments, the PDGF in sodium acetate buffer is rhPDGF-BB.

The buffers may be employed at different molarities, for example between about 0.1 mM to about 100 mM, about 1 mM to about 100 mM, about 10 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM. The buffers may be employed at different concentrations, for example, between about 0.01 mg/ml to about 10 mg/ml, 0.05 mg/ml to about 5 mg/ml, about 0.5 mg/ml to about 5 mg/ml, 0.1 mg/ml to about 1 mg/ml, and about 0.5 mg/ml to about 1 mg/ml, or any concentration within these ranges.

In another embodiment, solutions comprising PDGF may be formed by solubilizing lyophilized PDGF in water, wherein prior to solubilization the PDGF is lyophilized from an appropriate buffer.

Compositions comprising PDGF and a buffer according to some embodiments of the present invention can have a pH ranging from about 3.0 to about 8.0 or from about 4.0 to about 7.0. In some embodiments, the composition comprising PDGF and a buffer has a pH ranging from about 5.0 to about 8.0, more preferably about 5.5 to about 7.0, most preferably about 5.5 to about 6.5, or any value within these ranges. In some embodiments described herein, the PDGF composition is at a pH between about 4.0 and about 7.0. In some embodiments described herein, the PDGF composition is at a pH between about 5.0 and about 7.0. In some embodiments described herein, the PDGF composition is at a pH of about 4.0, about 5.0, about 6.0, or about 7.0. The pH of compositions comprising PDGF and a buffer, in some embodiments, can be compatible with the prolonged stability and efficacy of PDGF or any other desired biologically active agent. PDGF is generally more stable in an acidic environment. Therefore, in accord with some embodiments, provided herein is an acidic storage formulation of a PDGF composition. In accord with some embodiments, the composition comprising PDGF and a buffer preferably has a pH from about 3.0 to about 7.0, and more preferably from about 4.0 to about 6.5. The biological activity of PDGF, however, can be optimized in a solution having a neutral pH range. Therefore, in some embodiments, provided herein is a neutral pH formulation of a composition comprising PDGF and a buffer. In accord with this embodiment, the composition preferably has a pH from about 5.0 to about 8.0, more preferably about 5.5 to about 7.0, most preferably about 5.5 to about 6.5.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, the PDGF compositions provided herein comprise a PDGF selected from the group consisting of PDGF-AA, PDGF-BB, PDGF-CC, PDGF-DD, and PDGF-AB and a buffer selected from the group consisting of PBS, sodium acetate, ammonium acetate, acetic acid, citric acid, sodium citrate, tris(hydroxymethyl)aminoethane, HEPES, MOPS, MES, ADA, PIPES, and ACES. In some embodiments, the PDGF compositions provided herein comprise rhPDGF-BB and a buffer selected from the group consisting of PBS, sodium acetate, ammonium acetate, acetic acid, citric acid, sodium citrate, tris(hydroxymethyl) aminoethane, HEPES, MOPS, MES, ADA, PIPES, and ACES. In some embodiments, the PDGF composition comprises rhPDGF-BB and PBS. In some embodiments, the PDGF composition comprises rhPDGF-BB and sodium acetate. In some embodiments, the PDGF composition comprises rhPDGF-BB and ammonium acetate. In some embodiments, the PDGF composition comprises rhPDGF-BB and acetic acid. In some embodiments, the PDGF composition comprises rhPDGF-BB and citric acid. In some embodiments, the PDGF composition comprises rhPDGF-BB and sodium citrate. In some embodiments, the PDGF composition comprises rhPDGF-BB and tris(hydroxymethyl)aminoethane. In some embodiments, the rhPDGF composition comprises PDGF-BB and HEPES. In some embodiments, the PDGF composition comprises rhPDGF-BB and MOPS. In some embodiments, the PDGF composition comprises rhPDGF-BB and MES. In some embodiments, the PDGF composition comprises rhPDGF-BB and ADA. In some embodiments, the PDGF composition comprises rhPDGF-BB and PIPES. In some embodiments, the PDGF composition comprises rhPDGF-BB and ACES.

In some embodiments described herein, the buffer is at a concentration between 1 mM and 1000 mM. In some embodiments described herein, the buffer is at a concentration between 10 mM and 1000 mM. In some embodiments described herein, the buffer is at a concentration between 100 mM and 1000 mM. In some embodiments described herein, the buffer is at a concentration between 5 mM and 500 mM. In some embodiments described herein, the buffer is at a concentration between 50 mM and 500 mM. In some embodiments described herein, the buffer is at a concentration between 10 mM and 100 mM. In some embodiments described herein, the buffer is at a concentration between 20 mM and 200 mM. In some embodiments described herein, the buffer is at a concentration of 10 mM, 20 mM, 30 mM, 40 mM, 50 mM, 60 mM, 70 mM, 80 mM, 90 mM or 100 mM.

In some embodiments, the PDGF composition comprises rhPDGF-AA and 20 mM sodium acetate at about pH=6.0. In some embodiments, the PDGF composition comprises rhPDGF-AB and 20 mM sodium acetate at about pH=6.0. In some embodiments, the PDGF composition comprises rhPDGF-BB and 20 mM sodium acetate at about pH=6.0. In some embodiments, the PDGF composition comprises rhPDGF-CC and 20 mM sodium acetate at about pH=6.0. In some embodiments, the PDGF composition comprises rhPDGF-DD and 20 mM sodium acetate at about pH=6.0.

Doses and Dosing Regimens

Effective doses of PDGF identified in a rat tendon model may be extrapolated to effective amounts for other individuals, such as humans, based on the relative size of treatment area of the tendon. For example, the treatment area of a human Achilles tendon is approximately 69 times larger than the treatment area of a rat Achilles tendon, so an effective amount or dose of a PDGF for a human patient may be approximately 69 times the effective amount or dose of a PDGF determined in the rat tendon model.

Exemplary effective amounts or doses delivered by administration of the PDGF compositions provided herein include, but are not limited to, about 450 μg to about 3,000 μg per dose, about 1 μg to about 10,000 μg per dose, including for example any of about 1 μg to about 7,500 μg per dose, about 1 μg to about 5,000 μg per dose, about 1 μg to about 2,500 μg per dose, about 1 μg to about 1,000 μg per dose, about 1 μg to about 500 μg per dose, about 1 μg to about 250 μg per dose, about 1 μg to about 100 μg per dose, about 10 μg to about 10,000 μg per dose, about 10 μg to about 7,500 μg per dose, about 10 μg to about 5,000 μg per dose, about 10 μg to about 2,500 μg per dose, about 10 μg to about 1,000 μg per dose, about 10 μg to about 500 μg per dose, about 10 μg to about 250 μg per dose, about 10 μg to about 100 μg per dose, about 25 μg to about 10,000 μg per dose, about 25 μg to about 7,500 μg per dose, about 25 μg to about 5,000 μg per dose, about 25 μg to about 2,500 μg per dose, about 25 μg to about 1,000 μg per dose, about 25 μg to about 500 μg per dose, about 25 μg to about 250 μg per dose, about 25 μg to about 100 μg per dose, about 50 μg to about 10,000 μg per dose, about 50 μg to about 7,500 μg per dose, about 50 μg to about 5,000 μg per dose, about 50 μg to about 2,500 µg per dose, about 50 µg to about 1,000 µg per dose, about 50 µg to about 500 µg per dose, about 50 µg to about 250 µg per dose, about 50 µg to about 100 µg per dose, about 50 µg to about 100 µg per dose, about 75 µg to about 10,000 µg per dose, about 75 µg to about 7,500 µg per dose, about 75 µg to about 5,000 µg per dose, about 75 µg to about 2,500 µg per dose, about 75 µg to about 1,000 µg per dose, about 75 µg to about 500 µg per dose, about 75 µg to about 250 µg per dose, about 75 µg to about 125 µg per dose, about 100 µg to about 200 µg per dose, about 200 µg to about 300 µg per dose, about 300 µg to about 500 µg per dose, about 500 µg to about 1,000 µg per dose, about 1,000 µg to about 2,500 µg per dose, about 1,000 µg to about 5,000 µg per dose, about 1,000 µg to about 7,500 µg per dose, about 1,000 µg to about 10,000 µg per dose, about 2,500 µg to about 5,000 µg per dose, about 2,500 µg to about 7,500 µg per dose, about 5,000 µg to about 7,500 µg per dose, about 10,000 µg to about 50,000 µg per dose, about 50,000 µg to about 100,000 µg per dose, about 100,000 µg to about 200,000 µg per dose, about 200,000 µg to about 300,000 µg per dose, about 300,000 µg to about 400,000 µg per dose, or about 400,000 µg to about 500,000 µg per dose.

In some embodiments, the PDGF is administered at about 400 µg to about 1000 µg per dose, about 500 µg to about 900 µg per dose, about 600 µg to about 800 µg, about 650 µg to about 750 µg per dose, about 700 µg per dose.

In some embodiments, the doses provided herein are administered in a volume of 50 µL, 100 µL, 150 µL, 200 µL, 250 µL, 300 µL, 350 µL, 400 µL, 450 µL, 500 µL, 550 µL, 600 µL, 650 µL, 700 µL, 750 µL, 800 µL, 850 µL, 900 µL, 950 µL, 1000 µL or more. In some embodiments, the doses provided herein are administered in a volume of 100 µL, 200 µL, 300 µL, 400 µL, 500 µL, 600 µL, 700 µL, 800 µL, 900 µL, 1000 µL, 1100 µL, 1200 µL, 1300 µL, 1400 µL, 1500 µL, 1600 µL, 1700 µL, 1800 µL, 1900 µL, 2000 µL or more. In some embodiments, the doses provided herein are administered in a volume of about 1000 µL to about 2000 µL, about 1250 µL to about 1750 µL, about 1300 µL to about 1600 µL, or about 1500 µL.

The PDGF compositions provided herein may be administered in a single daily dose, or the total daily dose may be administered in divided dosages of, e.g., two, three, or four times daily. In some embodiments, a single daily dose of the PDGF compositions provided herein can be administered once a day for 1, 2, 3, 4, 5, 6, 7, 8, 9, 10, 11, 12, 13, 14, or more days. The PDGF compositions can also be administered less frequently than daily, for example, six times a week, five times a week, four times a week, three times a week, twice a week, once a week, once every two weeks, once every three weeks, once a month, once every two months, once every three months, once every four months, once every five months, or once every six months.

In some embodiments, the PDGF compositions are administered at intervals over a period of time. In some embodiments, the PDGF compositions are administered once a week for one, two, three, four, five, six or more months. In some embodiments, the PDGF compositions are administered twice a month for one, two, three, four, five, six or more months. In some embodiments, the PDGF compositions are administered monthly for one, two, three, four, five, six or more months.

Methods of Treating Tendinopathies

As used herein, the term "tendinopathy" refers to chronic tendon injuries such as tendinosis, tendinitis, and tenosynovitis. Exemplary tendinopathies include, but are not limited to, Achilles tendinopathy, patellar tendinopathy, lateral epicondylitis, or "tennis elbow," medial epicondylitis, plantar fasciitis, and rotator cuff tendinopathy.

As used herein, the term "tendinosis" refers to a non-inflammatory injury to the tendon characterized by intratendinous degeneration of the tendon usually in the form of microtears in the tissue in and around the tendon caused by overuse, leading to an increase in the number of tendon repair cells around the area of damage. Degeneration of the tendon is caused by damage to or disorganization of the collagen fibers, cells, and vascular components of the tendon, which can reduce the tendon's tensile strength and can lead to tendon rupture if not treated. In some cases, tendinosis is accompanied by focal necrosis or calcification of the tendon.

As used herein, the term "tendinitis" refers to an inflammatory injury to the tendon, characterized by degeneration like that observed in tendinosis, but also accompanied by inflammation of the tendon, vascular disruption and an inflammatory repair response. Tendinitis is often associated with fibroblastic and myofibroblastic proliferation, as well as hemorrhage and organizing granulation tissue. Generally tendinitis is referred to by the body part involved, such as Achilles tendinitis (affecting the Achilles tendon), or patellar tendinitis (also known as "jumper's knee," affecting the patellar tendon), though there are certain exceptions, such as lateral epicondylitis (also known as "tennis elbow," affecting the Extensor Carpi Radialis Brevis tendon).

Tendinopathies which may be treated by the methods of the invention include tendinopathies of any tendon in the human or mammalian body. In some embodiments, the tendinopathy is tendinosis. In some embodiments, the tendinopathy is tendinitis. In some embodiments, the tendinopathy is tenosynovitis.

Tendons which may be treated by the methods of the invention include any tendon of the human or mammalian body. Non-limiting examples of tendons include the patellar tendon, the anterior tibialis tendon, the Achilles tendon, the hamstring tendon, the semitendinosus tendon, the gracilis tendon, the abductor tendon, the adductor tendon, the supraspinatus tendon, the infraspinatus tendon, the subscapularis tendon, the teres minor tendon, the flexor tendon, the rectus femoris tendon, the tibialis posterior tendon, and the quadriceps femoris tendon.

In some embodiments, the tendon is a tendon of the foot or ankle. In some embodiments, the tendon of the foot or ankle is selected from the group consisting of the extensor hallucis longus, the flexor hallucis longus, the extensor digitorum longus, the extensor digitorum brevis, the peroneus longus, the peroneus brevis, the flexor hallucis brevis, the flexor digitorum longus, the posterior tibialis, the Achilles tendon, and the plantar fascia.

In some embodiments, the tendon is a tendon of the leg. In some embodiments, the tendon of the leg is selected from the group consisting of the patellar tendon, the anterior tibialis tendon, the Achilles tendon, the hamstring tendon, the semitendinosus tendon, the gracilis tendon, the abductor tendon, and the adductor tendon. In some embodiments, the tendon is selected from the group consisting of the flexor tendon, the rectus femoris tendon, the tibialis posterior tendon, and the quadriceps femoris tendon.

In some embodiments, the tendon is a tendon of the shoulder. In some embodiments, the tendon of the shoulder is selected from the group consisting of the supraspinatus tendon, the infraspinatus tendon, the subscapularis tendon, and the teres minor tendon (rotator cuff complex).

In some embodiments, the tendon is a tendon of the elbow. In some embodiments, the tendon of the elbow is selected from the group consisting of the biceps tendon, the triceps tendon, the extensor carpi radialis brevis, the common extensor tendon, the extensor digitorum, the extensor digiti minimi, the extensor carpi ulnaris, the supinator, the common flexor tendon, the pronator teres, the flexor carpi radialis, the palmaris longus, the flexor carpi ulnaris and the digitorum superficialis. In some embodiments, the tendon is a tendon of the wrist. In some embodiments, the tendon of the wrist is selected from the group consisting of biceps tendon, the triceps tendon, the extensor carpi radialis brevis, the common extensor tendon, the extensor digitorum, the extensor digiti minimi, the extensor carpi ulnaris, the supinator, the common flexor tendon, the pronator teres, the flexor carpi radialis, the palmaris longus, the flexor carpi ulnaris, the digitorum superficialis, the flexor pollicis brevis, the flexor pollicis longus, the abductor pollicis brevis, the abductor pollicis longus, the flexor digitorum profundus, the flexor digitorum superficialis, the extensor pollicis brevis, and the extensor pollicis longus. In some embodiments, the tendon is a tendon of the hand. In some embodiments, the tendon of the hand is selected from the group consisting of the flexor pollicis brevis, the flexor pollicis longus, the abductor pollicis brevis, the abductor pollicis longus, the flexor digitorum profundus, the flexor digitorum superficialis, the extensor pollicis brevis, and the extensor pollicis longus.

In some embodiments, the tendinopathy is rotator cuff tendinopathy. In some embodiments, the rotator cuff tendinopathy is selected from the group consisting of supraspinatus tendinopathy, infraspinatus tendinopathy, subscapularis tendinopathy, and teres minor tendinopathy.

In some embodiments, the tendinopathy is lateral epicondylitis or "tennis elbow" at the extensor muscle group origin at the lateral humeral condyle insertion, principally in the extensor carpi radialis brevis (ECRB) tendon. In some embodiments, the subject having lateral epicondylitis has associated pain (e.g. for at least about six months) as evidenced by pain reported to be ≥50 on a Visual Analog Score (VAS). In some embodiments, the subject having lateral epicondylitis has associated pain that increases with pressure on the lateral epicondyle and/or resisted extension of the wrist, e.g. for at least about six months. In some embodiments, the tendinopathy is medial epicondylitis or "golfer's elbow" at the interface between the pronator teres and flexor carpi radialis origin of the medial humeral condyle.

In some embodiments, the tendinopathy is patellar tendinopathy. In some embodiments, the tendinopathy is Achilles tendinopathy. In some embodiments, the tendinopathy is plantar fasciitis. In some embodiments, the tendinopathy is medial plantar fasciitis. In some embodiments, the tendinopathy is lateral plantar fasciitis.

In another aspect, provided herein are methods of treating tendinopathies comprising administering an effective amount of a composition comprising PDGF and a buffer to an affected site. In some embodiments, the PDGF is selected from the group consisting of PDGF-AA, PDGF-BB, PDGF-AB, PDGF-CC, and PDGF-DD. In some embodiments, the PDGF is PDGF-BB. In some embodiments, the effective amount of the composition comprises between about 75 µg and about 7,500 µg of PDGF-BB per dose. In some embodiments, the effective amount of the composition comprises between about 500 µg to about 1,000 µg of PDGF-BB per dose. In some embodiments, the effective amount of the composition comprises between about 450 µg to about 3,000 µg of PDGF per dose. In some embodiments, the effective amount of the composition comprises between about 5,000 µg to about 7,500 µg of PDGF-BB per dose.

In some embodiments, the buffer is selected from the group consisting of phosphate-buffered saline ("PBS"), sodium acetate, ammonium acetate, acetic acid, citric acid, sodium citrate, tris(hydroxymethyl)aminoethane ("tris"), N-2-hydroxyethylpiperazine-N'-2-ethanesulfonic acid ("HEPES"), 3-(N-morpholino) propanesulfonic acid ("MOPS"), 2-(N-morpholino)ethanesulfonic acid ("MES"), N-(2-acetamido)iminodiacetic acid ("ADA"), piperazine-N, N'-bis(2-ethanesulfonic acid) ("PIPES"), and N-(2-acetamido)-2-aminoethanesulfonic acid ("ACES"). In some embodiments, the buffer is sodium acetate. In some embodiments, the sodium acetate is at a concentration between about 10 mM and about 100 mM. In some embodiments, the sodium acetate is at a concentration of about 20 mM. In some embodiments, the sodium acetate is at a pH between about 4.0 and about 7.0. In some embodiments, the sodium acetate is at about pH 6.

In some embodiments, the administering is by direct injection to the affected site. In some embodiments, the direct injection is accomplished using the "peppering technique" with or without ultrasound guidance. The "peppering technique" is an injection method whereby after the needle is inserted into the tender area, multiple small injections are performed by withdrawing, redirecting and reinserting the needle without emerging from the skin.

In some embodiments, the affected site is an osseous-tendon junction. In some embodiments, the affected site is a tendon. In some embodiments, the tendinopathy is selected from the group consisting of Achilles tendinopathy, patellar tendinopathy, lateral epicondylitis, medial epicondylitis, plantar fasciitis, and rotator cuff tendinopathy. In some embodiments, the composition is administered by a single injection. In some embodiments, the composition is administered by a single injection once a week for four weeks.

In some embodiments, the tendinopathy is tendinosis. In some embodiments, the tendinosis is selected from the group consisting of extensor hallucis longus tendinosis, flexor hallucis longus tendinosis, extensor digitorum longus tendinosis, extensor digitorum brevis tendinosis, peroneus longus tendinosis, peroneus brevis tendinosis, flexor hallucis brevis tendinosis, flexor digitorum longus tendinosis, posterior tibialis tendinosis, Achilles tendon tendinosis, and plantar fascia tendinosis. In some embodiments, the tendinosis is selected from the group consisting of patellar tendinosis, the anterior tibialis tendinosis, the hamstring tendinosis, semitendinosus tendinosis, gracilis tendinosis, abductor tendinosis, and adductor tendinosis. In some embodiments, the tendinosis is selected from the group consisting of flexor tendinosis, rectus femoris tendinosis, tibialis posterior tendinosis, and quadriceps femoris tendinosis. In some embodiments, the tendinosis is selected from the group consisting of supraspinatus tendinosis, infraspinatus tendinosis, subscapularis tendinosis, and teres minor tendinosis.

In some embodiments, the tendinosis is selected from the group consisting of biceps tendinosis, triceps tendinosis, extensor carpi radialis brevis tendinosis, common extensor tendinosis, extensor digitorum tendinosis, extensor digiti minimi tendinosis, extensor carpi ulnaris tendinosis, supinator tendinosis, common flexor tendinosis, pronator teres tendinosis, flexor carpi radialis tendinosis, palmaris longus tendinosis, flexor carpi ulnaris tendinosis and digitorum superficialis tendinosis. In some embodiments, the tendinosis is selected from the group consisting of biceps tendinosis, triceps tendinosis, extensor carpi radialis brevis tendinosis, common extensor tendinosis, extensor digitorum tendinosis, extensor digiti minimi tendinosis, extensor carpi ulnaris tendinosis, supinator tendinosis, common flexor tendinosis, pronator teres tendinosis, flexor carpi radialis tendinosis, palmaris longus tendinosis, flexor carpi ulnaris tendinosis, digitorum superficialis tendinosis, flexor pollicis brevis tendinosis, flexor pollicis longus tendinosis, abductor pollicis brevis tendinosis, abductor pollicis longus tendinosis, flexor digitorum profundus tendinosis, flexor digitorum superficialis tendinosis, extensor pollicis brevis tendinosis, and extensor pollicis longus tendinosis. In some embodiments, the tendinosis is selected from the group consisting of flexor pollicis brevis tendinosis, flexor pollicis longus tendinosis, abductor pollicis brevis tendinosis, abductor pollicis longus tendinosis, flexor digitorum profundus tendinosis, flexor digitorum superficialis tendinosis, extensor pollicis brevis tendinosis, and extensor pollicis longus tendinosis.

In some embodiments, the tendinopathy is tendinitis. In some embodiments, the tendinitis is selected from the group consisting of extensor hallucis longus tendinitis, flexor hallucis longus tendinitis, extensor digitorum longus tendinitis, extensor digitorum brevis tendinitis, peroneus longus tendinitis, peroneus brevis tendinitis, flexor hallucis brevis tendinitis, flexor digitorum longus tendinitis, posterior tibialis tendinitis, Achilles tendon tendinitis, and plantar fascia tendinitis. In some embodiments, the tendinitis is selected from the group consisting of patellar tendinitis, the anterior tibialis tendinitis, the hamstring tendinitis, semitendinosus tendinitis, gracilis tendinitis, abductor tendinitis, and adductor tendinitis. In some embodiments, the tendinitis is selected from the group consisting of flexor tendinitis, rectus femoris tendinitis, tibialis posterior tendinitis, and quadriceps femoris tendinitis. In some embodiments, the tendinitis is selected from the group consisting of supraspinatus tendinitis, infraspinatus tendinitis, subscapularis tendinitis, and teres minor tendinitis.

In some embodiments, the tendinitis is selected from the group consisting of biceps tendinitis, triceps tendinitis, extensor carpi radialis brevis tendinitis, common extensor tendinitis, extensor digitorum tendinitis, extensor digiti minimi tendinitis, extensor carpi ulnaris tendinitis, supinator tendinitis, common flexor tendinitis, pronator teres tendinitis, flexor carpi radialis tendinitis, palmaris longus tendinitis, flexor carpi ulnaris tendinitis and digitorum superficialis tendinitis. In some embodiments, the tendinitis is selected from the group consisting of biceps tendinitis, triceps tendinitis, extensor carpi radialis brevis tendinitis, common extensor tendinitis, extensor digitorum tendinitis, extensor digiti minimi tendinitis, extensor carpi ulnaris tendinitis, supinator tendinitis, common flexor tendinitis, pronator teres tendinitis, flexor carpi radialis tendinitis, palmaris longus tendinitis, flexor carpi ulnaris tendinitis, digitorum superficialis tendinitis, flexor pollicis brevis tendinitis, flexor pollicis longus tendinitis, abductor pollicis brevis tendinitis, abductor pollicis longus tendinitis, flexor digitorum profundus tendinitis, flexor digitorum superficialis tendinitis, extensor pollicis brevis tendinitis, and extensor pollicis longus tendinitis. In some embodiments, the tendinitis is selected from the group consisting of flexor pollicis brevis tendinitis, flexor pollicis longus tendinitis, abductor pollicis brevis tendinitis, abductor pollicis longus tendinitis, flexor digitorum profundus tendinitis, flexor digitorum superficialis tendinitis, extensor pollicis brevis tendinitis, and extensor pollicis longus tendinitis.

The methods of the invention may result in improvement in one or more of the following: decreasing pain of the affected joint or limb, decreasing stiffness of the affected joint or limb, increasing mobility of the affected joint or limb, increasing strength of the affected joint or limb, decreasing the rate of tendinopathy progression, decreasing inflammation, increasing the strength of the tendon, or improving the rate of tendon strength recovery. Various methods for measuring effectiveness of the treatment include, but are not limited to: Disabilities of the Arm, Shoulder and Hand Score (DASH), Visual Analog Score (VAS), and grip strength testing. In some embodiments, the treatment results in at least a 25% reduction in pretreatment score for DASH. In some embodiments, the treatment results in at least a 25% reduction in pretreatment score for VAS. In some embodiments, the treatment produces a decrease in pain with applied pressure and/or joint flexion. In some embodiments, the treatment produces a decrease in pain with applied pressure and/or joint flexion and an increase in joint mobility. In some embodiments, the treatment does not result in any abnormal bone growth. In some embodiments, the treatment does not result in any abnormal tendon growth. In some embodiments, the treatment is safe and tolerated by the subject. In some embodiments, safety and tolerability of the composition is evaluated by the lack of an adverse event or an abnormality identified by one or more of the following: physical examination, vital sign measurement, laboratory test, x-ray, and/or MRI imaging.

In some embodiments, the treatment results in increased strength of the tendon. In some embodiments, the treatment results in a more rapid rate of tendon strength recovery. In some embodiments, the treatment results in an increase in tendon strength of at least about 30%, at least about 40%, at least about 50%, at least about 60%, at least about 70% within about 4, 5, 6, 7, 8, 9, 10, 11, 12, 13, 14, 15, 16, 17, 18, 19, 20, or 21 days of administration of a composition of the invention, as compared to baseline. In some embodiments, the treatment results in an increase in tendon strength of at least about 30%, at least about 40%, at least about 50%, at least about 60%, at least about 70% within about 7 days of administration of a composition of the invention, as compared to baseline. In some embodiments, the treatment results in an increase in tendon strength of at least about 60% within about 7 days of administration of a composition of the invention, as compared to baseline. In some embodiments, the treatment results in an increase in tendon strength of at least about 65% within about 7 days of administration of a composition of the invention, as compared to baseline. In some embodiments, the treatment results in an increase in tendon strength of at least about 70% within about 7 days of administration of a composition of the invention, as compared to baseline. In some embodiments, the tendon achieves at least about 60%, at least about 70%, at least about 80%, at least about 90%, at least about 95% of its final strength within about 4, 5, 6, 7, 8, 9, 10, 11, 12, 13, or 14 days of administration of a composition of the invention, wherein final strength is measured at about 21 days after treatment. In some embodiments, the tendon achieves at least about 80% of its final strength within about 7 days of administration of a composition of the invention, wherein final strength is measured at about 21 days after treatment. In some embodiments, the tendon achieves at least about 85% of its final strength within about 7 days of administration of a composition of the invention, wherein final strength is measured at about 21 days after treatment. In some embodiments, the tendon achieves at least about 90% of its final strength within about 7 days of administration of a composition of the invention, wherein final strength is measured at about 21 days after treatment. Tendon strength can be measured, for example, in an animal model, for example in a rat collagenase model, wherein the tendon strength is the measured load to rupture. An example of measurement of tendon strength is described in more detail in Example 3.

Kits

In another aspect, provided herein are kits comprising a container containing a composition comprising PDGF and a buffer. In some embodiments, the kits comprise a first container containing a lyophilized PDGF and a second container containing a buffer for solubilizing the lyophilized PDGF. In some embodiments, the kits comprise a first container containing a lyophilized PDGF and buffer, and a second container containing water for solubilizing the lyophilized PDGF and buffer. In some embodiments, the buffer is selected from the group consisting of phosphate-buffered saline ("PBS"), sodium acetate, ammonium acetate, acetic acid, citric acid, sodium citrate, tris(hydroxymethyl)aminoethane ("tris"), N-2-hydroxyethylpiperazine-N'-2-ethanesulfonic acid ("HEPES"), 3-(N-morpholino) propanesulfonic acid ("MOPS"), 2-(N-morpholino)ethanesulfonic acid ("MES"), N-(2-acetamido)iminodiacetic acid ("ADA"), piperazine-N,N'-bis(2-ethanesulfonic acid) ("PIPES"), and N-(2-acetamido)-2-aminoethanesulfonic acid ("ACES"). In some embodiments, the buffer is sodium acetate. In some embodiments, the sodium acetate is at a concentration between about 10 mM and about 100 mM. In some embodiments, the sodium acetate is at a concentration of about 20 mM. In some embodiments, the sodium acetate is at a pH between about 4.0 and about 7.0. In some embodiments, the sodium acetate is at about pH 6.

In some embodiments, the kits further include other materials desirable from a commercial, therapeutic, and user standpoint, including other buffers, diluents, filters, needles, syringes, and package inserts with instructions for use. As used herein, the term "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments.

Sutures

Also provided are PDGF coated sutures, and methods of making such sutures. The sutures may be used, for example, in treating a tendon in an individual (e.g. treating a tendon tear). Suitable sutures include, for example, those made from co-polymers of lactide and glycolide (such as Vicryl sutures (e.g. 4-0 Vicryl sutures)). Suitable coating methods include, for example, dip coating methods, such as the dip coating method described in Dines J, Weber L, Razzano P, et al. The Effect of Growth Differentiation Factor-5-Coated Sutures on Tendon Repair in a Rat Model. J Shoulder Elbow Surg 2007; 16:215S-221S), which may optionally be altered to eliminate the gelatin. The applicants have surprisingly found that high doses of PDGF may be coated onto certain types of sutures in absence of gelatin. In some embodiments, the suture does not comprise gelatin. In some embodiments, the suture coating does not comprise gelatin. In some embodiments, the suture coating does not comprise polylactic, polyglycolic, or poly(lactic-co-glycolic) acid. In some embodiments, the method of coating the suture does not comprise utilizing gelatin. In some embodiments, the suture coating consists essentially of PDGF. In some embodiments, the suture coating consists of PDGF and a buffer. In some embodiments, the suture coating consists of PDGF. The sutures may be used to treat an individual, for example, a mammal. Non-limiting examples of mammals which may be treated using a suture of the invention include humans, pets (e.g. dogs, cats, rabbits, hamsters, etc.), laboratory animals (e.g. mice, rats), farm animals (e.g. horses, cows, sheep, goats, etc.).

In some embodiments, the amount of PDGF loaded onto the suture is at least about 10 ng PDGF/cm suture. In some embodiments, the amount of PDGF loaded onto the suture is at least about 100 ng PDGF/cm suture. In some embodiments, the amount of PDGF loaded onto the suture is at least about 1000 ng PDGF/cm suture. In some embodiments, the amount of PDGF loaded onto the suture is at least about 5000 ng PDGF/cm suture. In some embodiments, the amount of PDGF loaded onto the suture is at least about 6000 ng PDGF/cm suture. In some embodiments, the amount of PDGF loaded onto the suture is about 10 to about 20,000 ng PDGF/cm suture. In some embodiments, the amount of PDGF loaded onto the suture is about 100 to about 10,000 ng PDGF/cm suture. In some embodiments, the amount of PDGF loaded onto the suture is about 500 to about 8,000 ng PDGF/cm suture. In some embodiments, the amount of PDGF loaded onto the suture is about 1000 to about 8,000 ng PDGF/cm suture. In some embodiments, the amount of PDGF loaded onto the suture is about 4000 to about 8,000 ng PDGF/cm suture. In some embodiments, the amount of PDGF loaded onto the suture is about 6000 to about 7,000 ng PDGF/cm suture.

In some embodiments, the cumulative amount of PDGF released from the suture over 48-hours as measured in vitro is at least about 10 ng PDGF/cm suture. In some embodiments, the cumulative amount of PDGF released from the suture over 48-hours as measured in vitro is at least about 100 ng PDGF/cm suture. In some embodiments, the cumulative amount of PDGF released from the suture over 48-hours as measured in vitro is at least about 1000 ng PDGF/cm suture. In some embodiments, the cumulative amount of PDGF released from the suture over 48-hours as measured in vitro is at least about 5000 ng PDGF/cm suture. In some embodiments, the cumulative amount of PDGF released from the suture over 48-hours as measured in vitro is at least about 6000 ng PDGF/cm suture. In some embodiments, the cumulative amount of PDGF released from the suture over 48-hours as measured in vitro is about 10 to about 20,000 ng PDGF/cm suture. In some embodiments, the cumulative amount of PDGF released from the suture over 48-hours as measured in vitro is about 100 to about 10,000 ng PDGF/cm suture. In some embodiments, the cumulative amount of PDGF released from the suture over 48-hours as measured in vitro is about 500 to about 8,000 ng PDGF/cm suture. In some embodiments, the cumulative amount of PDGF released from the suture over 48-hours as measured in vitro is about 1000 to about 8,000 ng PDGF/cm suture. In some embodiments, the cumulative amount of PDGF released from the suture over 48-hours as measured in vitro is about 4000 to about 8,000 ng PDGF/cm suture. In some embodiments, the cumulative amount of PDGF released from the suture over 48-hours as measured in vitro is about 6000 to about 7,000 ng PDGF/cm suture. Suitable methods of measuring cumulative PDGF release in vitro include, for example, the method described in Example 7. The coated sutures of the invention may advantageously provide for consistent dosing in vivo.

The following examples are provided for illustrative purposes only and are not intended to limit the scope of the invention in any manner.

EXAMPLES

Example 1: Normal and Diseased Primary Human Tenocytes Proliferate in Response to rhPDGF-BB This study determined whether rhPDGF-BB directly activated proliferation and/or chemotaxis of primary tenocytes derived from patients with tendinopathies. Such findings can support the notion of therapeutic potential of rhPDGF-BB in tendinopathies.

Patients and Methods

Patients

Ten patients with tendinopathies were involved in this study, including five patients with Achilles tendinopathy and five patients with tendinopathy of the posterior tibial tendon (PTT). An additional five patients were involved who underwent full joint replacement of the knee.

Primary Cultures of Tenocytes

Tendon tissue which would otherwise be discarded was obtained from normal and injured tendons during reconstructive surgery procedures performed for clinical indications. These tissues included the tendinopathic portion of the Achilles or PTT tendons, as well as the healthy (non-tendinopathic) portion of the flexor digitorum longus (FDL) tendon tissue, Achilles tendon tissue, and Patellar tendon tissue. Primary tenocyte explant cultures were obtained from these tissues and tested at passages 3 to 5. Tenocyte identity was confirmed by assessing the expression of a tenocyte-specific gene scleraxis and genes for collagens $\alpha 1$ (I), $\alpha 2$(I), and $\alpha 1$(III) in real-time PCR assays with specific primers.

Cell Proliferation

Tenocyte monolayers were trypsinized, resuspended in DMEM/F12 medium containing 0.5% dialyzed fetal bovine serum, allowed to attach overnight, and then incubated with titrated concentrations of rhPDGF-BB for 24 hours. Changes in cell proliferation rates were assessed based on BrdU incorporation during DNA synthesis in cells using a commercially available assay (Roche Applied Science, Indianapolis, Ind.). Each culture was tested in triplicates for each dose of rhPDGF-BB.

Cell Migration

Tenocyte monolayers were trypsinized, resuspended in DMEM/F12 medium containing 0.5% dialyzed fetal bovine serum and placed in the upper chamber of the 96-well ChemoTx® disposable cell migration system (Neuro Probe, Gaithersburg, Md.). The lower chambers contained titrated concentrations of rhPDGF-BB. Tenocytes were allowed to migrate across the membrane separating the chambers for 48 hours. 96-well plates were then spun down and freeze thawed three times to lyse the migrated cells. The amount of viable migrated cells was measured based on cytoplasmic lactate dehydrogenase (LDH) using a commercially available kit from Promega (Madison, Wis.).

Statistical Analysis

One-way ANOVA was used to determine whether stimulation with rhPDGF-BB affects tenocyte proliferation in a dose-dependent fashion.

Results

Only tenocyte cultures but not control pulmonary fibroblast cultures or control primary T lymphocyte cultures expressed scleraxis mRNA, whereas tenocytes and fibroblasts but not lymphocytes expressed the collagen gene mRNAs.

Figure 2:
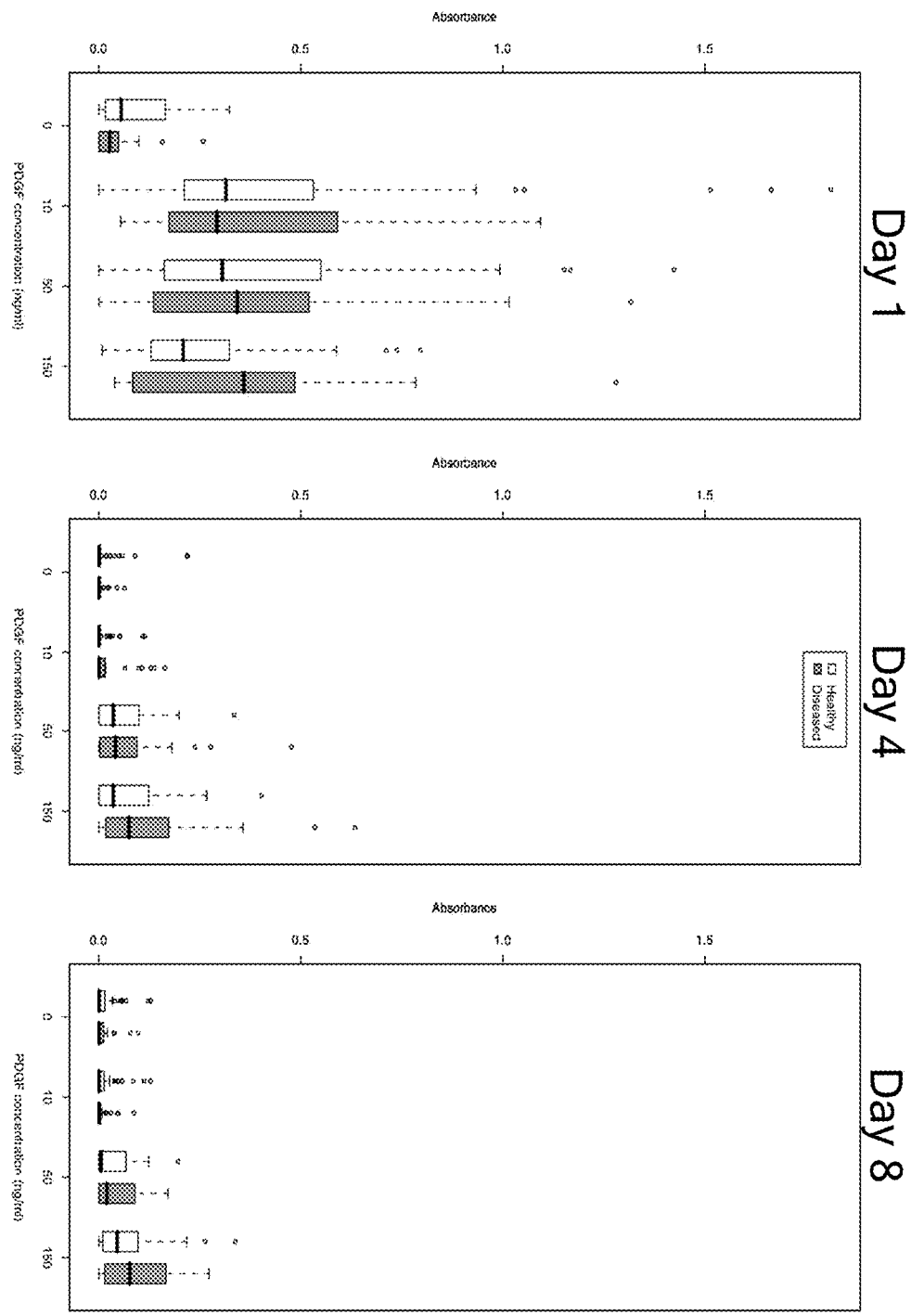
FIG. 2 shows the effect of rhPDGF-BB treatment on tenocyte cell proliferation as measured by BrdU incorporation.

In all cases, tenocytes from tendon tissues involved or not involved in the disease process responded to rhPDGF-BB stimulation by accelerating BrdU incorporation ($p<0.05$, one-way ANOVA). The responses were dose-dependent and were observed at 10, 50 and 150 ng/mL of rhPDGF-BB. Even though all cell cultures responded to rhPDGF-BB stimulation, there was significant variability among patients in the magnitude of BrdU incorporation after rhPDGF-BB stimulation. Incorporation of BrdU increased from a minimum of $2.1\pm0.2$ fold to a maximum of $10.7\pm0.5$ fold compared to control non-stimulated cultures. Tenocytes from five patients responded paradoxically, with a greater increase in BrdU incorporation at a lower (10 ng/mL) rather than higher (50 and 150 ng/mL) concentrations of rhPDGF-BB. Such paradoxic response was observed in tenocytes derived from both tendinopathic and normal tissues of these patients. Tenocytes derived from healthy tendons of four patients incorporated twice more BrdU in response to rhPDGF-BB stimulation than did tenocytes derived from the diseased tissues. In one patient, tenocytes from the diseased tissue incorporated four fold more BrdU in response to rhPDGF stimulation than did tenocytes from the tissue uninvolved in the disease process. FIG. 2 shows the BrdU incorporation (y-axis, absorbance) for 0, 10, 50, and 150 ng/ml of PDGF added to the culture medium at day 1, day 4, and day 8 for healthy and diseased tenocytes. An increase in absorbance corresponds with increased proliferation, with both the healthy and diseased tenocytes responding to PDGF on day 1.

In all cases, tenocytes were chemotactically responsive to rhPDGF-BB at 50 ng/mL and 150 ng/mL. Tenocytes were not exposed to 10 ng/mL rhPDGF-BB for chemotaxis experiments because of low response in pilot experiments. Again, responses were dose-dependent, with greater chemotaxis to 150 ng/mL than to 50 ng/mL of rhPDGF-BB. However, tenocytes from 5 patients responded with greater chemotaxis to 50 ng/mL than to 150 ng/mL of rhPDGF-BB, with significant decline in the number of migrated cell ($p<0.05$, two-sided Student's t-test). There was variability among patients in the maximal chemotactic response to rhPDGF-BB, from $1.4\pm0.1$ to $4.0\pm0.5$ fold increase compared to non-stimulated control. There was no statistically significant difference ($p>0.05$) in tenocyte chemotaxis to rhPDGF-BB within matching tenocyte cultures derived from tendinopathic or from healthy tendon tissues. FIG. 1 shows the chemotaxis of cells (y-axis shows increased optical density) cultured in concentrations of 0, 50, or 150 ng/ml of PDGF. Migration was assessed with 1250, 2500, 5000, and 10000 initial cells.

Conclusion

The results of these experiments suggest that tenocytes derived from healthy and tendinopathic tissues respond to rhPDGF-BB by increasing proliferation and chemotaxis rates.

Importantly, tenocytes from some patients showed paradoxical response to PDGF, in which higher doses caused less effect than lower doses. Equally important, tenocytes from diseased tendons were in some cases differentially responsive to PDGF versus tenocytes from healthy tendons, implying that proper dosing may be of paramount importance in the clinical setting.

Example 2: Safety Studies with rhPDGF-BB

Local Injection Test.

The purpose of this study was to determine the local toxicity of rhPDGF-BB following an intra-Achilles tendon delivery to rats. The intra-Achilles tendon administration mimics the route of administration of rhPDGF-BB in the clinic for the treatment of lateral epicondylitis. The injection site at the Achilles tendon-calcaneous junction mimics the insertion site of the extensor carpi radialis brevis tendon and lateral epicondyle bone.

The study used Sprague Dawley rats. The animals were housed at the same lab facility for the duration of the study. All housing and husbandry were in accordance with the Animal Welfare Act and the "Guide for the Care and Use of Laboratory Animals". Rats were fed and watered in accordance with standard protocols. Food and water were withheld for appropriate study related events such as anesthesia. Animals were acclimated to the facility for a minimum of 5 days prior to the study. This acclimation period allows the animals to become accustomed to the study room setting.

Three batches of sterile recombinant human PDGF-BB at different concentrations were used in the study: (1) 10.3 mg/ml rhPDGF-BB in 20 mM sodium acetate buffer, pH 6.0±0.5; (2) 5.2 mg/ml rhPDGF-BB in 20 mM sodium acetate buffer, pH 6.0±0.5; and (3) 1.7 mg/ml rhPDGF-BB in 20 mM sodium acetate buffer, pH 6.0±0.5. The vehicle control sample was sterile 20 mM sodium acetate buffer, pH 6.0±0.5, and was prepared according to standard procedures.

Standard laboratory safety procedures were employed for handling the test and control articles. Specifically, gloves, facemask, gown (or lab coat) and eye protection were worn while preparing and administering doses.

Animals were randomized into four groups, with n=60 per group, with each group having 30 males and 30 females. The groups each received a single intra-tendon injection at the osteotendinous junction of the quadriceps muscle of the following compounds: (1) 20 mM sodium acetate; (2) 51 µg rhPDGF-BB in 20 mM sodium acetate; (3) 156 µg rhPDGF-BB in 20 mM sodium acetate; or (4) 515 µg rhPDGF-BB in 20 mM sodium acetate. Injections were performed with insulin syringes equipped with a 28.5 G needle. All animals received test article on Day 1 via a single intra-Achilles tendon injection. Group 1 animals received sodium acetate (NaOAc), while Group 2-4 animals received rhPDGF-BB at dose levels of 36.69, 112.23, and 370.50 µg/mm2, respectively.

One third of each group was sacrificed at 1 day, 2 weeks, and 6 weeks post-rhPDGF-BB injection. Upon completion of the in-life treatment groups, animals were euthanized and tissues harvested in accordance with the USDA Animal Welfare Act, The Guide for Care and Use of Laboratory Animals (ILAR publication, 1996, National Academy Press), and HSS veterinary procedures. Animals were euthanized by $CO_2$ overdose. Death was confirmed by lack of reflexes (blinking, withdrawal, etc.).

Criteria for evaluation included clinical observations, physical evaluations, body weight and food consumption measurements, clinical pathology, necropsy, organ weights, and histopathology evaluation of the injected and noninjected hind leg ankles, including an examination of tendon toxicity and bone toxicity.

Animals underwent a hematological assessment, a coagulation study, and a variety of clinical chemistry studies. The hematological assessment included the following measures: a leukocyte count (WBC); an erythrocyte Count (RBC); determination of hemoglobin (Hb), mean corpuscular hemoglobin (MCH) levels, hematocrit (HCT), and mean corpuscular Hb concentration (MCHC); a platelet count; determination of mean corpuscular volume (MCV), and an assessment of leukocyte differential, including neutrophil, lymphocyte, monocyte, eosinophil, basophil, % neutrophil, % lymphocyte, % monocyte, and % eosinophil). The coagulation study measured activated partial thromboplastin time (APTT) and prothrombin time (PT). Clinical chemistry studies included analysis of the following: alkaline phosphatase (ALP), glucose (GLU), albumin (ALB), alanine aminotransferase (ALT), total bilirubin (TBIL), globulin (Glob), aspartate aminotransferase (AST), cholesterol (CHOL), potassium (K), gamma glutamyltransferase (GGT), triglycerides (TRIG), chloride (Cl), creatinine (CREAT), blood urea nitrogen (BUN), sodium (Na), inorganic phosphorus (PHOS), calcium (Ca), A/G ratio, and total protein (TPROT).

Results

Single intra-Achilles tendon injection of rhPDGF-BB to rats at dose levels 36.69 µg/mm2, 112.23 µg/mm2, 370.50 µg/mm2 had no effect on mortality or moribundity. Furthermore, there were no test article-associated biologically significant differences in clinical observations, effects on body weight, or food consumption.

On Day 2, there were no statistically or biologically significant differences in any of the hematology or urinalysis parameters analyzed for the any of the groups of treated rats when compared to the controls (Group 1). Changes were observed in leukocyte and coagulation parameters, but these changes were consistent with a minimal acute inflammatory response to the injection of a foreign protein. In addition, minimal changes were also observed in several serum chemistry parameters. However, these changes were considered to be the result of individual animal variation, were not considered to be biologically significant, and were not associated with any organ specific toxicity.

On Days 16 and 43, there were no biologically significant differences in any of the hematology, leukocyte, coagulation, or urinalysis parameters analyzed for the any of the groups of treated rats when compared to the controls (Group 1).

There were no test article-associated macroscopic observations; all macroscopic observations were considered to be incidental.

Acute hemorrhage and subacute inflammation was observed on Day 2 in the controls and the treated groups of rats, although the frequency and severity appeared to greater in the treated groups of rats. On Day 16, acute hemorrhage has subsided and subacute inflammation was infrequent. Treated groups of rats demonstrated fibroplasia and neovascularization of the paratendons of the superficial flexor tendon and calcaneal tendon in addition to hypertrophy and hyperplasia of tenocytes of the aforementioned tendons. By Day 43, the severity of the fibroplasia and neovascularization had ameliorated; tenocytes still demonstrated hypertrophy and hyperplasia in the majority of treated rats.

Second Species Local Injection Test.

The objective of this study is to determine the local toxicity of recombinant human platelet-derived growth factor (rhPDGF-BB) following intra-Achilles tendon delivery to dogs.

The study uses Beagle dogs. The animals are housed at the same lab facility for the duration of the study. All housing and husbandry is in accordance with the Animal Welfare Act and the "Guide for the Care and Use of Laboratory Animals". Dogs are fed and watered in accordance with standard protocols. Food and water are withheld for appropriate study related events such as anesthesia. Animals are acclimated to the facility for a minimum of 5 days prior to the study. This acclimation period allows the animals to become accustomed to the study room setting.

Three batches of sterile recombinant human PDGF-BB at different concentrations are used in the study: (1) 10 mg/ml rhPDGF-BB in 20 mM sodium acetate buffer, pH 6.0±0.5; (2) 3 mg/ml rhPDGF-BB in 20 mM sodium acetate buffer, pH 6.0±0.5; and (3) 1 mg/ml rhPDGF-BB in 20 mM sodium acetate buffer, pH 6.0±0.5. The vehicle control sample is sterile 20 mM sodium acetate buffer, pH 6.0±0.5, and is prepared according to standard procedures.

Standard laboratory safety procedures are employed for handling the test and control articles. Specifically, gloves, facemask, gown (or lab coat) and eye protection are worn while preparing and administering doses.

Animals are randomized into four groups, with n=24 per group, with each group having 12 males and 12 females. The groups each receive a single intra-tendon injection at the osteotendinous junction of the quadriceps muscle of the following compositions: (1) 20 mM sodium acetate; (2) 1.5 mg rhPDGF-BB in 20 mM sodium acetate; (3) 4.5 mg rhPDGF-BB in 20 mM sodium acetate; or (4) 15 mg rhPDGF-BB in 20 mM sodium acetate. Injections are performed with insulin syringes equipped with a 28.5 G needle with a fixed dose volume of 1.5 ml.

One third of each group is sacrificed at 1 day, 2 weeks, and 6 weeks post-rhPDGF-BB injection. Upon completion of the in-life treatment groups, animals are euthanized and tissues harvested in accordance with the USDA Animal Welfare Act, The Guide for Care and Use of Laboratory Animals (ILAR publication, 1996, National Academy Press), and HSS veterinary procedures. Animals are euthanized by exsanguination while under deep anesthesia induced with sodium pentobarbital (Fatal-Plus® or an appropriate alternative).

Animals undergo a hematological assessment, a coagulation study, and a variety of clinical chemistry studies.

The hematological assessment includes the following measures: a leukocyte count (WBC); an erythrocyte Count (RBC); determination of hemoglobin (Hb), mean corpuscular hemoglobin (MCH) levels, hematocrit (HCT), and mean corpuscular Hb concentration (MCHC); a platelet count; determination of mean corpuscular volume (MCV), and an assessment of leukocyte differential, including neutrophil, lymphcyte, monocyte, eosinophil, basophil, % neutrophil, % lymphocyte, % monocyte, and % eosinophil). The coagulation study measures activated partial thromboplastin time (APTT) and prothrombin time (PT). Clinical chemistry studies includes analysis of the following: alkaline phosphatase (ALP), glucose (GLU), albumin (ALB), alanine aminotransferase (ALT), total bilirubin (TBIL), globulin (Glob), aspartate aminotransferase (AST), cholesterol (CHOL), potassium (K), gamma glutamyltransferase (GGT), triglycerides (TRIG), chloride (Cl), creatinine (CREAT), blood urea nitrogen (BUN), sodium (Na), inorganic phosphorus (PHOS), calcium (Ca), A/G ratio, and total protein (TPROT).

Local tissue histopathology is also evaluated, including an examination of tendon toxicity and bone toxicity.

The rhPDGF-BB is not toxic to the dogs.

Acute Systemic Toxicity. The objective of this study is to determine the systemic toxicity of rhPDGF-BB administered by intravenous injection.

The study uses Sprague-Dawley rats. The animals are housed at the same lab facility for the duration of the study. All housing and husbandry is in accordance with the Animal Welfare Act and the "Guide for the Care and Use of Laboratory Animals". Animals are fed and watered in accordance with standard protocols. Food and water are withheld for appropriate study related events such as anesthesia. Animals are acclimated to the facility for a minimum of 5 days prior to the study. This acclimation period allows the animals to become accustomed to the study room setting.

Sterile recombinant human PDGF-BB at 3.0 mg/ml and 0.3 mg/ml in 20 mM sodium acetate buffer, pH 6.0±0.5 is used in the study. On the day of dosing, a portion of the 0.3 mg/mL solution is diluted 1:10 in 20 mM sodium acetate buffer to create a 0.03 mg/ml solution which also is used in the study. The control sample is sterile 20 mM sodium acetate buffer, pH 6.0±0.5, and is prepared according to standard procedures.

Standard laboratory safety procedures are employed for handling the test and control articles. Specifically, gloves, facemask, gown (or lab coat) and eye protection are worn while preparing and administering doses.

Animals are randomized into four groups, with n=40 per group (20 males and 20 females/group). Dose group 1 receives a single intravenous injection of 20 mM sodium acetate, pH 6.0±0.5 at a volume of 1.4 ml/kg; dose group 2 receives a single intravenous injection of 3.0 mg/ml rhPDGF-BB in 20 mM sodium acetate, pH 6.0±0.5 at a volume of 1.4 ml/kg; dose group 3 receives a single intravenous injection of 0.3 mg/ml rhPDGF-BB in 20 mM sodium acetate, pH 6.0±0.5 at a volume of 1.4 ml/kg; dose group 4 receives a single intravenous injection of 0.03 mg/ml rhPDGF-BB in 20 mM sodium acetate, pH 6.0±0.5 at a volume of 1.4 ml/kg.

Animals are evaluated for death and other signs of severe toxicity. During the study duration, animals are observed for viability, clinical examinations, body weights, food consumption, ophthalmic examination, and clinical pathology. Upon necropsy on day 2 and day 14 (10 males and 10 females/group/timepoint), animals undergo a clinical pathology evaluation, including hematology, coagulation, serum chemistry, and urinalysis, as well as a full necropsy.

Example 3: Dose Response of Intra-Tendon (IT) Application of rhPDGF-BB in the Collagenase-Induced Rat Achilles Tendon Injury Model The objective of the study was to determine the dose-response of an intra-tendon application of rhPDGF-BB in a rat tendon collagenase model to validate the reparative effect of rhPDGF-BB on Achilles tendon injury and remodeling. We hypothesized that intra-tendon delivery of rhPDGF-BB will result in tendon repair by upregulating cell proliferation and restoring biomechanical strength of the tendon.

The recombinant human platelet-derived growth factor BB (rhPDGF-BB) is mitogenic and chemotactic for cells of mesenchymal origin, such as osteoblasts, tenocytes, chondrocytes and mesenchymal stem cells. Thus, when introduced into musculoskeletal sites of injury, rhPDGF-BB attracts connective tissue cells and progenitors to the treatment site, stimulating their proliferation, resulting in increased numbers of cells which subsequently deposit matrix to regenerate the injured tissue(s). In addition, as shown in Example 1 above, tenocytes exposed to PDGF-BB showed an increase in DNA synthesis and chemotaxis.

Collagenase-Induced Rat Achilles Tendon Injury Model

There is not a single well-established model for the evaluation of tendinopathy. However, the collagenase-induced rat Achilles tendon injury model has been widely used for Achilles tendon injury. This model initiates a degenerative tendon response regarded as being equivalent to tendinitis, and develops tendinitis injury quickly (within 3 days) compared to the uphill treadmill overuse model (4 months). Thus, it is a quick model to screen for the effect of rhPDGF-BB on tendon injury. Therefore, the model enjoys a relatively rapid induction period and is highly suitable and representative of clinical tendinitis as a screen for the therapeutic effect of rhPDGF-BB.

A total of one hundred sixty five (165) male Sprague Dawley rats were used in this study. They were administered a collagenase injection in their right Achilles tendon followed by a single injection treatment of rhPDGF-BB or control (buffer only) at the site of injury 7 days after the collagenase injection. Collagenase and rhPDGF-BB or control (buffer only) was injected into right Achilles tendons of rats near the osseous-tendon junction using insulin syringes with 28.5 G needles.

The animals were divided into 11 groups with n=15 in each group, as outlined in Table 1. Studies reported in the literature utilizing this model have historically used 8-9 animals per treatment group for biomechanical testing and 3-6 animals for histological analysis.

Test and Control Articles

The study control group utilized the natural reparative response of rat tendon in the collagenase-treated rat Achilles tendon without rhPDGF-BB as a control to approximate the natural healing response of an injured tendon. The study test article used rhPDGF-BB as an injectable drug to aid in the regeneration of tendon. The recombinant human platelet-derived growth factor BB (rhPDGF-BB) is mitogenic and chemotactic for cells of mesenchymal origin, such as osteoblasts, tenocytes, chondrocytes and mesenchymal stem cells. Thus, when introduced into musculoskeletal sites of injury, rhPDGF-BB attracts connective tissue cells and progenitors to the treatment site, stimulating their proliferation, resulting in increased numbers of cells which subsequently deposit matrix to regenerate the injured tissue(s). In addition, as shown in Example 1 above, tenocytes exposed to PDGF-BB showed an increase in DNA synthesis and chemotaxis.

Two batches of sterile recombinant human PDGF-BB at different concentrations were used in the study: (1) 3.4 mg/ml rhPDGF-BB in 20 mM sodium acetate buffer, pH 6.0±0.5; and (2) 0.34 mg/ml rhPDGF-BB in 20 mM sodium acetate buffer, pH 6.0±0.5. The vehicle control sample was sterile 20 mM sodium acetate buffer, pH 6.0±0.5, prepared according to standard procedures. Doses include: 1.02 µg, 10.2 µg and 102 µg rhPDGF-BB. Two concentrations of rhPDGF-BB in NaOAc buffer were prepared: 3.4 mg/ml and 0.34 mg/ml. When delivered at 30 µl intratendon, 102 µg and 10.2 µg dose levels were achieved. For the 1.02 µg dose, the 0.34 mg/mL solution was diluted 1:10 with 20 mM NaOAc buffer. Collagenase was purchased in powder form from Sigma-Aldrich (Catalog No. C-6885; St. Louis, Mo.) and reconstituted to the desired concentration (10 mg/mL) in PBS containing 50 mM $NaH_2PO_4$ and 150 mM NaCl at pH 7.4±0.5.

At study initiation, at least two unopened, unused vials of the 3.4 mg/ml rhPDGF-BB, 0.34 mg/ml rhPDGF-BB, and 20 mM sodium acetate buffer test articles were retained under the same storage conditions (4° C.) as the vials used for dosing, stability and concentration analysis. Stability and dose verification analyses were performed using UV/Vis spectrophotometry and reverse phase HPLC analyses.

Standard laboratory safety procedures were employed for handling the test and vehicle control articles. Specifically, gloves, facemask, gown (or lab coat) and eye protection were worn while preparing and administering doses.

Test System (Animals and Animal Care)

One hundred sixty five (165) male Sprague Dawley rats (Charles River Laboratories, Intl, Wilmington, Mass.) were used in this study. Prior to study selection, all animals were screened by visual examination to ensure health and normal gait. All animals were selected for the study based upon their weight (approximately 315 grams at the time of collagenase injection). Each rat was identified by a unique number written on their tails. Rats were assigned randomly to each group according to their body weights.

The rats were housed at the same lab facility for the duration of the study. All housing and husbandry was in accordance with the Animal Welfare Act and the "Guide for the Care and Use of Laboratory Animals". Food and water was withheld for appropriate study related events such as anesthesia but was otherwise provided ad libitum. Animals were acclimated to the facility for a minimum of 5 days prior to the study. This acclimation period allowed the animals to become accustomed to the study room setting.

Experimental Design

Figure 3:
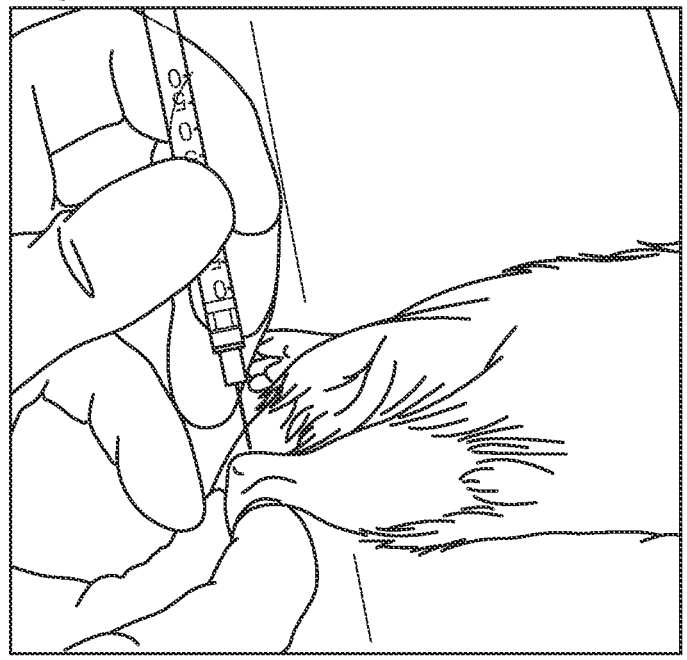
FIG. 3 shows the injection site at the tendon-calcaneous junction in the right leg. Injections were performed with an insulin syringe using a 28.5 G needle.

Animals (15 per group), housed 4 per cage, were anesthetized with isoflurane and the hock area clipped and cleaned for injection. Collagenase (50 µl of 10 mg/ml dissolved in PBS containing 50 mM $NaH_2PO_4$ and 150 mM NaCl at pH 7.4) was injected into the right Achilles tendons of all rats near the osseous-tendon junction using insulin syringes with 28.5 G needles (FIG. 3). Seven days post collagenase injection, treatments with vehicle or 1.02 µg, 10.2 µg or 102 µg of rhPDGF-BB in 30 µl total volume were administered using insulin syringes with 28.5 G needles. Animals were terminated at 7 (baseline) 14, and 28 days for histopathologic evaluation of tendon damage and biomechanics. In each group of 15 animals, 6 animals were used for histopathology and the hind legs of 9 animals (both treated and non-treated rear limbs) was removed, dissected, and frozen for subsequent biomechanical evaluation. Description of the biomechanical evaluation is provided below.

TABLE 1

Treatment Groups

| Group Number | Treatment Group | Animals (n) | rhPDGF-BB | Endpoint |
|---|---|---|---|---|
| 1 | Collagenase + No treatment Terminate Day 7 (Baseline) | 15 | 0 | Biomechanics (N = 9) Histology (N = 6) |
| 2 | Collagenase + No treatment Terminate Day 14 | 15 | 0 | Biomechanics (N = 9) Histology (N = 6) |
| 3 | Collagenase + No treatment Terminate Day 28 | 15 | 0 | Biomechanics (N = 9) Histology (N = 6) |
| 4 | Collagenase + Sodium Acetate Terminate Day 14 | 15 | 0 | Biomechanics (N = 9) Histology (N = 6) |
| 5 | Collagenase + Sodium Acetate Terminate Day 28 | 15 | 0 | Biomechanics (N = 9) Histology (N = 6) |
| 6 | Collagenase + rhPDGF-BB Terminate Day 14 | 15 | 102 µg | Biomechanics (N = 9) Histology (N = 6) |
| 7 | Collagenase + rhPDGF-BB Terminate Day 28 | 15 | 102 µg | Biomechanics (N = 9) Histology (N = 6) |
| 8 | Collagenase + rhPDGF-BB Terminate Day 14 | 15 | 10.2 µg | Biomechanics (N = 9) Histology (N = 6) |

TABLE 1-continued

Treatment Groups

| Group Number | Treatment Group | Animals (n) | rhPDGF-BB | Endpoint |
|---|---|---|---|---|
| 9 | Collagenase + rhPDGF-BB Terminate Day 28 | 15 | 10.2 µg | Biomechanics (N = 9) Histology (N = 6) |
| 10 | Collagenase + rhPDGF-BB Terminate Day 14 | 15 | 1.02 µg | Biomechanics (N = 9) Histology (N = 6) |
| 11 | Collagenase + rhPDGF-BB Terminate Day 28 | 15 | 1.02 µg | Biomechanics (N = 9) Histology (N = 6) |

In-Life Observations and Measurements

Animals were observed at least daily until sacrifice. Treatment of the animals was in accordance with the regulations outlined in the USDA Animal Welfare Act (9 CFR, Parts 1, 2, and 3) and the conditions specified in The Guide for Care and Use of Laboratory Animals (ILAR publication, 1996, National Academy Press), and HSS veterinary procedures.

Body weights were recorded prior to the collagenase injection and before sacrifice. Food consumption was qualitative.

All animals were sacrificed at the appropriate study end points. No unscheduled animal deaths were observed. Upon the completion of the in-life treatment groups, animals were euthanized and tissues harvested in accordance with the USDA Animal Welfare Act, The Guide for Care and Use of Laboratory Animals (ILAR publication, 1996, National Academy Press), and HSS veterinary procedures. Animals were euthanized by $CO_2$ overdose. Death was confirmed by lack of reflexes (blinking, withdrawal, etc.).

Gross Tendon Size

Immediately prior to necropsy, ankles were scored for thickness according to the following systems: 0=no growth; 1=mild growth; 2=moderate growth; 3=severe growth.

Histology

At necropsy, the skin was carefully removed from the hock area with the entire foot submerged in 10% neutral buffered formalin (NBF) and fixed in flexion. After a minimum of 12 hours in 10% NBF and 4-5 days in 10% formic acid to decalcify, the ankle, with special emphasis on the tendon-osseous junction was trimmed both medially and laterally to achieve an approximately ¼ inch thick tissue block (central portion of ankle with tendon attachment) and placed in labeled tissue cassettes. The trimmed ankle tissue block was processed for paraffin embedding in the saggital orientation. Using a rotary microtome, representative 4-6 micron thick sections were taken at 200 micron step sections until suitable visualization of the osseous-tendon junction was achieved and those sections were then stained with hematoxylin and eosin (H&E), Masson's Trichrome, and for immunohistochemistical (IHC) detection of proliferating cell nuclear antigen (PCNA).

All animals were bled for serum terminally by descending aorta vacutainer while under Isoflurane anesthesia (10 mls blood were collected). The blood was centrifuged at 1,800 g at room temperature for 10 minutes to obtain serum. Up to 1 ml of serum was provided in 2 ml Eppendorf® tubes. The serum was stored at −70° C. prior to analysis.

Histopathological assessment was performed as described below. Measurements for different parameters were made by assessing three equidistant field columns from each histologic specimen (slide) using light microscopy.

The measured parameters for histopathology included:

(1) Inflammation. Inflammatory cell types (neutrophils, lymphocytes, and macrophages) were determined by H&E staining. Inflammation was scored as follows: (a) 0=no inflammation; (b) 1=minimal inflammation (100% Mononuclear; no neutrophils); (c) 2=moderate inflammation (neutrophils ≤19%; remainder of cells mononuclear); and (d) 3=marked inflammation (neutrophils ≥20%; remainder of cells mononuclear).

(2) Collagen organization. Organization of collagen fibrils was assessed by H&E and Trichrome staining. Collagen organization was scored as follows: (a) 0=collagen fibrils are completely disorganized; (b) 1=some alignment of the collagen fibrils but the majority of the bundles are highly disorganized; (c) 2=the collagen fibrils are highly aligned however the bundles are still somewhat disorganized; and (d) 3=the collagen fibrils present in the tissue are completely aligned and there is no disorganization of the collagen bundles.

(3) Collagen fiber density. Collagen fiber density in the repair tissue was assessed by H&E and Trichrome staining. Collagen fiber density was scored as follows: (a) 0=low density collagen bundles; (b) 1=medium density collagen bundles; and (c) 2=highly dense collagen bundles.

(4) Tendon vascularization at site of repair. Vascularization in the repair tissue was determined by H&E and Trichrome staining. Vascularization was scored as follows: (a) 0=none (no vascularization present); (b) 1=moderate; and (c) 2=abundant.

(5) Cell proliferation. Cell proliferation was evaluated using immunohistochemistry (IHC) for PCNA (proliferating cell nuclear antigen). An ocular micrometer was used to delineate an area that was 39.4×197 µm (7762 µm2), or 10×50 units on the micrometer. Three fields having this measurement were counted for each specimen. Proliferating cells were counted from these 3 equidistant fields.

(6) Tendon Width Measurements. Measurements of the tendon at two different locations were taken under the microscope and using an ocular micrometer. Measurements were taken of the calcaneous attachment point (non-tangential area thought to best represent the thickness of the attachment site) and of the tendon itself (thickest non-tangential area of the tendon body remote from the attachment site with associated proliferative response).

Semi-quantitative histopathology data was analyzed using Mann-Whitney U test or Kruskal-Wallis test (non-parametric). Applicable data was analyzed across all groups, using a one-way analysis of variance (1-way ANOVA), along with the appropriate multiple comparison post-test.

Biomechanical Testing 99 animals were utilized for this portion of the study. The injury-induced tendon was evaluated in addition to contralateral non-collagenase treated tendons. A total of 123 biomechanical specimens were evaluated. Treatment allocations are outlined in Table 1 above.

Figure 4:
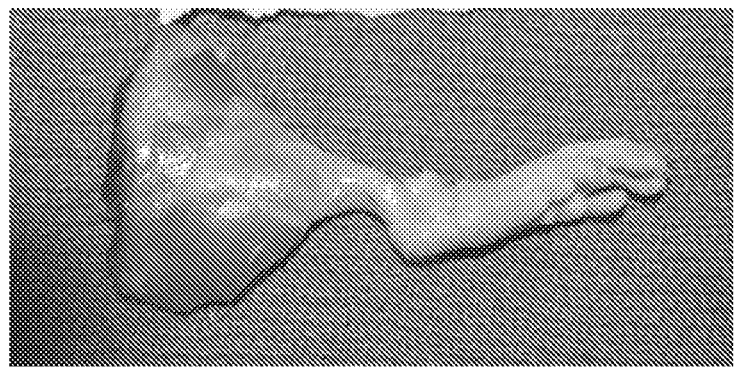
FIG. 4 shows a representative image of a rat metatarsus-Achilles-gastrocnemius complex following processing of test animals for biomechanical testing.
Figure 5:
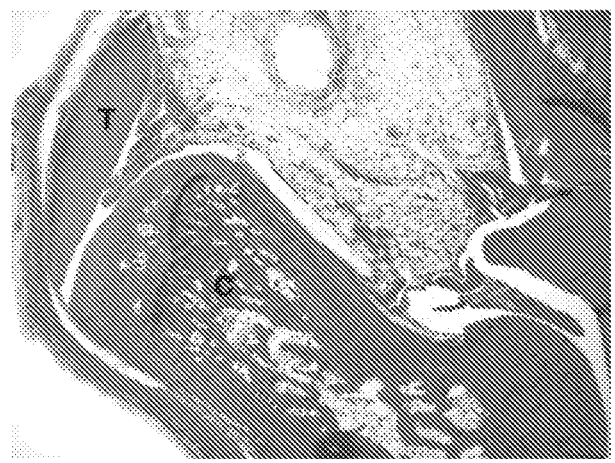
FIG. 5 shows a representative image of a sagittal section from the lateral edge of the calcaneous (C)-Achilles tendon (T) attachment site.

The leg was detached at the femur and de-sleeved to the mid-foot. Using a scalpel, the Achilles-gastrocnemius complex was detached from the tibia. Briefly, starting at the calcaneal insertion the scalpel was run along the tibia to separate the complex and a majority of muscle was left attached to the tendon to allow for gripping for biomechanical testing. After separation of the tendon, tibia was removed at the junction with the metatarsus, leaving the foot attached for gripping at distal end for biomechanical testing (FIG. 4). The entire metatarsus-Achilles-gastrocnemius specimen was wrapped in saline-soaked gauze and frozen at −20° C. for storage before performing biomechanical analysis.

Samples were thawed in PBS containing proteinase inhibitors at 4° C. up to 4 hours prior to mechanical testing. Tendon samples were patted dry, and excess muscle was removed to facilitate mounting of samples in grips. Bone was trimmed with clippers to facilitate mounting.

All mechanical testing was performed on an Instron testing frame (Model 5566) where samples were tested while submersed in a bath containing PBS. Precise displacement control was applied to each specimen, and the resulting load was measured using a 100N load cell with load accuracy of ±0.5%. All data acquisition and device control was performed with a personal computer, where data will be acquired at 10 Hz.

Specimens were mounted in hydraulic grips between two roughened surface plates and sand paper, in order to prevent slippage of the sample during pull testing. A pre-load of 0.1N was applied to the specimens, and the length of the specimen was recorded followed by precycling for 10 cycles between loads of 0.1 and 1N. A uniaxial tensile displacement was applied to the constructs at a strain rate of 0.1% per second, and the resultant load was recorded. The samples will be tested to failure in tension, until fracture is reached and the measured load is observed to be <0.05N. Prior to testing, the cross sectional area of the specimen was measured. All specimens were tested blinded with no indication of identifiable group classification.

After testing, the collected data was analyzed to determine: (1) linear stiffness and (2) elastic modulus from the linear portion of the load-displacement or stress-strain curve, respectively. The maximum load and ultimate tensile strength were also determined from the loading data. The elastic toughness, defined as the area under the force displacement curve until peak load, will be calculated numerically using the Reimann sum method.

Two-way ANOVA with interaction and a Fisher's LSD post-hoc test (p<0.05) was used for analysis of the biomechanical data. Applicable data was analyzed across all groups, using a one-way analysis of variance (1-way ANOVA), along with the appropriate multiple comparison post-test.

Stress is the load on the specimen normalized to the cross sectional area of the sample. Strain represents the change in length of the specimen normalized to the original length of the sample. Consequently, the stress vs. strain curve is a normalized version of the load vs. displacement curve (eliminates the effect of variation in the specimen dimensions). For example, a longer tendon will have greater total displacement. On the other hand, a wider tendon can withhold more load than a narrower one. These slight variations in the specimen to specimen dimensions significantly affect the magnitude of load and displacement they can bear. When these variables are normalized by their dimensions to stress and strain, the analysis is no longer dependent on the size of the specimen. All properties extracted directly from the load vs. displacement curves are referred to as structural properties. All properties extracted from the normalized stress vs. strain curves are referred to as material properties.

Linear Stiffness is a structural property that is determined from a least-square fit of the linear portion of the load vs. displacement curve. It represents the tensile stiffness of the specimen.

Elastic Modulus is a material property that is determined from a least-square fit of the linear portion of the stress vs. strain curve. It represents the tensile stiffness of the tendon material.

Maximum Load is the largest load that the specimen can withstand during pulling.

Ultimate Tensile stress is the maximum load normalized by the specimen's cross sectional area.

Toughness is resistance of a material to fracture or break. It is usually measured in units of energy, and calculated as the area under the load-displacement curve until failure.

Results

Effect of rhPDGF-BB on Gross Ankle Thickness

Figure 6A:
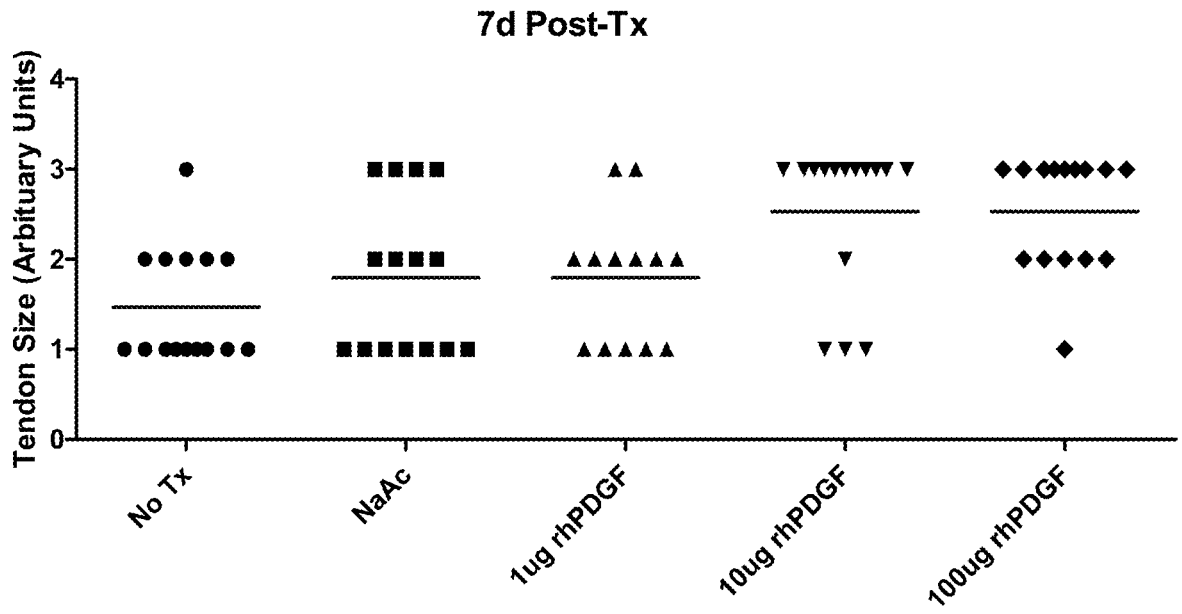
FIG. 6A shows the results of a dose response study on gross observational tendon growth for intra-tendon application of recombinant human platelet-derived growth factor, isoform BB ("rhPDGF-BB"), in the collagenase-induced rat Achilles tendon injury model seven days after treatment. A single injection of a medium (10.2 µg) or high (102 µg) dose of rhPDGF-BB produced a significant increase in tendon size seven days following rhPDGF-BB treatment.
Figure 6B:
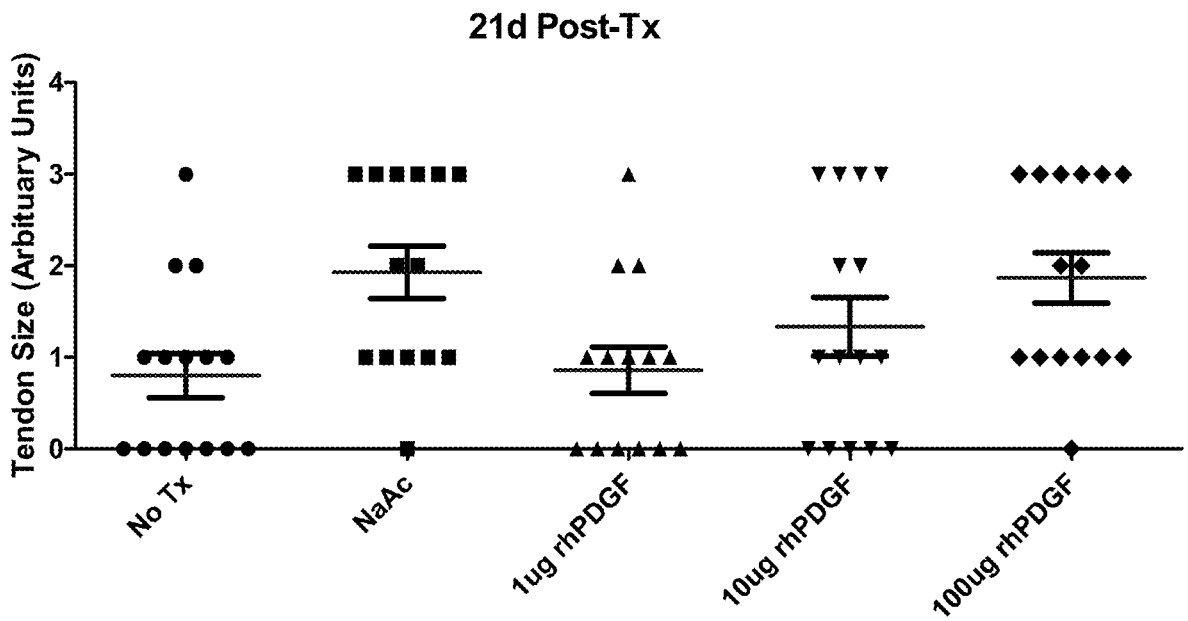
FIG. 6B shows the results of the same study twenty-one days following rhPDGF-BB treatment. The effect of a single injection of a high (102 µg) dose of rhPDGF-BB on tendon size was comparable to the effect of injection with sodium acetate buffer alone twenty-one days after treatment.
Figure 7:
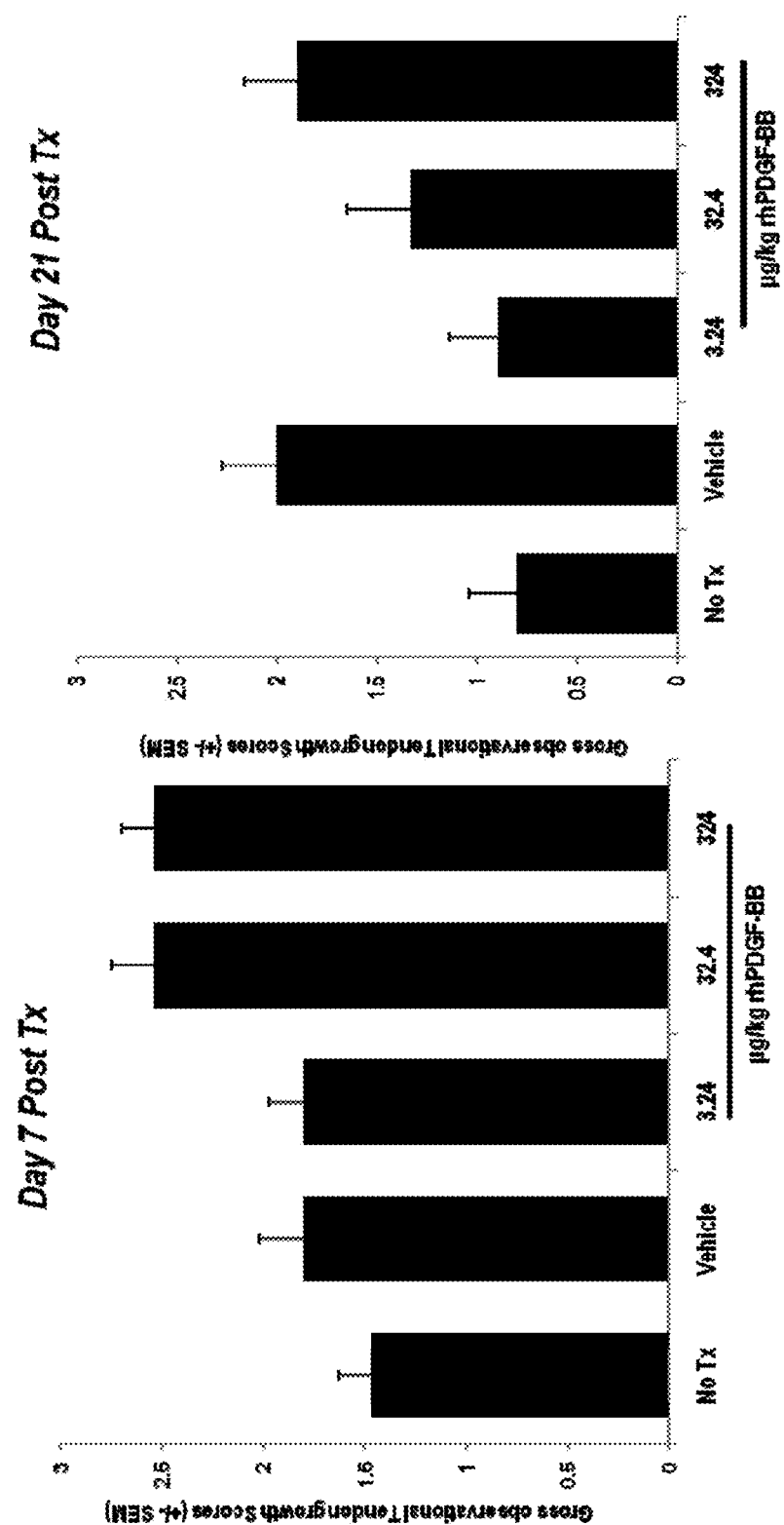
FIG. 7 is a different presentation of the same data as FIGS. 6A and 6B, showing the gross tendon size at 7- and 21-days post-rhPDGF-BB treatment (0=no growth to 3=severe growth).

A dose-dependent increase in gross ankle thickness was observed seven days post single intra-tendon injection of rhPDGF-BB (FIG. 6A and FIG. 7, Day 7 Post Tx), with the medium (10.2 µg) and high (102 µg) dose producing a significant increase in tendon size at seven days post-injection. At Day 21 Post Tx, all groups except the vehicle control group (the sodium acetate buffer) exhibited a decrease in gross ankle thickness, suggesting tissue remodeling at day 21 post-treatment (FIG. 6B and FIG. 7, Day 21 Post Tx). The data in FIGS. 6A, 6B, and 7 were based on an analog scale at 7- and 21-days post-rhPDGF-BB treatment (0=no growth to 3=severe growth). Data reported are means of the ankle thickness (±SEM) of n=6 animals per group.

Effect of rhPDGF-BB on Body Weights

At the time of treatment, the average body weight of the animals was 314.48 grams. At 7- and 21-days post-treatment the average body weights were 396.4 and 467.0 grams, respectively. There were no treatment related changes in body weight at either time point.

Effect of rhPDGF-BB on Bone

Neither abnormal bone growth nor resorption was identified.

Effect of rhPDGF-BB on Tendon Width at the Calcaneous Attachment

Figure 8:
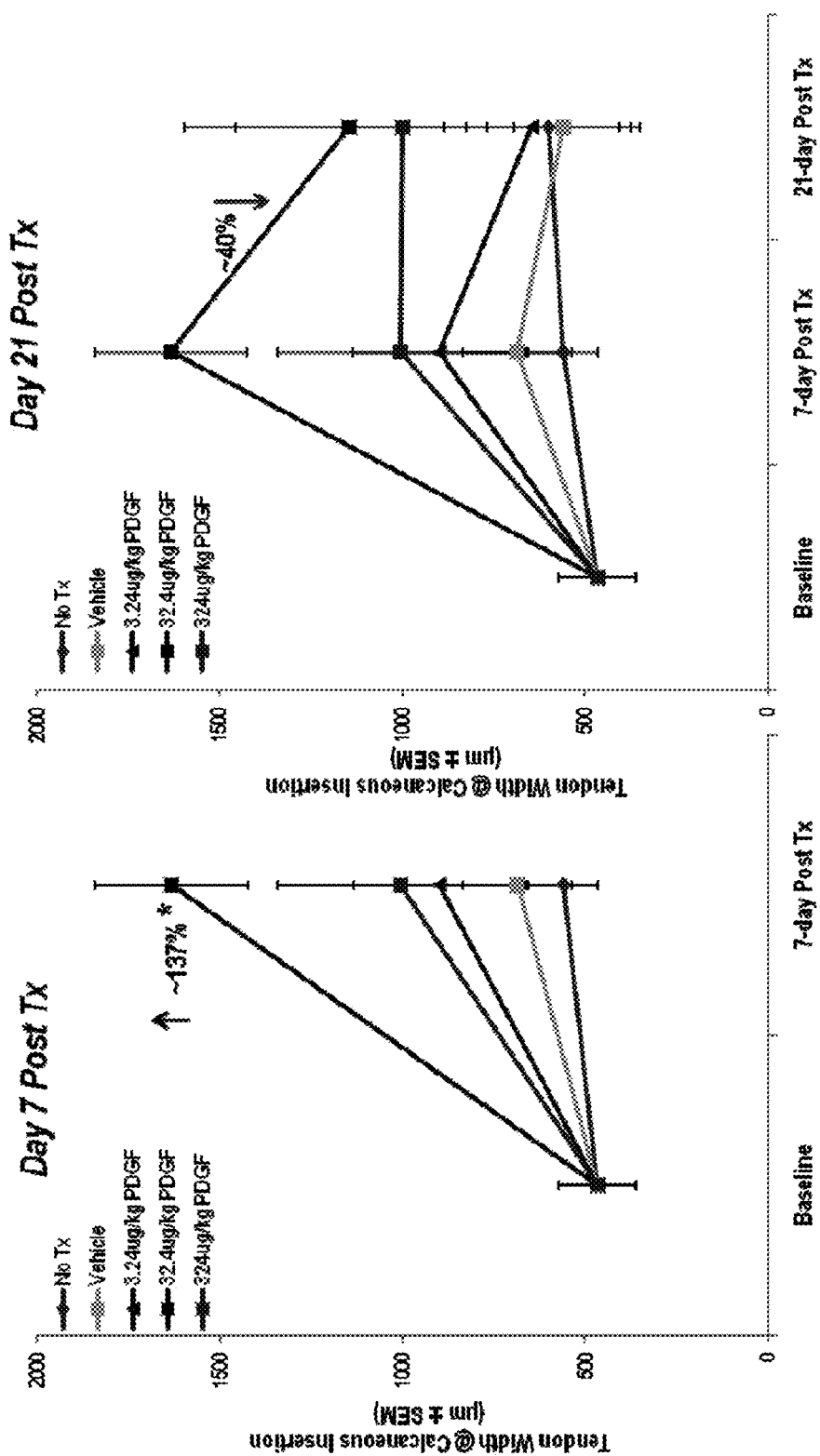
FIG. 8 shows tendon width (µm±SEM) at the calcaneous insertion at 7- and 21-days post-rhPDGF-BB treatment.

FIG. 8 shows the measured tendon width (µm±SEM) at the Calcaneous insertion at day 7 and 21 post-treatment. Data reported are means of the tendon width (±SEM) at the calcaneous insertion of n=6 animals per group; * p=0.01 vs. vehicle control group. The tendon width was measured by microscopy using an ocular micrometer.

Seven days post-treatment (Day 7 Post Tx) a significant increase (~137% increase) in the tendon width at the calcaneous insertion with the 32.4 µg/kg rhPDGF-BB dose-group as compared to vehicle was observed (FIG. 8, Day 7 Post Tx). Animals treated with 3.24 and 324 µg/kg rhPDGF-BB did not demonstrate a significant increase in tendon width, but trended higher as compared to vehicle control. No significant difference between the tendon widths of animals treated with or without rhPDGF-BB was determined at day 21 post-treatment (FIG. 8, Day 21 Post Tx). By day 21 post-treatment (FIG. 8, Day 21 Post Tx), the 32.4 µg/kg rhPDGF-BB dose group exhibited a 40% decrease in tendon width as compared to day 7 post-treatment, suggesting the tendon remodeled (FIG. 8).

Effect of rhPDGF-BB on Tendon Width at the Tendon Mid-Body

Figure 9:
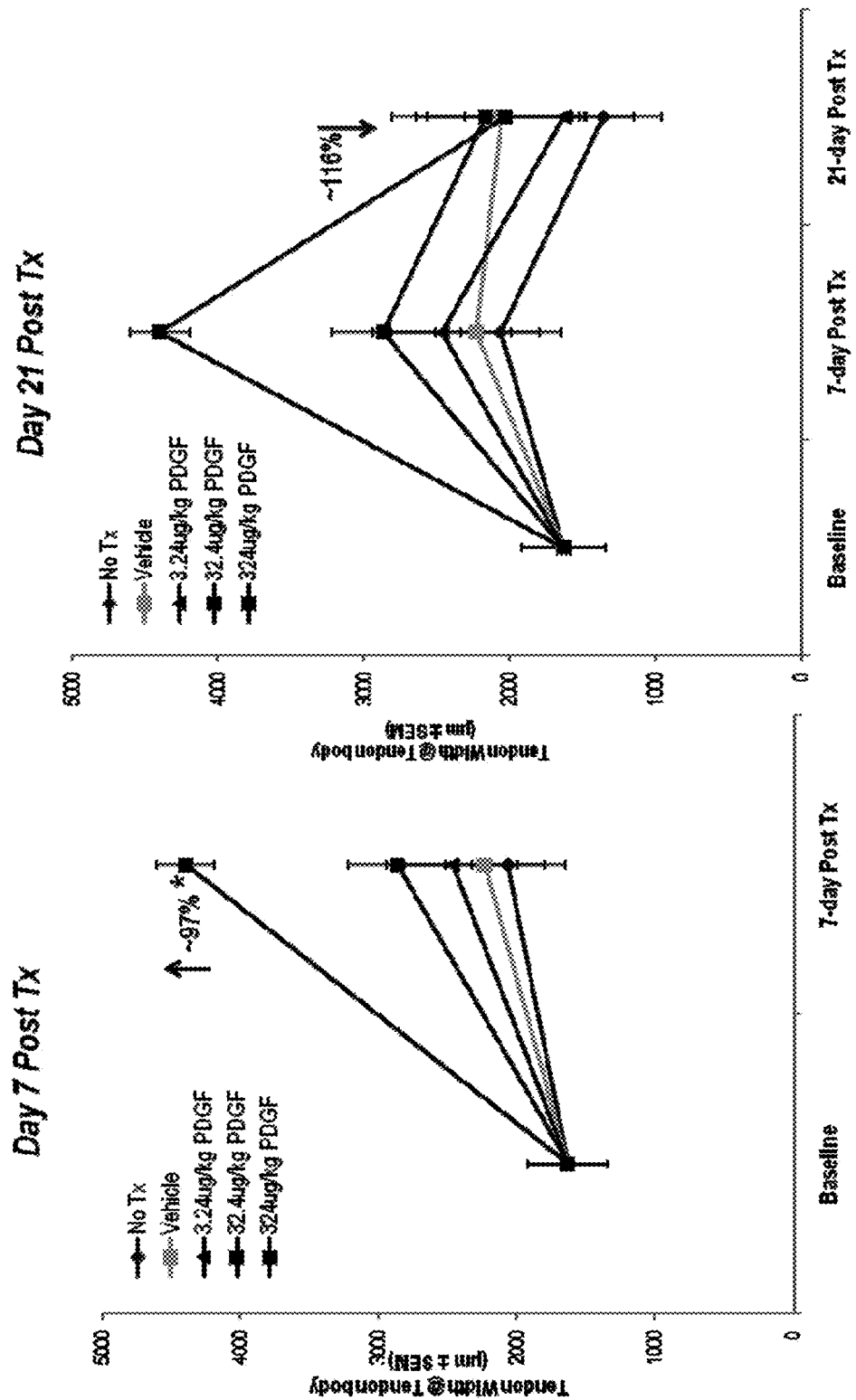
FIG. 9 shows tendon width (µm±SEM) at the tendon body at 7- and 21-days post-rhPDGF-BB treatment.

FIG. 9 represents the measured tendon width (µm±SEM) at the tendon mid-body at day 7 and 21 post-treatment. Data reported are means of tendon width (±SEM) at the tendon body of n=6 animals per group; * p<0.05 vs. vehicle group. The tendon width was measured by microscopy using an ocular micrometer.

An ~97% increase in tendon width was observed with the 32.4 µg/kg rhPDGF-BB dose vs. vehicle control group at day 7 post-treatment (FIG. 9, Day 7 Post Tx). A non-significant dose-dependent increase was observed in the 3.24 and 324 µg/kg dose groups vs. vehicle and no treatment (Tx) groups. By day 21, no significant differences in tendon widths were observed across groups (FIG. 9, Day 21 Post Tx). However, at day 21, the 32.4 µg/kg rhPDGF-BB dose group exhibited a 116% decrease in tendon width as compared to day 7 post-treatment, suggesting the tendon remodeled.

Effect of rhPDGF-BB on Cell Proliferation

Figure 10:
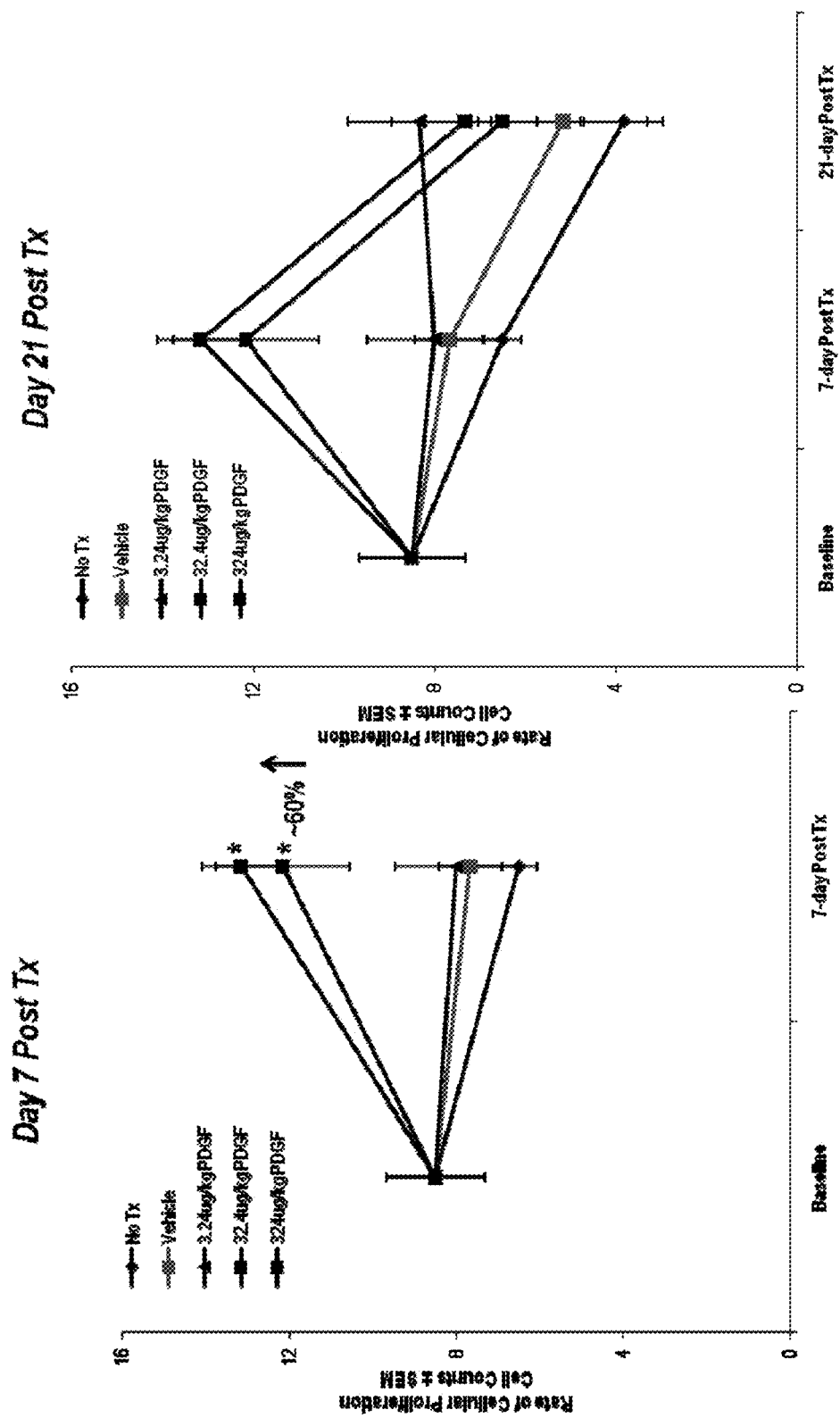
FIG. 10 shows the effect of rhPDGF-BB on rate of cellular proliferation (cell counts±SEM) at 7- and 21-days post-rhPDGF-BB treatment.

Quantitation of cell proliferation was done by cell counts of positive PCNA immunostained cells (FIG. 10). Data reported are means of cell counts (±SEM) of n=6 animals per group; * p<0.05 vs. vehicle. Three fields having equal measurement were counted for each specimen.

A dose-dependent increase in cellular density was observed in the rhPDGF-BB groups. An rhPDGF-BB dose-dependent increase in cell proliferation was observed at day 7 post-treatment (FIG. 10, Day 7 Post Tx); a significant increase in cellular proliferation was observed in the 32.4 and 324 µg/kg dose groups vs. vehicle control (FIG. 10, Day 7 Post Tx), representing a ~60% and ~72% increase respectively. However, by day 21, no significant difference in cell proliferation was observed (FIG. 10, Day 21 Post Tx). A return to vehicle control proliferation level was observed for the 32.4 and 324 µg/kg rhPDGF-BB dose groups, indicating that the proliferative response of rhPDGF-BB was reversible (FIG. 10, Day 21 Post Tx).

Effect of rhPDGF-BB on Inflammation

Mild to moderate inflammation consisting of macrophages and mononuclear cells was observed across all groups at all time points (Table 2).

TABLE 2

Effect of rhPDGF-BB on inflammation using an analog scale (0 = no inflammation to 3 = severe inflammation) at 7- and 21- days following treatment.

| | | | Groups | | | |
|---|---|---|---|---|---|---|
| Animal Number | Baseline | No Tx | Vehicle | 3.24 µg/kg | 32.4 µg/kg | 324 µg/kg |
| 7 Days Post-Tx | | | | | | |
| 1 | 2 | 1 | 1 | 1 | 2 | 2 |
| 2 | 2 | 1 | 2 | 2 | 2 | 1 |
| 3 | 2 | 1 | 1 | 2 | 2 | 2 |
| 4 | 2 | 1 | 1 | 2 | 2 | 1 |
| 5 | 2 | 1 | 1 | 2 | 2 | 2 |
| 6 | 2 | 2 | 2 | 2 | 2 | 2 |
| Mean | 2 | 1.167 | 1.333 | 1.833 | 2 | 1.667 |
| SD | 0 | 0.408 | 0.516 | 0.408 | 0 | 0.516 |
| 21 Days Post-Tx | | | | | | |
| 1 | 2 | 1 | 1 | 1 | 1 | 1 |
| 2 | 2 | 1 | 2 | 1 | 1 | 1 |
| 3 | 2 | 1 | 2 | 1 | 1 | 2 |
| 4 | 2 | 1 | 1 | 1 | 1 | 2 |
| 5 | 2 | 2 | 1 | 1 | 1 | 2 |
| 6 | 2 | 1 | 1 | 1 | 1 | 2 |
| Mean | 2 | 1.167 | 1.333 | 1 | 1 | 1.667 |
| SD | 0 | 0.408 | 0.516 | 0 | 0 | 0.516 |

Effect of rhPDGF-BB on Vascularization

No significant change in vascularization was observed across all groups and time points (Table 3)

TABLE 3

Effect of rhPDGF-BB on vascularization using an analog scale (0 = none to 2 = severe) at 7- and 21- days following treatment.

| | | | Groups | | | |
|---|---|---|---|---|---|---|
| Animal Number | Baseline | No Tx | Vehicle | 3.24 µg/kg | 32.4 µg/kg | 324 µg/kg |
| 7 Days Post-Tx | | | | | | |
| 1 | 1 | 2 | 2 | 1 | 2 | 2 |
| 2 | 0 | 2 | 2 | 2 | 2 | 1 |
| 3 | 2 | 1 | 1 | 2 | 2 | 2 |
| 4 | 2 | 1 | 1 | 2 | 2 | 2 |
| 5 | 1 | 2 | 1 | 2 | 2 | 2 |
| 6 | 2 | 2 | 2 | 2 | 2 | 2 |
| Mean | 1.333 | 1.667 | 1.5 | 1.833 | 2 | 1.833 |
| SD | 0.818 | 0.516 | 0.548 | 0.408 | 0 | 0.408 |
| 21 Days Post-Tx | | | | | | |
| 1 | 1 | 1 | 1 | 0 | 1 | 2 |
| 2 | 0 | 1 | 2 | 1 | 1 | 1 |
| 3 | 2 | 1 | 2 | 1 | 2 | 2 |
| 4 | 2 | 1 | 1 | 2 | 1 | 2 |
| 5 | 1 | 2 | 1 | 2 | 1 | 1 |
| 6 | 2 | 1 | 1 | 1 | 2 | 1 |
| Mean | 1.333 | 1.167 | 1.333 | 1.167 | 1.333 | 1.5 |
| SD | 0.816 | 0.408 | 0.516 | 0.753 | 0.516 | 0.548 |

Effect of rhPDGF-BB on Collagen Density

No significant change in collagen density was observed across all groups and time points (Table 4).

TABLE 4

Effect of rhPDGF-BB on collagen density using an analog scale (0 = none to 2 = severe) at 7- and 21- days following treatment.

| | | | Groups | | | |
|---|---|---|---|---|---|---|
| Animal Number | Baseline | No Tx | Vehicle | 3.24 µg/kg | 32.4 µg/kg | 324 µg/kg |
| 7 Days Post-Tx | | | | | | |
| 1 | 1 | 1 | 2 | 2 | 1 | 1 |
| 2 | 1 | 1 | 1 | 1 | 1 | 2 |
| 3 | 1 | 1 | 2 | 1 | 1 | 1 |
| 4 | 1 | 1 | 2 | 1 | 1 | 2 |
| 5 | 2 | 1 | 2 | 1 | 1 | 2 |
| 6 | 1 | 1 | 1 | 1 | 1 | 2 |
| Mean | 1.167 | 1 | 1.667 | 1.167 | 1 | 1.667 |
| SD | 0.408 | 0 | 0.516 | 0.408 | 0 | 0.516 |
| 21 Days Post-Tx | | | | | | |
| 1 | 1 | 2 | 2 | 2 | 2 | 2 |
| 2 | 1 | 2 | 1 | 2 | 2 | 2 |
| 3 | 1 | 2 | 1 | 2 | 2 | 1 |
| 4 | 1 | 2 | 2 | 2 | 2 | 1 |
| 5 | 2 | 2 | 2 | 2 | 2 | 2 |
| 6 | 1 | 2 | 2 | 2 | 2 | 2 |
| Mean | 1.167 | 2 | 1.667 | 2 | 2 | 1.667 |
| SD | 0.408 | 0 | 0.516 | 0 | 0 | 0.516 |

Effect of rhPDGF-BB on Collagen Organization

No significant change in collagen organization was observed across all groups and time points (Table 5).

TABLE 5

Effect of rhPDGF-BB on collagen organization using an analog scale (0 = none to 3 = highly organized) at 7- and 21- days following treatment.

| Animal Number | Baseline | No Tx | Vehicle | 3.24 μg/kg | 32.4 μg/kg | 324 μg/kg |
|---|---|---|---|---|---|---|
| *7 Days Post-Tx* | | | | | | |
| 1 | 1 | 2 | 3 | 3 | 2 | 2 |
| 2 | 1 | 2 | 2 | 2 | 2 | 3 |
| 3 | 1 | 2 | 3 | 2 | 2 | 2 |
| 4 | 2 | 2 | 3 | 2 | 2 | 3 |
| 5 | 3 | 2 | 3 | 2 | 2 | 2 |
| 6 | 1 | 2 | 2 | 2 | 2 | 3 |
| Mean | 1.5 | 2 | 2.667 | 2.167 | 2 | 2.5 |
| SD | 0.837 | 0 | 0.516 | 0.408 | 0 | 0.548 |
| *21 Days Post-Tx* | | | | | | |
| 1 | 1 | 3 | 3 | 3 | 3 | 3 |
| 2 | 1 | 3 | 2 | 3 | 3 | 3 |
| 3 | 1 | 3 | 2 | 3 | 2 | 2 |
| 4 | 2 | 3 | 3 | 2 | 3 | 2 |
| 5 | 3 | 2 | 3 | 2 | 3 | 3 |
| 6 | 1 | 3 | 3 | 3 | 2 | 3 |
| Mean | 1.5 | 2.833 | 2.667 | 2.667 | 2.667 | 2.337 |
| SD | 0.837 | 0.408 | 0.516 | 0.516 | 0.516 | 0.516 |

Biomechanics: Effect of rhPDGF-BB on Maximum Load to Rupture

Figure 11:
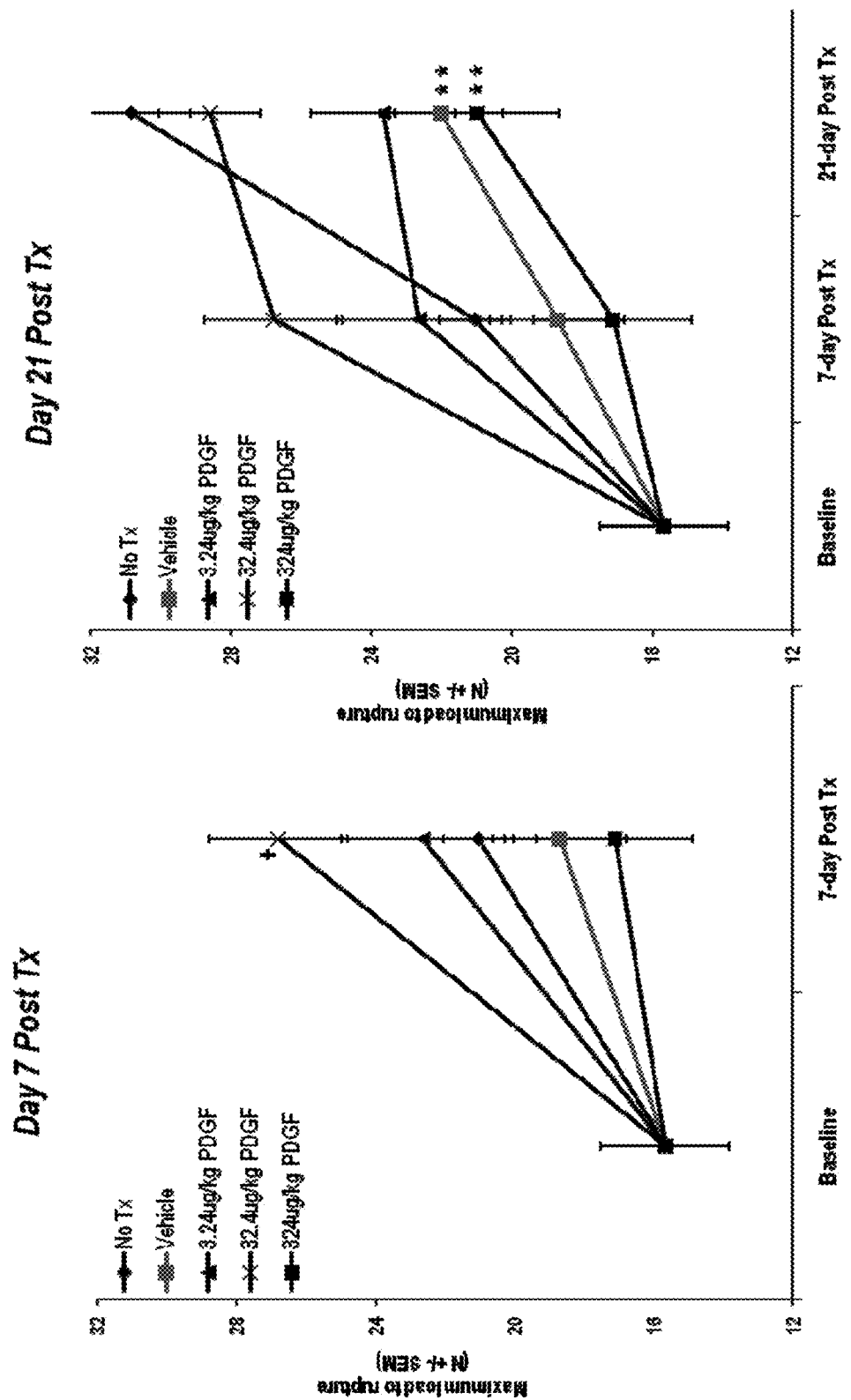
FIG. 11 shows the mechanical properties of Achilles Tendons: maximum load to rupture (N±SEM) at 7- and 21-days post-rhPDGF-BB treatment.

In this model, the non treated group spontaneously repaired as a function of time based on the maximum load to rupture values (FIG. 11). The mean maximum load to rupture values at day 7 post-treatment were significantly increased (.about.43% and 27%, respectively) in the 32.4 μg/kg dose-group vs. vehicle control and the no-treatment groups (FIG. 11, Day 7 Post Tx). By day 21 post-treatment, the maximum load to rupture was still significantly increased compared to the vehicle control (FIG. 11, Day 21 Post Tx). At day 21 post-treatment, the mean maximum load for the 32.4 μg/kg dose-group and no treatment groups was similar, indicating rhPDGF-BB treatment increased the rate of repair over no treatment. However, the vehicle and 324 μg/kg rhPDGF-BB groups had significantly lower maximum load to rupture values than the 32.4 μg g/kg dose-group and no treatment group at day 21 post-dose. Data reported are means of Maximum load to rupture (±SEM) of n=9 animals per group; +$p<0.05$ vs "vehicle" group, **$p<0.05$ vs "no treatment" group.

Table 6 represents the mechanical strength of the unharmed contralateral tendons and rhPDGF-BB treated and non-treated tendons.

TABLE 6

Maximum Load to Rupture values (N ± SEM) for Achilles Tendons at 7-, 14- and 28-days Post-collagenase injection.

| | Maximum Load to Rupture (N ± SEM) | | | |
|---|---|---|---|---|
| | Day 7 Baseline | Day 14 (Day 7 Post -Tx) | Day 28 (Day 21 Post-Tx) | Delta Δ (Compared to Vehicle) |
| Unharmed (Contralateral Legs without Collagenase Injection) | 17.36 (2.18) | 19.03 (0.67) | 27.98 (1.43) | 0.31 (Day 7 Post-Tx) 5.96 (Day 21 Post-Tx) |
| No Treatment (With Collagenase Injection without Vehicle or rhPDGF-BB) | 15.68 (1.84) | 21.06 (1.02) | 30.86 (1.71) | 2.34 (Day 7 Post-Tx) 12.14 (Day 21 Post-Tx) |
| Vehicle (With Collagenase Injection and treated with 20 mM Sodium acetate) | 15.68 (1.84) | 18.72 (1.92) | 22.02 (1.75) | — — |
| 3.24 gg/kg rhPDGF-BB (With Collagenase injection and treated with 3.24 gg/kg rhPDGF-BB) | 15.68 (1.84) | 22.65 (1.89) | 23.67 (1.89) | |
| 32.4 gg/kg rhPDGF-BB (With Collagenase injection and treated with 32.4 gg/kg rhPDGF-BB) | 15.68 (1.84) | 26.8 (1.98) | 28.61 (1.45) | 8.08 (Day 7 Post-Tx) 6.59 (Day 21 Post-Tx) |
| 324 gg/kg rhPDGF-BB (With Collagenase injection and treated with 324 gg/kg rhPDGF-BB) | 15.68 (1.84) | 17.13 (1.89) | 20.98 (1.89) | |

Data reported are means of Maximum load to rupture (±SEM) of n = 9 animals per group.

The mean maximum load to rupture value in the 32.4 µg/kg rhPDGF-BB group (26.8 N) at Day 14-post collagenase injection was increased by 41% over the unharmed tendons (19.03 N) at Day 14-post collagenase injection. This suggests that biomechanical properties in the 32.4 µg/kg rhPDGF-BB group matured faster than the normal, developing tendon. Further, the mean maximum load to rupture of the 32.4 µg/kg rhPDGF-BB group (26.8 N) at Day 14-post collagenase injection approached that of the unharmed tendons (27.98 N) at Day 28-post collagenase injection. The maximum load to rupture values in the unharmed and no treatment (collagenase injected) groups at days 7, 14 and 28 were similar. At day 14 (Day 7 Post Tx), the 32.4 µg/kg rhPDGF-BB group had higher maximum load to rupture values than the vehicle, unharmed and no treatment groups, with increases of 43%, 41%, and 27%, respectively. However, at day 28 (Day 21 Post Tx) the maximum load to rupture in the unharmed, no treatment and 32.4 µg/kg rhPDGF-BB groups was similar (Table 6).

Conclusions

In-Life Parameters

The ankle thickness results demonstrated that 7-days following rhPDGF-BB treatment there is a dose-dependent increase in tendon size but by 21-days that growth has stunted and the tissue remodels to a decreased size.

There was no significant difference in the body weights across groups and time points.

Microscopic Assessment rhPDGF-BB increased cellular proliferation, specifically fibroblastic in nature. Increases in cellular proliferation and microscopic tendon widths were reversible, indicating a possible adaptation phase to remodel the tissue.

No local adverse effects from rhPDGF-BB were observed following a single time intra-tendon delivery over a 3-week time period under the conditions of this study. There was no abnormal bone or tendon growth, and no bone resorption was identified. Inflammation was mononuclear in nature. The morphology of the cells was fibroblastic in nature.

Biomechanics

The biomechanical load to rupture data indicated that rhPDGF-BB initiated a faster repair response in mechanical strength of the tendon when compared to the non-rhPDGF-BB-treated cohorts. Although there was a return to baseline for cell proliferation and tendon width by day 21 post-treatment, this did not result in a biomechanical loss of tendon strength.

SUMMARY

The biological and biomechanical outcomes in this study validated the local safety of rhPDGF-BB injected into the tendon. Following a onetime rhPDGF-BB injection, there was an initial stage of tendon growth that abated over the 21-day time period. This study measured tendon width under a microscope using an ocular micrometer and cell proliferation using PCNA immunostaining. The results from those measurements indicated that animals treated with 32.4 µg/kg rhPDGF-BB had an increase in microscopic tendon widths and cellular proliferation at 7-days post-treatment. However, by day 21 post-treatment, tendon widths and proliferation returned to control levels. Neither ectopic nor abnormal bone, nor aberrant tendon growth was observed over the 21 day time period following the rhPDGF-BB injection into the tendon.

The early increases in microscopic tendon width and cell proliferation corresponded to an increase in the mechanical strength of the tendon. Although there was a return to baseline for cell proliferation and tendon width by day 21 post-treatment, this did not result in a biomechanical loss of tendon strength, rather, the tendon biomechanical improvement was sustained.

The outcome from this study may be especially compelling in the clinic to treat lateral epicondylitis patients. In lateral epicondylitis there are degenerative changes to the extensor carpi-radialis brevis (ECRB) tendon that manifest as pain and functional decrement of the involved arm and hand to tolerate load. It is expected that increased biomechanical strength and structural modification of the tendon as a consequence of rhPDGF-BB therapy that were shown in the rat Achilles tendinopathy model described in this study, will translate clinically into pain abrogation and restoration of function for patients suffering from lateral epicondylitis.

Example 4. Pharmacokinetics of Recombinant Human Platelet-Derived Growth Factor-BB (rhPDGF-BB) in Sprague-Dawley Rats Following Intravenous Administration of rhPDGF-BB The purpose of this study was to evaluate the pharmacokinetics of rhPDGF-BB administered as a single intravenous dose to male Sprague-Dawley rats. This study was designed to assess the clearance of naïve rhPDGF-BB from body fluid (serum) following intravenous administration. To better understand the pharmacokinetic and pharmcodynamic nature of rhPDGF-BB, systemic clearance following intravenous exposure was determined. We hypothesized that rhPDGF-BB will exhibit a fast rate of clearance following intravenous administration.

Study Design

Rat Model

Rat is a commonly used rodent model for evaluating the pharmacokinetic and toxicity of various classes of chemicals and a large historical database exists for the rat. A total of forty eight (48) male Sprague Dawley rats were used in this study. The animals were divided into 2 groups with 6 animals/group/timepoint (Table 7). This study was designed to use the fewest number of animals possible, consistent with the objective of the study, the scientific needs of the inventors and contemporary scientific standards. The design provided sufficient group sizes to allow for meaningful analysis of data. rhPDGF-BB was administered through intravenous delivery with insulin syringes (28.5 G) into the lateral tail-vein.

Test and Control Articles

Test Article was 0.4 mg/ml rhPDGF-BB in 20 mM sodium acetate buffer, pH: 6.0+/−0.5. Control Article was 20 mM sodium acetate buffer, pH 6.0+/−0.5.

At study initiation, at least two unopened, unused vials of the 0.4 mg/ml rhPDGF-BB and 20 mM sodium acetate (Acetate) buffer test articles were retained under the same storage conditions (4° C.) as the vials used for dosing, stability and concentration analysis. Stability and dose verification analyses were performed, which consisted of UV/Vis spectrophotometry and reverse phase HPLC analyses (Appendix II).

Standard laboratory safety procedures were employed for handling the test and control articles. Specifically, gloves, facemask, gown (or lab coat) and eye protection were worn while preparing and administering doses.

Test System

Forty-eight (48) male Sprague Dawley rats were used in this study. The rats used in this study were selected based on their weights. Average weight was approximately 227 grams at the time of treatment. Each rat was identified by a unique tail number that was written with permanent marker. Food and water was withheld for appropriate study-related events such as anesthesia but was otherwise provided ad libitum. Prior to study selection, all animals were screened by visual examination.

Test Article Administration

Intravenous delivery was chosen to achieve 100% bioavailability and pharmacokinetic properties of rhPDGF-BB in serum. The dose level was selected based on the previous dose-response efficacy study of intra-tendon application of rhPDGF-BB in rat tendon collagenase model (see Example 3). The maximum dose concentration to be used in this study is 100 µg or 0.44 mg/kg, based on rats weighing 0.227 kg.

Forty-eight rats were weighed and randomly distributed into two groups of twenty-four rats/group. Rats were assigned randomly to each group according to their body weights.

Body weights were recorded at pre-dose. Group 1 animals received a single intravenous dose of rhPDGF-BB at 0.44 mg/kg (440 µg/kg) at a target dose volume of 1.1 mL/kg. Group 2 animals received vehicle control (NaOAc buffer) at a target dose volume of 1.1 mL/kg. Intravenous injection was achieved by lateral tail vein approach using insulin syringes (28.5 G). Approximately 300 µl serum was collected.

TABLE 7

Treatment Groups

| Group number | Treatment Group | Route of Delivery | Animals (n) | rhPDGF-BB (mg/kg) | Target Volume (mL/kg) | Blood Collection Times* |
|---|---|---|---|---|---|---|
| 1 | rhPDGF-BB | Intravenous (IV) | 24 | 0.44 | 1.1 | 1, 5, 10, 20, 60 minutes, 4, 8, 24, 48, 72, 96 and 168 hours |
| 2 | NaOAc | Intravenous (IV) | 24 | — | 1.1 | 1, 5, 10, 20, 60 minutes, 4, 8, 24, 48, 72, 96 and 168 hours |

*Blood collection times:
Animals 1-6 in all groups = Baseline, 1 min, 1 hr, 48 hr
Animals 7-12 in all groups = Baseline, 5 min, 4h r, 72 hr
Animals 13-18 in all groups = Baseline, 10 min, 8 hr, 96 hr
Animals 19-24 in all groups = Baseline, 20 min, 24 hr, 168 hr Clinical Observations Animals were observed at least daily until sacrifice. Body weights were recorded prior to the rhPDGF-BB injection and before sacrifice. Food consumption was qualitative.

All animals were sacrificed at the appropriate study end points. Upon the completion of the in-life treatment groups, animals were euthanized through CO2 overdose. Death was confirmed by lack of reflexes (blinking, withdrawal, etc.). No gross or histopathology was conducted in this study. No unscheduled animal deaths were recorded.

Serum Collection

Approximately 600 µl blood was collected in serum tubes and centrifuged at 1,800 g at room temperature for 10 minutes to obtain serum. Approximately 300 µl serum was provided in 2 mL eppendorf tubes. The serum was stored at −70 degrees C. prior to analysis.

Serum Analysis rhPDGF-BB serum concentrations were measured at each time point. rhPDGF-BB was quantified using the Quantikine ELISA kit from R&D systems.

Pharmacokinetic Analysis

A non-compartmental module of WinNonlin was used to calculate the following parameters: terminal half-life (t½), Tmax, Cmax, AUC0-last and CL. The analysis were performed using the amount of rhPDGF-BB present at different timepoints as determined in the serum using Quantikine ELISA kit assay.

Statistics

Statistical analyses were limited to descriptive parameters such as means, standard deviations, and coefficient of variation, as appropriate.

Results

Average body weight of all the animals at the time of treatment was 227 grams. Animals received an average dose of 440.53 µg/kg rhPDGF-BB.

Figure 12:
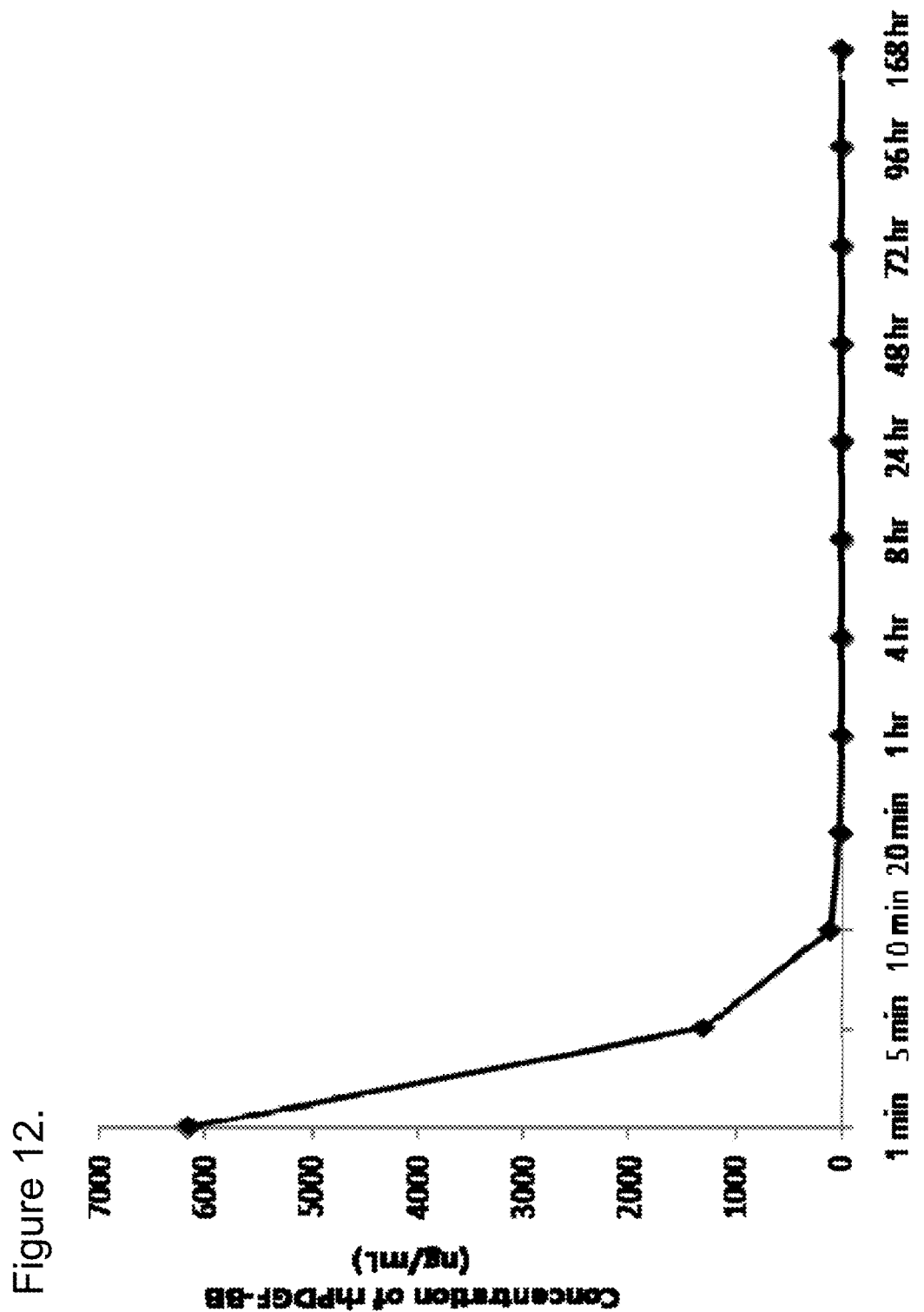
FIG. 12 shows mean serum rhPDGF-BB concentration-time values following IV dosing.

The mean serum rhPDGF-BB concentration-time values are illustrated in FIG. 12. The Cmax (6161.2 ng/mL) was achieved at 1 minute post dose. Thereafter there was a decrease in rhPDGF-BB concentration between 5 minutes and 1 hour. rhPDGF-BB concentrations were below level of quantitation (<0.156 ng/mL) from 1 to 168 hours.

Table 8 represents the pharmacokinetic disposition of IV administered rhPDGF-BB in male Sprague-Dawley rats. The average dose delivered was 440 µg/kg. Tmax was observed at 0.0167 hours (1 minute) with a Cmax of 6161.2 ng/mL. The AUC0-last was 375.64 hr*ng/mL and the clearance (CL) was 17.5 mL/min/kg.

TABLE 8

Pharmacokinetic Data Analysis for IV dosing

| Route | Dose (µg/kg) | Cmax (ng/mL) | Tmax (hours) | AUC0-last (hr*ng/mL) | CL (mL/min/kg) |
|---|---|---|---|---|---|
| IV | 440 | 6161.2 | 0.0167 | 375.64 | 17.5 |

Conclusion

The intravenous (IV) administration of rhPDGF-BB resulted in a high initial systemic exposure. It is an intermediate clearance molecule that is rapidly eliminated from the blood over the first 10 minutes after dosing.

Example 5. Pharmacokinetics of rhPDGF-BB in Sprague Dawley Rats Following Intra-Tendon Administration of rhPDGF-BB The purpose of this study was to evaluate the pharmacokinetics of rhPDGF-BB administered as a single intra-tendon dose to male Sprague-Dawley rats. This study was designed to assess the rhPDGF-BB systemic exposure and clearance following intra-tendon delivery.

Study Design

Rat Model

Rat is a commonly used rodent model for evaluating the pharmacokinetic and toxicity of various classes of chemicals and a large historical database exists for the rat. A total of thirty two (32) male Sprague Dawley rats were used in this study. Animals were randomly distributed into four groups of 8 animals/group (Table 9). This study was designed to use the fewest number of animals possible, consistent with the objective of the study, the scientific needs of the inventors and contemporary scientific standards. The design provides sufficient group sizes to allow for meaningful analysis of data.

Test and Control Articles

Test articles were as follows: (1) 3.4 mg/ml rhPDGF-BB in 20 mM sodium acetate buffer, pH: 6.0+/−0.5; and (2) 0.34 mg/ml rhPDGF-BB in 20 mM sodium acetate buffer, pH: 6.0+/−0.5. The control article was 20 mM sodium acetate buffer, pH 6.0+/−0.5.

At study initiation, at least two unopened, unused vials of the 3.4 and 0.34 mg/ml rhPDGF-BB and 20 mM sodium acetate (Acetate) buffer test and control articles were retained under the same storage conditions (4° C.) as the vials used for dosing, stability and concentration analysis. Stability and dose verification analyses were performed, which consisted of UV/Vis spectrophotometry and reverse phase HPLC analyses.

Doses included in this study were 1.02, 10.2 and 102 µg rhPDGF-BB. The 102 and 10.2 µg doses were achieved by 30 µl injection of 3.4 mg/ml and 0.34 mg/ml, respectively. For the 1.02 µg dose, 0.34 mg/ml was diluted 1:10 with NaOAc buffer.

Standard laboratory safety procedures were employed for handling the test and control articles. Specifically, gloves, facemask, gown (or lab coat) and eye protection were worn while preparing and administering doses.

3). The maximum dose concentration used in this study was 102 µg or 0.347 mg/kg, based on rats weighing 0.294 kg.

Thirty-two male Sprague-Dawley rats with an average weight of 294 grams were randomly distributed into four groups of 8 animals/group. Group 1, 2 and 3 received a single intra-tendon average bolus dose of 347 µg/kg, 34.7 µg/kg and 3.47 µg/kg rhPDGF-BB, respectively, in a target delivery volume of 30 µL per animal (0.102 mL/kg) in the right Achilles tendon near the osteotendinous junction. Group 4 received a single intra-tendon injection of 20 mM sodium acetate buffer in a target delivery volume of 30 µL per animal. Treatment was injected into the right Achilles tendon near the osteotendinous junction using insulin syringes (28.5 G). Animals were bled via tail vein with blank 1 cc syringes (26 G) (~400 µl whole blood, ~200 µl of serum) for serum at the bleed times listed below. rhPDGF-BB in the serum was measured using Quantikine ELISA.

TABLE 9

| | Treatment Groups | | | | |
|---|---|---|---|---|---|
| Group number | Treatment Group | Animals (n) | rhPDGF-BB (µg/kg) | Target Volume (mL/kg) | Blood Collection Times* |
| 1 | rhPDGF-BB | 8 | 347 | 0.102 | 1, 5, 10, 20 minutes, 4, 8, 24, 48, 72, 96 and 168 hours |
| 2 | rhPDGF-BB | 8 | 34.7 | 0.102 | 1, 5, 10, 20 minutes, 4, 8, 24, 48, 72, 96 and 168 hours |
| 3 | rhPDGF-BB | 8 | 3.47 | 0.102 | 1, 5, 10, 20 minutes, 4, 8, 24, 48, 72, 96 and 168 hours |
| 4 | NaOAc (20 mM sodium acetate) | 8 | — | 0.102 | 1, 5, 10, 20 minutes, 4, 8, 24, 48, 72, 96 and 168 hours |

*Blood collection times were:
Animals 1-4 in all groups = Baseline, 1 min, 10 min, 20 min, 4 hr, 24 hr and 72 hr
Animals 5-8 in all groups = Baseline, 5 min, 8 hr, 48 hr, 96 hr and 168 hours Test System Thirty-two (32) male Sprague Dawley rats were used in this study, and were selected based on their weights (approximately 294 grams at the time of injection). Rats were assigned randomly to each group according to their body weights.

Each rat was identified by a unique number that was written on their tails. Food and water was withheld for appropriate study-related events such as anesthesia but was otherwise provided ad libitum. Prior to study selection, all animals were screened by visual examination.

Treatment of the animals was in accordance with FIMR's CCP standard procedures that adhered to the regulations outlined in the USDA Animal Welfare Act (9 CFR, Parts 1, 2, and 3) and the conditions specified in The Guide for Care and Use of Laboratory Animals (ILAR publication, 1996, National Academy Press).

Test Article Administration

The intra-Achilles tendon administration mimics the administration of rhPDGF-BB in the clinic. The injection site at tendon-calcaneous junction mimics the insertional site of tendon and bone.

The dose levels were selected based on the previous dose-response efficacy study of intra-tendon application of rhPDGF-BB in rat tendon collagenase model (see Example Approximately 400 µl blood was collected in serum tubes and centrifuged at 1,800 g at room temperature for 10 minutes to obtain serum. Approximately 200 µl serum was provided in 2 mL eppendorf tubes. The serum was stored at −70 degrees C. prior to analyses to measure the amount of rhPDGF-BB on the stored serum samples.

Clinical Observations

Animals were observed at least daily until sacrifice. Body weights were recorded prior to the rhPDGF-BB injection. Food consumption was qualitative. No unscheduled animal deaths were recorded.

All animals were sacrificed at the appropriate study end points. Upon the completion of the in-life treatment groups, animals were euthanized through $CO_2$ overdose. Death was confirmed by lack of reflexes (blinking, withdrawal, etc.). No gross or histopathology was conducted in this study.

Serum Analysis rhPDGF-BB serum concentrations were measured at each time point. rhPDGF-BB was quantified using the Quantikine® Human PDGF-BB Immunoassay for the Quantitative Determination of Human Platelet Derived Growth Factor-BB Concentrations ELISA kit from R&D Systems (Minneapolis, Minn.) as follows.

First, all reagents in the kit were brought to room temperature before use. Next, a standard curve of rhPDGF-BB was prepared using the same lot of rhPDGF-BB used in the test samples. The rhPDGF-BB was diluted to 10 ng/ml using the diluent buffer provided with the kit. That solution was then serially diluted 1:2 down to a concentration of 0.15625 ng/ml. The samples to be tested were diluted using the same diluent buffer, such that the concentration values fall well within the rhPDGF-BB standard curve of 0.15625 ng/ml to 10 ng/ml.

The number of wells needed to assay all samples in duplicate was determined, and each 8-well strip on the microtiter plates was numbered appropriately. 100 µl per well of Assay Diluent RD1X was added to each well, followed by 100 µl of standards and samples. The plate was then covered with an adhesive cover and incubated at room temperature for approximately 2 hours on an orbital shaker (set to between 50-70 rotations/minute). Each well was aspirated and washed with 300 µL Wash Buffer. Repeat 4 times. Next, 200 µl anti-rhPDGF-BB Conjugate (supplied with R & D kit, no dilution necessary) was added to each well. The plate was covered with a new adhesive cover and incubated at room temperature for approximately 1.5 hours on an orbital shaker set to between 50-70 rotations/minute. The aspiration and wash steps were repeated, and then 200 µl Substrate solution (supplied with R & D kit, no dilution necessary) was added to each well. The samples were then incubated at room temperature in the dark for approximately 30 minutes on an orbital shaker. 50 µl Stop solution (supplied with R & D kit, no dilution necessary) was added to each well and the solution was mixed by pipetting it up-and-down 2-4 times with an 8-channel multi-channel pipette if color development was uneven. The optical density of each well was determined in a microplate reader set to 450 nm (with wavelength correction of 540 nm) within 30 minutes of the addition of Stop Solution. The optical density readings were exported to Microsoft Excel for analysis.

Mean values were calculated for each of the samples. rhPDGF-BB concentrations were calculated for each test sample using the standard curve on each plate. The total amount of protein present in each sample was calculated using rhPDGF-BB concentration and the total volume of each sample.

Pharmacokinetic Analysis

A non-compartmental module of WinNonlin was used to calculate the following parameters: terminal half-life ($t_{1/2}$), time of maximum observed concentration ($T_{max}$), maximum observed concentration ($C_{max}$) occurring at $T_{max}$, area under the drug concentration v. time curve from t=0 hours to t=time of last observation ($AUC_{0-last}$) and bioavailability (% F). The analyses were performed using the amount of rhPDGF-BB present at different time points as determined in the serum using Quantikine ELISA kit assay.

Other parameters can be calculated, such as: area under the drug concentration v. time curve from time=0 extrapolated to infinity, based on last observed concentration ($AUC_{inf}$), total body clearance for intravenous administration (CL), and total body clearance for intra-tendon administration (CL/F).

Statistics

Statistical analyses were limited to descriptive parameters such as means, standard deviations, and coefficient of variation, as appropriate.

Results

The average body weight of all the animals at the time of treatment was 294 grams. Animals received an average dose of 347 µg/kg (102 µg), 34.7 µg/kg (10.2 µg) or 3.47 µg/kg (1.02 µg) rhPDGF-BB.

Figure 13:
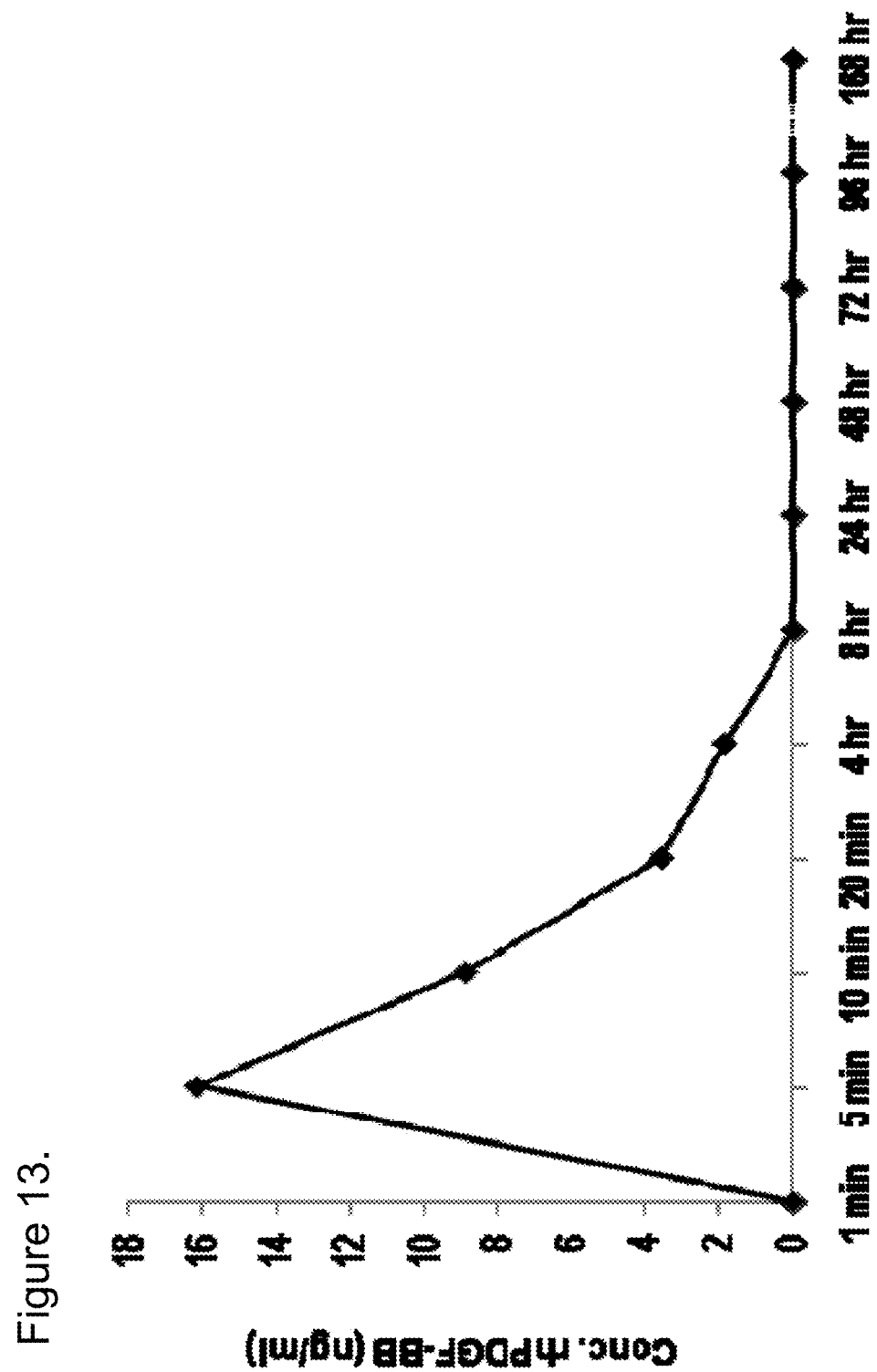
FIG. 13 shows mean serum rhPDGF-BB concentration-time values following IT dosing.

The mean serum rhPDGF-BB concentration-time values for 347 µg/kg dose group are illustrated in FIG. 13. A decrease in concentration of rhPDGF-BB in serum between 5 minutes and 8 hours was observed. From 8 to 168 hours the concentration of rhPDGF-BB in serum was below the level of quantification (<0.156 ng/mL) for the ELISA. The rhPDGF-BB concentration in the serum for 34.7 µg/kg and 3.47 µg/kg dose groups were below the level of quantification (<0.156 ng/mL) at all time points.

Table 10 represents the pharmacokinetic analysis of the parameters for intratendon (IT) dosing of rhPDGF-BB in male Sprague-Dawley rats for the 347 µg/kg dose group, and for intravenous (IV) dosing for the 440 µg/kg dose group described in Example 4. The Tmax was observed at 0.083 hours (4.98 minutes) with a Cmax concentration of 16.3 ng/mL. The AUC0-last was 12.58 ng*hr/mL and the bioavailability was 3.34%. The rhPDGF-BB concentration in the serum for 34.7 µg/kg and 3.47 µg/kg dose groups were below the level of quantification (<0.156 ng/mL) at all time points and thus the pharmacokinetic parameters were not calculated.

TABLE 10

| | Pharmacokinetic Data Analysis for IT dosing (347 µg/kg dose group) and IV dosing (440 µg/kg dose group) | | | | |
|---|---|---|---|---|---|
| Route | Dose (µg/kg) | $C_{max}$ (ng/mL) | $T_{max}$ (hours) | $AUC_{0-last}$ (ng*hr/mL) | % F |
| IT | 347 | 16.3 | 0.0833 | 12.58 | 3.34 |
| IV | 440 | 6161.2 | 0.0167 | 375.64 | — |

Conclusion

The intra-tendon (IT) administration of rhPDGF-BB resulted in a rapid initial low systemic exposure. No detectable serum concentrations of rhPDGF-BB were observed at doses below 347 µg/kg rhPDGF-BB.

At the 347 µg/kg rhPDGF-BB IT dose, approximately 3.34% of the administered dose reached systemic circulation, while Cmax values are only 0.26% of values seen after IV dosing. Therefore, rhPDGF-BB following intra-tendon administration is rapidly cleared following absorption into the serum. Given the low bioavailability (~3.34%) of rhPDGF-BB following intra-tendon administration, this surprisingly predicts that rhPDGF-BB is retained at the site of action.

Example 6: A Phase II Randomized, Single Ascending Dose, Double-Blinded, Placebo Controlled, Multi-Center Study of the Effects of rhPDGF-BB Injection on Lateral Epicondylitis The purpose of this study is to evaluate the effectiveness of rhPDGF-BB Injection as a treatment for lateral epicondylitis, also known as "tennis elbow."

Study Sites/Study Groups.

The study is performed at up to six clinical sites. The study population is one hundred (100) subjects randomized into four groups with twenty five (25) subjects per group. Each cohort includes 5 placebo patients and 20 active treatment patients.

Study Population:

Subjects presenting with a clinical diagnosis of lateral epicondylitis having failed conservative treatment for three (3) months.

Study Design.

The study is a Phase II randomized, single ascending dose, double-blinded, placebo controlled, multi-center study. Eligible subjects meeting inclusion criteria for study enrollment are enrolled after obtaining informed consent for study participation. Subjects are followed for 24 weeks post-procedure. Randomization following study enrollment assigns the subject to one of the following treatment groups following a 1:1:1:1:1 schema: (1) Dose A: Buffer alone—Control Group; (2) Dose B: Buffer+0.45 mg rhPDGF-BB; (3) Dose C: Buffer+0.75 mg rhPDGF-BB; (4) Dose D: Buffer+1.5 mg rhPDGF-BB; and (5) Dose E: Buffer+3.0 mg rhPDGF-BB. The total volume for all doses is 1.5 ml of rhPDGF-BB solution per dose (corresponding to treatment groups of 0.3 mg/ml, 0.5 mg/ml, 1.0 mg/ml, and 2.0 mg/ml of rhPDGF-BB, respectively, and corresponding to 6.4, 10.7, 21.4, and 42.9 μg rhPDGF-BB/kg based on a 70 kg human, respectively). Buffer is 20 mM sodium acetate, pH=6.0.

Randomization is done using a tiered escalation approach. Initial randomization follows a statistically powered escalation scheme assigning subjects to treatment groups utilizing the following pattern: the predetermined, statistically powered number of subjects are randomized to either Dose A (Buffer alone—Control Group) or Dose B (Buffer+0.3 mg/ml rhPDGF-BB). Once the predetermined number is reached for this initial dose tolerance (Dose B), the $2^{nd}$ tier randomization adds the predetermined statistically powered number of subjects to be randomized to either Dose A, Dose B or the additional option of Dose C (Buffer+0.5 mg/ml rhPDGF-BB). This same pattern, adding the statistically powered number of subjects within each tier of the randomization scheme, is repeated until Dose D (Buffer+1.0 mg/ml rhPDGF-BB) and Dose E ((Buffer+2.0 mg/ml rhPDGF-BB) are introduced into the randomization scheme and study enrollment targets are reached.

A single injection of the assigned dose is administered to the tendon using the "peppering technique". The "peppering technique" is an injection method whereby after the needle is inserted into the tender area, multiple small injections are performed by withdrawing, redirecting and reinserting the needle without emerging from the skin.

Subjects are evaluated for local reaction to the injection site (redness, swelling, itching, pain), any increase in pain to the area of chronic injury and any sign of allergic reaction. If subjects report an incidence of the above symptoms, the severity and relationship to the study drug is determined following assessment of the subject and determination by the investigator and documented in the assigned study eCRF. If the severity of the symptom and association is determined to be related to the rhPDGF-BB treatment, the information is immediately to the sponsor as well as appropriate regulatory bodies. A determination is then made whether to continue enrollment or stop subject enrollment at that time.

A pre-procedure Anterior-Posterior (AP) and Lateral x-ray is obtained for baseline imaging and is done up to four (4) weeks prior to the procedure. Additional AP and Lateral x-rays are obtained per study protocol at twenty four (24) weeks post-procedure. Final evaluation of safety is done when all subjects have completed the twenty four (24) week follow-up visit.

Inclusion Criteria.

Subjects included in this study are those whose symptoms can be reproduced with resisted supination or wrist dorsiflexion, and have a clinical diagnosis of lateral epicondylitis and are ≥21 years of age.

Exclusion Criteria.

Subjects excluded from this study are those having had previous corticosteroid injection therapy within the past three (3) months or having undergone surgical intervention for the treatment of lateral epicondylitis; subjects with an allergy to yeast-derived products; subjects with a history of carpal tunnel syndrome; subjects with a history of cervical radiculopathy; and subjects who have had trauma to the affected elbow within six (6) months of treatment.

Duration of Study.

Enrollment is approximately 9 months. Follow-up visits include grip-strength testing and a physical exam of the extremity for up to twenty four (24) weeks post-procedure. Safety endpoints are monitored until last visit at twenty-four (24) weeks.

Primary Outcome Measures.

(1) Safety. Safety and tolerability of rhPDGF-BB are assessed by evaluating the occurrence of adverse events. rhPDGF-BB is safe and tolerated by the subjects.

Secondary Outcome Measures.

The following assessments are completed at visit two prior to the study procedure and at post-procedure study visits at four (4), eight (8), twelve (12) and twenty-four (24) weeks: (1) Disabilities of the Arm, Shoulder and Hand Score (DASH). (2) Visual Analog Score (VAS). (3) Sincerity of effort measured by grip strength testing. Treatment with rhPDGF-BB results in one or more beneficial changes in the clinical outcome for the tendon, such as an improved change from pretreatment score (DASH and VAS), a decrease in pain with applied pressure and/or wrist flexion, increased mobility of the effected extremity, and/or increased grip strength.

Example 7: Effect of rhPDGF-BB-Coated Sutures on Tendon Healing in a Rat Model: A Histological and Biomechanical Study Abstract Introduction.

Achilles tendon tears are common injuries that often require surgical repair. The aim of this study was twofold: (1) determine whether sutures coated with rhPDGF-BB could successfully deliver appropriate amounts of the factor to the repair site, and (2) determine if the sutures coated with rhPDGF-BB would improve healing in a rat achilles tendon model based on biomechanics and histology.

Methods.

4-0 Vicryl suture was coated with varying concentrations of rhPDGF (0, 0.3, 1.0, and 10.0 mg/ml) using a dip-coating process previously described. The 0 rhPDGF group served as the control. ELISA was used to determine resultant concentrations of rhPDGF on the suture after being coated in the varying dipcoat solutions.

Rat Achilles tendons were transected and repaired acutely using one of the four suture types. Tendons were harvested at 4 weeks postoperatively. Histology sections from each specimen were scored for collagen organization and angiogenesis. Uniaxial tensile biomechanical analysis was performed on each specimen providing load and extension data. The raw data was analyzed for the Young's Modulus, Ultimate Tensile Strength and Elastic toughness of each specimen.

Results.

The sutures were successfully coated with the rhPDGF with higher dip-coat concentrations resulting in larger amounts of rhPDGF on the sutures. The histological analysis demonstrated no significant differences in collagen score or angiogenesis between control and PDGF groups. The biomechanical results demonstrated a significant difference in ultimate tensile stress between control (1.0±0.2 MPa) and high dose PDGF groups (1.9±0.5 MPa and 2.1±0.5 MPa). Tensile Young's Modulus was significantly higher in PDGF 10 mg/ml group (7.22, SD 3.79) than all the other groups. This demonstrated a positive dose response and improved strength with PDGF coated sutures.

Conclusion.

This study proved our hypothesis that rhPDGF-coated sutures could improve material properties of repaired tendons in a positive, dose-dependent fashion.

INTRODUCTION

In the current study, we hypothesized that 4-0 Vicryl sutures could be successfully coated with reproducible amounts of rhPDGF-BB, and that augmentation of rat Achilles tendon repair with rhPDGF-BB-coated sutures would enhance the repair in a dose-dependent manner, as assessed biomechanically and histologically.

Materials and Methods

The study was carried out in two parts: 1) in vitro suture coating and analysis and 2) in vivo Achilles tendon repair in a rat model. The procedure was approved by the IUCAC.

Part 1: Suture Coating:

Four groups of 4-0 Vicryl sutures (Ethicon, Somerville, N.J.) were coated with: (1) 20 mM sodium acetate buffer (carrier control), (2) 0.3 mg/ml rhPDGF-BB in buffer, (3) 1.0 mg/ml rhPDGF-BB in buffer, and (4) 10.0 mg/ml rhPDGF-BB in buffer using a dip-coating process, as described previously (Dines J, Weber L, Razzano P, et al. The Effect of Growth Differentiation Factor-5-Coated Sutures on Tendon Repair in a Rat Model. J Shoulder Elbow Surg 2007; 16:215S-221S). Briefly, after treatment with 70% ethanol the sutures (with needles) were submerged in sodium acetate buffer, with or without rhPDGF-BB (0, 0.3, 1.0, and 10.0 mg/ml), for 30 minutes and then air-dried. Unlike the process described by Dines et al., no gelatin was used in the coating solution. Sutures were trimmed to 15 cm lengths for use in the in vivo study. The remaining lengths of the trimmed sutures were used for in vitro analysis.

In Vitro rhPDGF-BB Release:

Sutures (n=5/group) coated in solutions of acetate buffer (group 1) or rhPDGF-BB (group 2-4) were placed in elution buffer (Minimum essential medium with 2% fetal bovine serum, 1% penicillin-streptomycin, 1% L-Glutamine, and 1% HEPES buffer) and incubated at 37° C. on a rocking platform. The elution buffer was fully exchanged at time points of 1, 6, 24, and 48 hours. The total rhPDGF-BB released at each time point was determined using a PDGF-BB ELISA (human PDGF-BB DuoSet, R&D Systems, Minneapolis, Minn.).

Part II: Study Design:

48 Sprague-Dawley rats (350-400 grams) were randomized in a blinded fashion to one of the four treatment groups (n=12 per group). The groups were composed of the four different concentrations of rhPDGF-BB in the dip-coating solution described above with a control group (0 mg/ml rhPDGF-BB) and three experimental groups (0.3, 1.0, and 10.0 mg/ml rhPDGF-BB initial coating concentration).

Surgical Procedure:

All surgeries were performed under sterile conditions. A 1.5 cm skin incision was made over the Achilles tendon. Blunt dissection was used to expose the Achilles tendon. At this point the tendon was transected with a scalpel blade proximal to its insertion on the calcaneus. The tendon was immediately repaired using one modified Mason-Allen stitch and one simple interrupted stitch using sutures from one of the four groups. There was no difficulty in executing either stitch due to the small size of the rat Achilles tendon. The skin was closed with interrupted uncoated Vicryl sutures. Animals were allowed to ambulate normally following the surgical repair. After four weeks the rats were sacrificed and tendons, including a bone block from the calcaneus and the proximal gastroc-soleus muscle complex, were harvested. The specimens were randomly assigned to biomechanical analysis (n=8/group, fresh-frozen) or histological analysis (n=4/group, formalin-fixed).

Biomechanics:

Uniaxial tensile biomechanical analysis was performed on each specimen using an Instron system (Model No. 5566) fitted with a 100N load cell with load accuracy of +/−0.5%. After thawing at 4° C. for up to 4 hours in phosphate-buffered saline (PBS) containing protease inhibitors, samples were dissected to remove excess muscle and the calcaneus and gastroc-soleus ends were wrapped in 220 grit sandpaper. The specimen was secured between pneumatic grips and submerged in a bath of PBS. Samples were pre-loaded (1N) in tension and sample dimensions were measured. The tendon was then subjected to tensile extension at a strain rate of 0.25%/sec. Specimens were pulled to failure and the resulting load and extension data were collected with a personal computer, with data acquired at 10 Hz. After testing, the collected data was analyzed to determine (1) linear stiffness and (2) elastic modulus from the linear portion of the load-displacement or stress-strain curve, respectively. The maximum load and ultimate tensile strength were also calculated from the loading curves.

Histology:

Tendon specimens were detached from the calcaneus at the Achilles tendon insertion site and the repaired Achilles tendons were processed and embedded in paraffin. Saggital sections from each specimen were stained with Mallory's trichrome or Sirius red. Slides were imaged and scored by three blinded observers using a scoring system for collagen organization and degree of angiogenesis, as previously described (Dines J, Weber L, Razzano P, et al. The Effect of Growth Differentiation Factor-5-Coated Sutures on Tendon Repair in a Rat Model. J Shoulder Elbow Surg 2007; 16:215S-221S). Three independent observers who were blinded to treatment group assessed each slide. Total scores were computed for each treatment group and compared for statistical significance.

Statistical Analysis:

The amount of rhPDGF-BB released in vitro was analyzed using a repeated measures ANOVA, with time as the repeated measure. The cumulative amount of rhPDGF-BB released and the total dose delivered versus the initial coating concentration were fit with a nonlinear (log-log scale) least squares fit. A one-way ANOVA with a Bonferroni multiple comparison test was used to determine differences among groups for the biomechanical parameters. Statistical analysis on the histology grading scores was performed using a Kruskal-Wallis test with Dunn's multiple comparison post-hoc test. Biomechanics data are presented as mean±SEM and histology scores are presented as median (range). Significance was determined at $p<0.05$.

Results

Figure 14A:
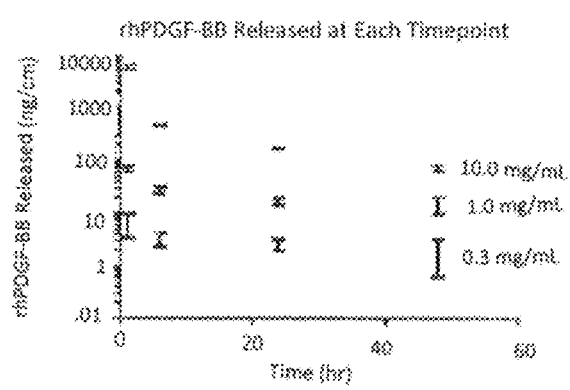
FIG. 14A shows the in vitro release profile for the amount of rhPDGF-BB released at each time point from 4-0 Vicryl sutures.
Figure 14B:
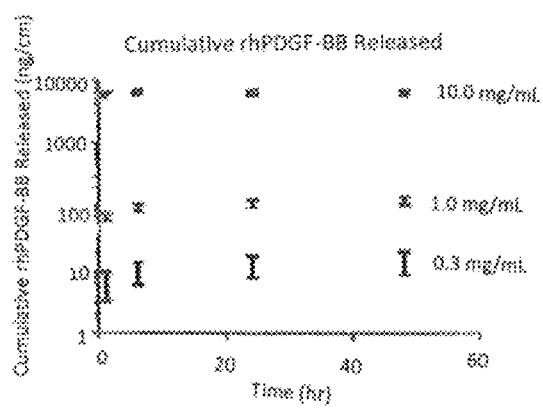
FIG. 14B shows the in vitro cumulative release of rhPDGF-BB over 48 hours from 4-0 Vicryl sutures (mean±SEM).

In Vitro rhPDGF-BB Release:

The in vitro release data are presented as the amount of rhPDGF-BB released, normalized by the length of the suture (ng/cm) (FIGS. 14A and 14B). In vitro release was measured in all groups including Group 1 (0 mg/ml) which was considered as the baseline measurement for the other groups (cumulative release: 1.3±0.1 ng/cm). A bolus release of rhPDGF-BB from the sutures was observed after the first hour of incubation (Group 2: 6.29±3.0 ng/cm; Group 3: 68.81±9.3 ng/cm; and Group 4: 5809.42±541.6 ng/cm) (FIG. 14A). The initial bolus release was followed by a continuous, gradual release of additional rhPDGF-BB through the 48-hour time point. The cumulative amount of rhPDGF-BB released over the 48-hour incubation was dose-dependent with increased rhPDGF-BB released with higher concentrations of the dip-coating solution; Group 4 (10 mg/ml; 6495.9±552.6 ng/cm) was significantly increased (p<0.001) relative to Group 2 (0.3 mg/ml; 14.0±5.7 ng/cm) and Group 3 (1.0 mg/ml; 126.8±18.8 ng/cm) (FIG. 14B). The cumulative amount of rhPDGF-BB released was not significantly different (p>0.05) among Group 2 and Group 3. The cumulative amount of rhPDGF-BB released (Y, ng/cm) was logarithmically proportional ($R^2=0.9575$) to the initial coating concentration (X, mg/ml) by the equation:

$$Y=10^{(1.711*log(X)+2.102)}.$$

Figure 14C:
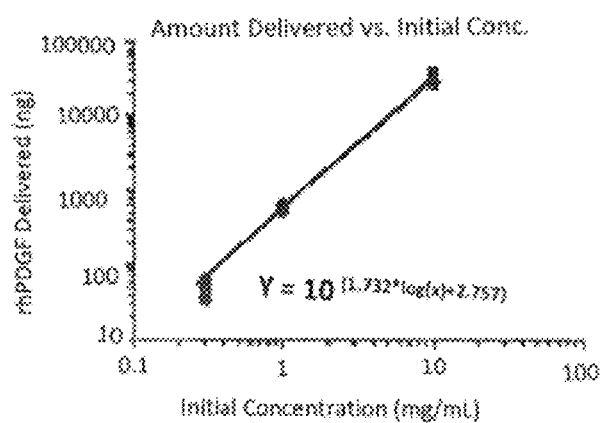
FIG. 14C shows the estimated in vivo cumulative dose of rhPDGF-BB versus initial rhPDGF-BB concentration in the suture coating solution.
Figure 14D:
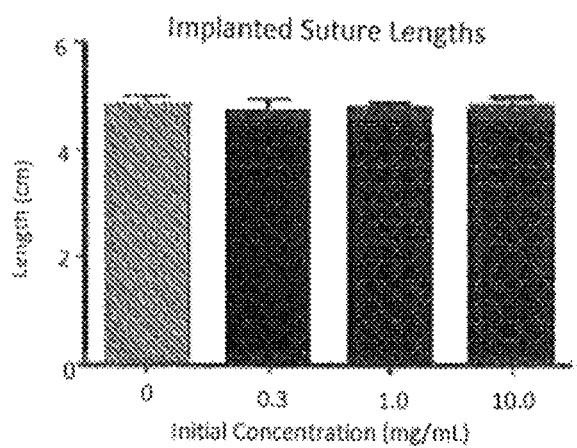
FIG. 14D shows the implanted 4-0 Vicryl suture lengths.

Surgical and Gross Observations:

All animals responded well to the surgery, with the exception of one animal in group 3 (assigned to histology) which died overnight following surgery secondary to complications from anesthesia. The length of suture used for the repair was consistent among groups (Group 1: 4.8±0.1 cm; Group 2: 4.7±0.2 cm; Group 3: 4.8±0.1 cm; and Group 4: 4.8±0.1 cm; p=0.94) (FIG. 14D). Based on the mean amount of rhPDGF-BB released in vitro and the lengths of suture, the in vivo doses (mean±SD) for each group were calculated to be: Group 1: 0 ng; Group 2: 66.0±61.2 ng; Group 3: 602.5±190.9 ng; and Group 4: 31,342.6±6774.5 ng. Similar to the cumulative amount of rhPDGF-BB released, the in vivo dose delivered (Y, ng) was logarithmically proportional ($R^2=0.9859$) to the initial coating concentration (X, mg/ml) (FIG. 14C) with the equation:

$$Y=10^{(1.732*log(X)+2.757)}.$$

Biomechanics:

Five specimens were unable to be used for biomechanical analysis due to an error with the Instron testing machine on that day of testing. The resulting specimen numbers for biomechanical analysis were: n=7 (group 1, 2, and 3) and n=6 (group 4).

No significant differences (p>0.16) in the structural properties of the repaired tendons (ultimate load and stiffness) were observed, however, the mean values for the ultimate load (Group 1: 22.1±1.8 N; Group 2: 31.6±3.5 N; Group 3: 28.0±3.7 N; Group 4: 27.6±1.8 N) and stiffness (Group 1: 6.7±0.4 N/mm; Group 2: 8.9±0.8 N/mm; Group 3: 8.0±1.0 N/mm; Group 4: 7.9±0.7 N/mm) were consistently higher in the groups receiving rhPDGF-BB, relative to the control group (Group 1).

A significant decrease (p<0.05) in the cross-sectional area (CSA) was observed in Group 4 (0.14±0.05 $cm^2$) compared to Group 1 (0.21±0.03 $cm^2$) and Group 2 (0.23±0.04 $cm^2$). The CSA was also significantly decreased (p<0.05) in Group 3 (0.17±0.02 $cm^2$) relative to Group 2. The decrease in CSA resulted in significant differences in the material properties of the repaired tendons (ultimate tensile strength and elastic modulus). There was a significant increase (p<0.05) in the ultimate tensile strength in the 10.0 mg/ml rhPDGF-BB group (2.1±0.2 MPa), relative to the 0 mg/ml (1.0±0.1 MPa) and 0.3 mg/ml (1.4±0.1 MPa) rhPDGF-BB groups and in the 1.0 mg/ml (1.9±0.2 MPa) rhPDGF-BB group compared to the 0 mg/ml group. The elastic modulus was observed to be significantly increased (p<0.05) in the 10.0 mg/ml (7.22±1.5 MPa) rhPDGF-BB group compared to all of the other groups (0 mg/ml: 3.5±0.4 MPa; 0.3 mg/ml: 4.4±0.4 MPa; 1.0 mg/ml rhPDGF-BB: 4.9±0.7 MPa). The 0, 0.3, and 1.0 mg/ml rhPDGF-BB groups were not statistically different from each other.

Histology:

Histology was performed on four animals from each group (n=3 for group 3). Each section was scored by three graders and a mean score was determined. The mean scores are presented as median (range). Histological analysis demonstrated no significant differences in collagen organization or angiogenesis scores among groups. However, a trend towards a more normal appearance was observed in the rhPDGF-BB groups compared to the control group, particularly in the collagen organization scores.

DISCUSSION

In this study we demonstrated that rhPDGF-BB could be successfully coated onto Vicryl sutures, with the amount of rhPDGF-BB released from the sutures in vitro dependent on the initial coating concentration. No significant differences were observed in the structural mechanical properties (ultimate load and stiffness) or by histology, although there was a trend for improvement in these properties in the rhPDGF-BB-treated groups. A dose-dependent response to rhPDGF-BB-coated sutures was observed for the material biomechanical properties, as exhibited by increased material mechanical properties (ultimate tensile stress and elastic modulus).

Biomechanically, significant differences were observed with the highest dose of rhPDGF-BB for the ultimate strength and elastic modulus. The ultimate strength (also referred to as ultimate tensile strength or ultimate tensile stress) and elastic modulus (also referred to as Young's modulus) represent the structural properties (ultimate load and stiffness), normalized by the dimensional properties of the tendon (displacement and CSA), and are a measure of the quality of the tissue. In this study, the decrease in the CSA with increasing dose of rhPDGF-BB accounted for the increase in the material properties. A decrease in CSA is suggestive of a more organized tendon. Although a trend toward improved collagen organization with rhPDGF-BB was observed histologically, this score did not reach statistical significance as was observed for the CSA, potentially due to the small sample size allocated for histology. Regardless, the trend for improved collagen organization, combined with the decrease in the CSA, suggest that the highest dose of rhPDGF-BB promoted a better quality tendon tissue (increased ultimate strength and elastic modulus) relative to the control sutures.

Quantification of the applied dose of rhPDGF-BB is necessary to evaluate the efficiency of the suture coating process and the dose-dependent effect on tendon healing. In vitro analysis demonstrated a significant increase in the amount of rhPDGF-BB released from the highest coating concentration (10 mg/ml), however there was no significant difference noted at the two lower coating concentrations (0.3 and 1.0 mg/ml) even with a 9-fold difference in the average cumulative amount of rhPDGF-BB released (14.0±5.7 ng/cm vs. 126.8±18.8 ng/cm, respectively). This was consistent with the observation that the ultimate strength and elastic modulus were not significantly different among the two lower dose groups.

This study showed that delivery of rhPDGF-BB was able to augment the biological repair of the rat Achilles tendon.

A limitation is this study is how the interpretation of these results is affected by the sample size used in this study. This study was designed with 8 animals/group for biomechanics and 4 animals/group for histology. Due to an error with the Instron testing device on one day of mechanical testing, 5 specimens were not included in the analysis, reducing the statistical power. As a result, smaller differences in properties such as the ultimate load and stiffness could not be deemed significant for the experimental groups, even when they appeared to be increased, on average, relative to the control group.

In the application of growth factors, where the results are often dose-dependent, delivery of larger doses may be required when the size of the animal increases. Preliminary investigations (data not shown) have exhibited a dependence of the delivered dose on both the initial coating concentration and the surface area of the suture, suggesting that scaling the dose for a larger animal is achievable.

The results demonstrated suggests that the use of rhPDGF-BB-coated sutures in clinical applications may have potential for improved tendon healing and increased function for the patient.

REFERENCES

Hess G. Achilles Tendon Rupture: A review of etiology, population, anatomy, risk factors, and injury prevention. Foot Ankle Spec. 2010 February; 3(1):29-32

Sode J, Obel H, Hallas H, et al. Use of Flouroquinolones and risk of Achilles tendon rupture, a population based cohort study. European Journal of Clinical Pharmacology. 63(5): 499-503.

Clain, M. Baxter, D. E. Achilles tendinitis. Foot Ankle Int 1992; 13(8): 482-7.

Giddings V L, Beaupré G S, Whalen R T, Carter D R. (2000). Calcaneal loading during walking and running. Med Sci Sports Exerc. 32(3):627-34.

Costa M A, Wu C, Pham B V, Chong A K, Pham H M, Chang J. Tissue Engineering of flexor tendons: optimization of tenocyte proliferation using growth factor supplementation. Tissue Eng 2006; 12:1937-1943.

Kobayashi M, Itoi E, Minagawa H, et al. Expression of growth factors in early phase of supraspinatus tendon healing in rabbits. J Shoulder Elbow Surg 2006; 15:371-377.

Ignotz R A, Massague J, Transforming growth factor-beta stimulates the expression of fibronectin and collagen and their incorporation in the extracellular matrix. J Biol Chem 1986; 261:4337-45.

Millette E, Rauch Bh, Kenagy D, Daum G, Clowes A W. Platelet derived growth factor-BB transactivates the fibroblast growth factorreceptor to induce proliferation in human smooth muscles cells. Trends Cardiov Med 2006; 16:25-28.

Erikson A, Nister M, Leveen P, Westermark B, Heldin C H, Claesson-Welsh L. Induction of platelet-derived growth factor alpha and beta-receptor mRNA and protein by platelet derived growth factor BB. J Biol Chem 1991; 266:21138-21144.

We claim:

1. A method of treating a tendinopathy comprising administering to an affected tendon an effective amount of a composition comprising a solution of PDGF in a buffer, wherein the effective amount of the composition comprises between about 75 µg and about 7,500 µg of PDGF per dose, wherein the administration to an affected site comprises direct injection into the affected tendon, and further wherein the tendon is chosen from the extensor hallucis longus, the flexor hallucis longus, the extensor digitorum longus, the extensor digitorum brevis, the peroneus longus, the peroneus brevis, the flexor hallucis brevis, the flexor digitorum longus, the posterior tibialis, the Achilles tendon, the plantar fascia, patellar tendon, the anterior tibialis tendon, the hamstring tendon, the semitendinosus tendon, the gracilis tendon, the abductor tendon, the adductor tendon, the flexor tendon, the rectus femoris tendon, the tibialis posterior tendon, the quadriceps femoris tendon, the biceps tendon, the triceps tendon, the extensor carpi radialis brevis, the common extensor tendon, the extensor digitorum, the extensor digiti minimi, the extensor carpi ulnaris, the supinator, the common flexor tendon, the pronator teres, the flexor carpi radialis, the palmaris longus, the flexor carpi ulnaris, the digitorum superficialis, the flexor pollicis brevis, the flexor pollicis longus, the abductor pollicis brevis, the abductor pollicis longus, the flexor digitorum profundus, the flexor digitorum superficialis, the extensor pollicis brevis, and the extensor pollicis longus.

2. The method of claim 1, wherein the tendinopathy is a tendinosis.

3. The method of claim 1, wherein the tendinopathy is a tendinitis.

4. The method of claim 1, wherein the tendinopathy is a tenosynovitis.

5. The method of claim 1, wherein the PDGF is selected from the group consisting of PDGF-AA, PDGF-BB, PDGF-AB, PDGF-CC, and PDGF-DD.

6. The method of claim 1, wherein the PDGF comprises PDGF-BB.

7. The method of claim 6, wherein the PDGF-BB comprises recombinant human (rh) PDGF-BB.

8. The method of claim 6, wherein the effective amount of the composition comprises between about 75 µg and about 7,500 µg of PDGF-BB per dose.

9. The method of claim 6, wherein the effective amount of the composition comprises between about 500 µg to about 1,000 µg of PDGF-BB per dose.

10. The method of claim 6, wherein the effective amount of the composition comprises between about 5,000 µg to about 7,500 µg of PDGF-BB per dose.

11. The method of claim 6, wherein the effective amount of the composition comprises between about 450 µg to about 3000 µg of PDGF-BB per dose.

12. The method of claim 6, wherein the effective amount of the composition comprises between about 400 µg to about 1000 µg of PDGF-BB per dose.

13. The method of claim 6, wherein the effective amount of the composition comprises between about 500 µg to about 900 µg of PDGF-BB per dose.

14. The method of claim 6, wherein the effective amount of the composition comprises between about 600 µg to about 800 µg of PDGF-BB per dose.

15. The method of claim 6, wherein the effective amount of the composition comprises between about 650 µg to about 750 µg of PDGF-BB per dose.

16. The method of claim 6, wherein the effective amount of the composition comprises about 700 µg of PDGF-BB per dose.

17. The method of claim 1, wherein the composition has a volume of about 1.0 to about 2.0 ml per dose.

18. The method of claim 1, wherein the composition has a volume of about 1.5 ml per dose.

19. The method of claim 1, wherein the buffer is selected from the group consisting of phosphate-buffered saline, sodium acetate, ammonium acetate, acetic acid, citric acid, sodium citrate, tris(hydroxymethyl)aminoethane, N-2-hydroxyethylpiperazine-N'-ethanesulfonic acid, 3-(N-morpholino) propanesulfonic acid, 2-(N-morpholino)ethanesulfonic acid, N-(2-acetamido)iminodiacetic acid, piperazine-N,N'-bis(2-ethanesulfonic acid), and N-(2-acetamido)-2-aminoethanesulfonic acid.

20. The method of claim 19, wherein the buffer is sodium acetate.

21. The method of claim 1, wherein the composition is administered using a peppering technique, wherein the needle is inserted into the affected tendon and multiple small injections are performed by withdrawing, redirecting and reinserting the needle into the tendon without the needle to emerging from the skin.

22. The method of claim 1, wherein the composition is administered once a week for up to six months.

23. The method of claim 1, wherein the composition is administered twice a month for up to six months.

24. The method of claim 1, wherein the composition is administered once a month for up to six months.

* * * * *